United States Patent [19]

Wareing

[11] Patent Number: 4,808,607

[45] Date of Patent: Feb. 28, 1989

[54] IMIDAZOLE ANALOGS OF MEVALONOLACTONE AND DERIVATIVES THEREOF FOR USE IN INHIBITING CHOLESTEROL BIOSYNTHESIS AND LOWERING BLOOD CHOLESTEROL LEVEL

[75] Inventor: James R. Wareing, Randolph, N.J.

[73] Assignee: Sandoz Pharm. Corp., E. Hanover, N.J.

[21] Appl. No.: 123,511

[22] Filed: Nov. 20, 1987

Related U.S. Application Data

[60] Continuation-in-part of Ser. No. 079,194, Jul. 29, 1987, Pat. No. 4,755,606, which is a division of Ser. No. 863,267, May 14, 1986, abandoned, which is a continuation-in-part of Ser. No. 736,679, May 22, 1985, Pat. No. 4,668,794.

[51] Int. Cl.$^4$ .................. A61K 31/415; C07D 233/64
[52] U.S. Cl. ..................................... 514/400; 514/397; 548/336; 548/342; 548/343
[58] Field of Search ...................... 548/336, 342, 343; 514/397, 400

[56] References Cited

U.S. PATENT DOCUMENTS 4,530,922  7/1985  Moberg .......................... 548/110 X Primary Examiner—Richard A. Schwartz
Attorney, Agent, or Firm—Gerald D. Sharkin; Richard E. Vila; Melvyn M. Kassenoff

[57] ABSTRACT

Compounds of the formula

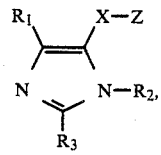

and the pharmaceutically acceptable acid addition salts thereof, wherein the various substituents are defined hereinbelow and the use thereof for inhibiting cholesterol biosynthesis and lowering the blood cholesterol level and, therefore, in the treatment of hyperlipoproteinemia and atherosclerosis, pharmaceutical compositions comprising such compounds and processes for and intermediates in the synthesis of such compounds.

27 Claims, No Drawings

IMIDAZOLE ANALOGS OF MEVALONOLACTONE AND DERIVATIVES THEREOF FOR USE IN INHIBITING CHOLESTEROL BIOSYNTHESIS AND LOWERING BLOOD CHOLESTEROL LEVEL

This application is a continuation-in-part of application Ser. No. 07/079,194, filed July 29, 1987 and now U.S. Pat. No. 4,755,606, which is a division of application Ser. No. 06/863,267, filed May 14, 1986 and now abandoned, which is a continuation-in-part of application Ser. No. 06/736,679, filed May 22, 1985 and now U.S. Pat. No. 4,668,794.

This invention relates to compounds of the formula

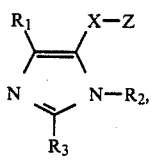

and the pharmaceutically acceptable acid addition salts thereof, wherein $R_1$ is $C_{1-6}$alkyl not containing an asymmetric carbon atom, $C_{3-7}$cycloalkyl, adamantyl-1 or

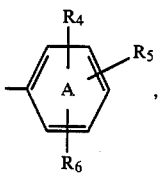

wherein $R_4$, $R_5$ and $R_6$ are as defined below, $R_2$ is $C_{1-6}$alkyl not containing an asymmetric carbon atom, $C_{3-7}$cycloalkyl, adamantyl-1 or

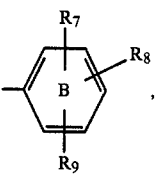

wherein $R_7$, $R_8$ and $R_9$ are as defined below, is hydrogen, $C_{1-6}$alkyl not containing an asymmetric carbon atom, $C_{3-7}$cycloalkyl, adamantyl-1, styryl or

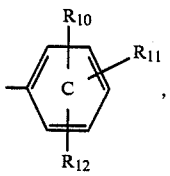

wherein $R_{10}$, $R_{11}$ and $R_{12}$ are as defined below, X is $-(CH_2)_m-$, $-CH=CH-$, $-CH=CH-CH_2-$ or $-CH_2-CH=CH-$, wherein m is 0, 1, 2 or 3, and Z is

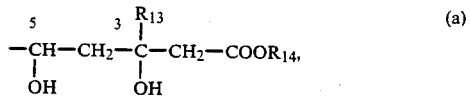

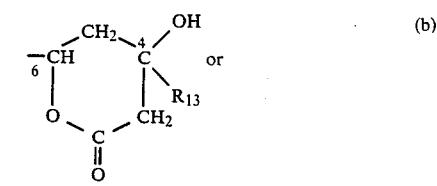

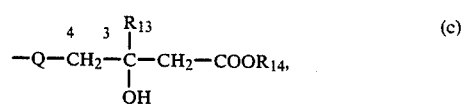

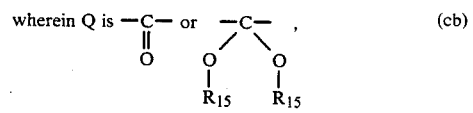

wherein each $R_{15}$ is primary or secondary $C_{1-6}$alkyl not containing an asymmetric carbon atom, the two $R_{15}$'s being the same, or the two $R_{15}$'s taken together are $-(CH_2)_q-$, wherein q is 2 or 3, $R_{13}$ is hydrogen or $C_{1-3}$alkyl, and $R_{14}$ is hydrogen, $R_{16}$ or M, wherein $R_{16}$ is a physiologically acceptable ester group, and M is a pharmaceutically acceptable cation, with the proviso that Z may be a group of Formula c only when (i) X is $-CH=CH-$ or $-CH_2-CH=CH-$, (ii) $R_{13}$ is $C_{1-3}$alkyl or (iii) both (i) and (ii), wherein each of $R^4$, $R_7$ and $R_{10}$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, bromo, phenyl, phenoxy or benzyloxy, each of $R_5$, $R_8$ and $R_{11}$ is independently hydrogen, $C_{1-3}$alkyl, $C_{1-3}$alkoxy, trifluoromethyl, fluoro, chloro, bromo, $-COOR_{17}$, $-N(R_{19})_2$, phenoxy or benzyloxy, wherein $R_{17}$ is hydrogen, $R_{18}$ or M, wherein $R_{18}$ is $C_{1-3}$alkyl, n-butyl, i-butyl, t-butyl or benzyl, and M is as defined above, and each $R_{19}$ is independently $C_{1-6}$alkyl not containing an asymmetric carbon atom, and each of $R_6$, $R_9$ and $R_{12}$ is independently hydrogen, $C_{1-2}$alkyl, $C_{1-2}$alkoxy, fluoro or chloro, with the provisos that not more than one substituent on each of Rings A, B and C independently is trifluoromethyl, not more than one substituent on each of Rings A, B and C independently is phenoxy, and not more than one substituent on each of Rings A, B and C independently is benzyloxy, with the provisos that (1) when Z is a group of Formula c wherein Q is a group of Formula cb, the compound is in free base form and either (i) $R_{14}$ is $R_{16}$ and each $R_{17}$ is independently $R_{18}$ or (ii) $R_{14}$ is M and each $R_{17}$ is independently $R_{18}$ or M and (2) when (i) $R_{14}$ or at least one $R_{17}$ is M or (ii) $R_{14}$ and at least one $R_{17}$ are M, the compound is in free base form, processes for and intermediates in the synthesis thereof, pharmaceutical compositions comprising a compound of Formula I, or a pharmaceutically acceptable acid addition salt thereof, and the use of the compounds of Formula I and the pharmaceutically acceptable acid addition salts thereof for inhibiting cholesterol biosynthesis and lowering the blood cholesterol level and, therefore, in the treatment of hyperlipoproteinemia and atherosclerosis.

By the term "physiologically acceptable ester group" is meant a group which, together with the —COO—radical to which it is attached, forms an ester group which is physiologically acceptable. The preferred such groups are the physiologically acceptable and hydrolyzable ester groups. By the term "physiologically acceptable and hydrolyzable ester group" is meant a group which, together with the —COO—radical to which it is attached, forms an ester group which is physiologically acceptable and hydrolyzable under physiological conditions to yield a compound of Formula I wherein $R_{14}$ is hydrogen and an alcohol which itself is physiologically acceptable, i.e., non-toxic, at the desired dosage level, and which, preferably, is free of centers of asymmetry. Examples of such groups are $C_{1-3}$alkyl, n-butyl, i-butyl, t-butyl and benzyl, collectively referred to as $R_{16}'$.

The compounds of Formula I except those wherein $R_{14}$ and/or one or more $R_{17}$'s are M may be converted into pharmaceutically acceptable acd addition salt form. By the term "pharmaceutically acceptable acid addition salts" is meant those acid addition salts that are physiologically acceptable, i.e., that do not significantly increase the toxicity of the basic compound or otherwise adversely affect its pharmacological activity. Such pharmaceutically acceptable acid addition salts are included within the scope of this invention. Included are salts with strong organic acids, e.g., the methanesulfonate, ethanesulfonate, benzenesulfonate and p-toluenesulfonate salts, and salts with strong inorganic acids, e.g., the hydrochloride, hydrobromide and sulfate salts. The preferred strong acids are those having a pK (the pK of at least the initial dissociation step if the acid has more than one) in water at 25° C. below about 3, more preferably below about 2 and most preferably below about 1.

For the avoidance of doubt, throughout this specification it is the right-hand side of the X radical that is attached to the Z group.

As is self-evident to those in the art, each compound of Formula I wherein Z is a group of Formula a or b (and every subscope and species thereof) has two centers of asymmetry (the two carbon atoms bearing the hydroxy groups in the group of Formula a and the carbon atom bearing the hydroxy group and the carbon atom having the free valence in the group of Formula b) and, therefore, there are four stereoisomeric forms (enantiomers) of each compound (two racemates or pairs of diastereoisomers), provided that $R_{14}$ does not contain any center of asymmetry. The four stereoisomers may be designated as the R,R, R,S, S,R and S,S enantiomers, all four stereoisomers being within the scope of the invention. When $R_{14}$ contains one or more centers of asymmetry, there are eight or more stereoisomers. On the other hand, each compound of Formula I wherein Z is a group of Formula c (and every subscope and species thereof) has a single center of asymmetry (the carbon atom bearing the hydroxy group in the group of Formula c) and, therefore, there are two enantiomers of each compound, provided that $R_{14}$ does not contain any center of asymmetry. The two stereoisomers may be designated as the 3R and 3S enantiomers, both being within the scope of this invention. Since it is preferred that $R_{14}$ not contain a center of asymmetry and for reasons of simplicity, in both cases any additional stereoisomers resulting from the presence of one or more centers of asymmetry in $R_{14}$ will usually be ignored, it being assumed that $R_{14}$ is free of centers of asymmetry. Each pharmaceutically acceptable acid addition salt contains the same number of centers of asymmetry as the corresponding free base provided that the acid does not contain any center asymmetry.

The compounds of Formula I and the pharmaceutically acceptable acid addition salts thereof may be divided into four subgroups, Groups IA, IB, IC and ID, based upon the significances of $R_1$ and $R_2$.

| Group | $R_1$ | $R_2$ |
| --- | --- | --- |
| IA | Other Than Ring A | Ring B |
| IB | Ring A | Other Than Ring B |
| IC | Ring A | Ring B |
| ID | Other Than Ring A | Other Than Ring B |

The compounds and pharmaceutically acceptable acid addition salts of each of Groups IA, IB, IC and ID may be divided into three subgroups based upon the significance of Z viz., Groups IAa, IAb and IAc (those of Group IA wherein Z is a group of Formula a, b or c, respectively), Groups IBa, IBb and Ibc (those of Group IB wherein Z is a group of Formula a, b or c, respectively), Groups ICa, ICb and ICc (those of Group IC wherein Z is a group of Formula a, b or c, respectively) and Groups IDa, IDb and IDc (those of Group ID wherein Z is a group of Formula a, b or c, respectively).

Preferably, one of $R_1$ and $R_2$ is $C_{1-6}$alkyl not containing an asymmetric carbon atom and the other is Ring A (if $R_1$) or Ring B (if $R_2$). $R_3$ is preferably Ring C. More preferably, the preferences set forth in the preceding two sentences occur simultaneously.

Also preferably, at least one of $R_2$ and $R_3$ is other than tertiary alkyl.

Q is preferably -CO-.

$R_1$ is preferably $R_{1x}'$, where $R_{1x}'$, is $C_{1-6}$alkyl not containing an asymmetric carbon atom, more preferably where $R_{1x}''$, is $C_{1-3}$alkyl, n-butyl or i-butyl, even more preferably $R_{1x}'''$, where $R_{1x}'''$ is $C_{1-3}$aklyl, and most perferably i-propyl; or $R_1$ is preferably $R_{1x}'$, where $R_{1y}'$ is Ring A, more preferably $R_{1y}''$, where $R_{1y}''$ is Ring A wherein $R_4$ $R_4'$, is $R_5$ is $R_5'$, and $R_6$ is $R_6'$, even more preferably $R_{1y}'''$, where $R_{1y}'''$ is Ring A wherein $R_4$ is $R_4''$, $R_5$ is $R_5''$, and $R_6$ is $R_6'$, and most perferably $R_{1y}''''$, where $R_{1y}''''$ is Ring A wherein $R_4$ is $R_4''$, $R_5$ is $R_5''$, and $R^6$ is hydrogen, especially phenyl, 3,5-dimethylphenyl or 4-fluorophenyl and more especially 4-fluorophenyl.

$R_2$ is preferably $R_{2x}''$ where $R_{2x}'$ is Ring B, more preferably $R_{2x}''$, where $R_{2x}''$ is Ring B wherein $R_7$ is $R_7'$, $R_8$ is $R_8'$, and $R_9'$, even more preferably $R_{2x}'''$, where $R_{2x}'''$ is Ring B wherein $R_7$ is $R_7''$, $R_8$ is $R_8''$, and $R_9$ is $R_9''$, and most perferably $R_{2x}''''$, where $R_{2x}''''$ is Ring B wherein $R_7$ is $R_7''$, $R_8$ is $R_8''$, and $R_9$ is hydrogen, especially phenyl, 3,5-dimethylphenyl or 4-fluorophenyl and more especially 4-fluorophenyl; or $R_2$ is preferably $R_{2y}'$, where $R_{2y}'$ is $C_{1-6}$alkyl not containing an asymmetric carbon atom, more preferably $R_{2y}''$, where $R_{2y}''$ is $C_{1-3}$alkyl, n-butyl or i-butyl, even more preferably where $R_{2y}'''$, where $R_{2y}'''$ is $C_{1-3}$alkyl, and most perferably i-propyl.

$R_3$ is preferably where $R_3'$, where $R_3'$ is $C_{1-6}$alkyl not containing an asymmetric carbon atom, cyclohexyl or Ring C, more preferably $R_3''$, where $R_3''$ is Ring C, even more preferably $R_3'''$, where $R_3'''$ Ring C wherein $R_{10}$ is $R_{10}'$, $R_{11}$ is $R_{11}'$, and $R_{12}$ is $R_{12}'$, and most preferably $R_3''''$, where $R_3''''$ is Ring C wherein $R_{10}$ is $R_{10}'$, is $R_{11}$ is $R_{11}'$, and $R_{12}$ is $R_{12}'$, especially phenyl.

Each of $R_4$ and $R_7$ is preferably $R_4'$ and $R_7'$, respectively, where each of $R_4'$ and $R_7'$ is independently hydrogen, $C_{1-3}$alkyl, fluoro, chloro or bromo, more preferably $R_4''$ and $R_7''$, respectively, where each of $R_4''$ is $R_7''$ is independently hydrogen, methyl or fluoro, and most preferably hydrogen or fluoro, especially 4-fluoro.

Each of $R^5$ and $R_8$ is preferably $R_5'$ and $R_8'$, respectively, where each of $R_5'$ and $R_8'$ is independently hydrogen, $C_{1-2}$alkyl, fluoro or chloro, more preferably $R_5''$ and $R_8''$, respectively, where each of $R_5''$ and $R_8''$ is independently hydrogen or methyl, and most preferably hydrogen.

Each of $R_6$ and $R_9$ is preferably $R_6'$ and $R_9'$, respectively, where each of $R_6'$ and $R_9'$ is independently hydrogen or methyl, and most preferably hydrogen.

$R_{10}$ is preferably $R_{10}'$, where $R_{10}'$ is hydrogen, $C_{1-3}$alkyl, $C_{1-2}$alkoxy, trifluoromethyl, fluoro, chloro, bromo or phenyl, more preferably $R_{10}''$, where $R_{10}''$ is hydrogen, methyl or fluoro, and most preferably hydrogen.

$R_{11}$ is preferably $R_{11}'$, where $R_{11}'$ is hydrogen, $C_{1-2}$alkyl, fluoro, chloro, bromo, $-COOR_{17}'$ or $-N(R_{19}')_2$, more preferably $R_{11}''$, where $R_{11}''$ is hydrogen or methyl, and most preferably hydrogen.

$R_{12}$ is preferably $R_{12}'$, where $R_{12}'$ is hydrogen or methyl, and most preferably hydrogen.

Preferably, each of Rings A, B and C independently bears a maximum of one substituent selected from the group consisting of t-butyl, trifluoromethyl, phenyl, phenoxy and benzyloxy. More preferably, when any two or all three of the substituents on Ring A [$R_4$ ($R_4'$, etc.), $R^5$ ($R_5'$, etc.) and $R_6$ ($R_6'$ etc.)], Ring B [$R_7'$, etc.), $R_8$ ($R_8'$ etc.) and $R_9$ ($R_9'$, etc.) and Ring C [$R_{10}$ ($R_{10}'$, etc.), $R_{11}$ ($R_{11}'$, etc.) and $R_{12}$ ($R_{12}'$, etc.)] independently are ortho to each other, at least one member of each pair that are ortho to each other is a member of the group consisting of hydrogen, methyl, methoxy, fluoro and chloro. Also more preferably, at least one of the ortho positions of each of Rings A, B and C independently has a member of the group consisting of hydrogen, fluoro and methyl.

$R_{13}$ is preferably $R_{13}'$, where $R_{13}'$ is hydrogen or methyl, and most preferably hydrogen.

$R_{14}$ is preferably $R_{14}'$, where $R_{14}'$ is hydrogen, $R_{16}'$ or M, more preferably $R_{14}''$, where $R_{14}''$ is hydrogen, $C_{1-3}$alkyl or M even more preferably $R_{14}'''$, where $R_{14}'''$ is hydrogen, $C_{1-2}$alkyl or M, and most preferably M, especially sodium.

Preferably, each $R_{15}$ is $C_{1-3}$alkyl or both $R_{15}$'s taken together are $-(CH_2)_q-$; more preferably, each $R_{15}$ is $C_{1-2}$alkyl or both $R_{15}$'s taken together are $-(CH_2)_q-$; and most preferably, each $R_{15}$ is $C_{1-2}$alkyl.

$R_{16}$ is preferably a physiologically acceptable and hydrolyzable ester group, more preferably where $R_{16}'$, where $R_{16}'$ is $C_{1-3}$alkyl, n-butyl, i-butyl, t-butyl or benzyl, even more preferably $C_{1-3}$alkyl and most preferably $C_{1-2}$alkyl, especially ethyl.

Preferably, each $R_{17}$ is independently $R_{17}'$, where $R_{17}'$ is hydrogen, $R_{18}'$ or M; more preferably, each $R_{17}$ is independently $R_{17}''$ where $R_{17}''$ is $C_{1-2}$alkyl or M.

Also preferably, when a compound contains two or more $R_{17}$'s, each $R_{17}$ is independently $R_{18}$ ($R_{18}'$ or $C_{1-2}$alkyl) or the $R_{17}$'s ($R_{17}''$s or $R_{17}'''$s) are identical, each of them being hydrogen or the same M.

More preferably, either (i) $R_{13}$ is hydrogen, $R_{14}$ (if present) is $R_{16}'$, and each $R_{17}$ is independently $R_{18}$ or (ii) $R_{14}$ (if present) and each $R_{17}$ are identical, each of them being hydrogen or the same M.

Preferably, each $R_{18}$ is independently $R_{18}'$, where $R_{18}'$ is $C_{1-3}$alkyl; more preferably, each $R_{18}$ is independently $C_{1-2}$alkyl.

Each $R_{19}$ is preferably $R_{19}'$, where each $R_{19}'$ is independently $C_{1-2}$alkyl.

Any $-CH=CH-$, $-CH=CH-CH_2-$ or $-CH_2-CH=CH-$ as X is preferably trans, i.e., (E).

X is preferably X', where X' is $-CH_2CH_2-$ or $-CH=CH-$, more preferably $-CH=CH-$, and most perferably

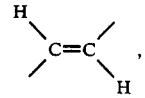

i.e., (E)$-CH=CH-$.

Z is preferably a group of Formula a wherein $R_{13}$ is $R_{13}'$, and $R_{14}$ is $R_{14}'$, a group of Formula b wherein $R_{13}$ is $R_{13}'$ or a group of Formula c wherein Q is $-CO-$, $R_{13}$ is $R_{13}'$, and $R_{14}$ is $R_{14}'$, more preferaby a group of Formula a wherein $R_{13}$ is hydrogen, and $R_{14}$ is $R_{14}''$, a group of Formula b wherein $R_{13}$ is hydrogen or a group of Formula c wherein Q is $-CO-$, $R_{13}$ is hydrogen, and $R_{14}$ is $R_{14}''$, and most preferably a group of Formula a wherein $R_{13}$ is hydrogen, and $R_{14}$ is $R_{14}'''$, preferably $C_{1-2}$alkyl or M, more preferably ethyl or M, most preferably M and especially M'.

m is preferably m', where m' is 2 or 3, and most preferably 2.

Each M is preferably free from centers of asymmetry and is more preferably M', i.e., sodium, potassium or ammonium, and most preferably sodium. For simplicity, each formula in which an M appears has been written as if M were monovalent and, preferably, it is. However, M may also be divalent or trivalent and, when it is, it balances the charge of two or three carboxy groups, respectively. Thus, Formula I and every other formula containing an M embraces compounds wherein M is divalent or trivalent, e.g., compounds containing two or three monocarboxylate-containing anions per cation M. Preferably, when a compound contains two or more M's, they are the same.

As between otherwise identical compounds of Formula I and pharmaceutically acceptable acid addition salts thereof, those wherein Z is a group of Formula a are generally preferred over those wherein Z is a group of Formula b or c.

Insofar as the compounds of Groups IAa, IBa, ICa and IDa and the pharmaceutically acceptable acid addition salts thereof and each of the subgroups thereof are concerned, the erythro isomers are preferred over the threo isomers, erythro and threo referring to the relative positions of the hydroxy groups in the 3- and 5-positions of the group of Formula a.

Insofar as the compounds of Groups IAb, IBb, ICb and IDb and the pharmaceutically acceptable acid addition salts thereof and each of the subgroups thereof are concerned, the trans lactones are generally preferred over the cis lactones, cis and trans referring to the relative positions of $R_{13}$ and the hydrogen atom in the 6-position of the group of Formula b.

The preferred stereoisomers of the compounds of Formula I and the pharmaceutically acceptable acid addition salts thereof having only two centers of asymmetry wherein X is a direct bond, $-CH=CH-$ or $-CH_2-CH=CH-$, and Z is a group of Formula a are the 3R,5S isomer and the racemate of which it is a constituent, i.e., the 3R,5S-3S,5R (erythro) racemate.

The preferred stereoisomers of the compounds of Formula I and the pharmaceutically acceptable acid addition salts thereof having only two centers of asymmetry wherein X is —$CH_2$—, —$CH_2CH_2$—, —$CH_2CH_2CH_2$— or —CH=CH—$CH_2$—, and Z is a group of Formula a are the 3R,5R isomer and the racemate of which it is a constituent, i.e., the 3R,5R-3S,5S (erythro) racemate.

The preferences set forth in the preceding two paragraphs also apply to the compounds of Formula I and the pharmaceutically acceptable acid addition salts thereof wherein Z is a group of Formula a having more than two centers of asymmetry and represent the preferred configurations of the indicated positions.

The preferred stereoisomers of the compounds of Formula I and the pharmaceutically acceptable acid addition salts thereof wherein X is a direct bond, —CH=CH— or —$CH_2$—CH=CH—, and Z is a group of Formula b are the 4R,6S and 4R,6R isomers and the racemate of which each is a constituent, i.e., the 4R,6S-4S,6R (trans lactone) and 4R,6R-4S,6S (cis lactone) racemates, with the 4R,6S isomer and the racemate of which it is a constituent being more preferred and the 4R,6S isomer being most preferred.

The preferred stereoisomers of the compounds of Formula I and the pharmaceutically acceptable acid addition salts thereof wherein X is —$CH_2$—, —$CH_2CH_2$—, —$CH_2CH_2CH_2$— or —CH=CH—$CH_2$—, and Z is a group of Formula b are the 4R,6R and 4R,6S isomers and the racemate of which each is a constituent, i.e., the 4R,6R-4S,6S (trans lactone) and 4R,6S-4S,6R (cis lactone) racemates, with the 4R,6R isomer and the racemate of which it is a constituent being more preferred and the 4R,6R isomer being most preferred.

The preferred stereoisomers of the compounds of Formula I and the pharmaceutically acceptable acid addition salts thereof having just one center of asymmetry wherein Z is a group of Formula c are the 3R isomer and the racemate of which it is a constituent, i.e., the 3R-3S racemate, with the 3R isomer being more preferred. These preferences also apply to the compounds of Formula I and the pharmaceutically acceptable acid addition salts thereof wherein Z is a group of Formula c having more than one center of asymmetry and represent the preferred configuration of the indicated position.

Generally, the compounds of Formula I are preferred over the pharmaceutically acceptable acid addition salts of the corresponding compounds.

Each of the preferences set forth above applies, not only to the compounds of Formula I, but also to the compounds of Groups IA, IB, IC and ID and the pharmaceutically acceptable acid addition salts thereof and those of Groups IAa, IAb, IAc, IBa, IBb, IBc, ICa, ICb, ICc, IDa, IDb and IDc as well as to every other subgroup thereof set forth in the specification, e.g., Groups (i) et seq., unless otherwise indicated. When any preference or group contains a variable, the preferred significances of that variable apply to the preference or group in question, unless otherwise indicated.

Preferred subgroups of Groups IAa, IAb, IAc, IBa, IBb and IBc include the compounds and the pharmaceutically ccceptable acid addition salts (i) of Group IAa wherein $R_1$ is $R_{1x}'$, $R_{2x}''$, $R_3$ is $R_3'$, $R_{13}$ is $R_{13}'$, $R_{14}$ is $R_{14}'$, and X is X', (ii) of (i) wherein $R_1$ is $R_{1x}''$, $R_3$ is $R_3''$, $R_{13}$ is hydrogen, $R_{14}$ is $R_{14}''$, and X is (E)—CH=CH—, (iii) of (ii) wherein $R_3$ is $R_3'''$ and $R_{14}$ is $R_{14}'''$, (iv) of (iii) wherein $R_1$ is $R_{1x}''''$ (especially i-propyl), $R_2$ is and $R_{2x}'''$, and $R_3$ is $R_3''''$, (v)-(viii) of (i)-(iv) wherein $R_{14}$ is M, preferably M' and especially sodium, (ix)-(xvi) of (i)-(viii) wherein the hydroxy groups in the 3- and 5-positions of the group of Formula a have the erythro configuration, (xvii)-(xxiv) the 3R,5S enantiomers of (ix)-(xvi) when X is —CH=CH—and the 3R,5R enantiomers of (ix) when X is —$CH_2CH_2$—, (xxv) of Group IAb wherein $R_1$ is $R_{1x}'$, $R_2$ is $R_{2x}''$, $R_3$ is $R_3'$, $R_{13}$ is $R_{13}'$, and X is X', (xxvi) of (xxv) wherein $R_1$ is $R_{1x}''$, $R_3$ is $R_3''$, $R_{13}$ is hydrogen, and X is (E)—CH=CH—, (xxvii) of (xxvi) wherein $R_3$ is $R_3'''$, (xxviii) of (xxvii) wherein $R_1$ is $R_{1x}''''$ (especially i-propyl), $R_2$ is $R_{2x}'''$, and $R_3$ is $R_3''''$, (xxix)-(xxxii) of (xxv)-(xxviii) wherein $R_{13}$ and the hydrogen atom in the 6-position of the group of Formula b are trans to each other, i.e., the trans lactones, (xxxiii)-(xxxvi) the 4R,6S enantiomers of (xxix)-(xxxii) when X is —CH=CH—and the 4R,6R enantiomers of (xxix) when X is —$CH_2CH_2$—, (xxxvii) of Group IAc wherein $R_1$ is $R_{1x}'$, $R_2$ is $R_{2x}''$, $R_3$ is $R_3'$, $R_{13}$ is $R_{13}'$, $R_{14}$ is $R_{14}'$, each $R_{15}$ is $C_{1-3}$alkyl or both $R_{15}$'s taken together are —$(CH_2)_q$—, and X is X', (xxxviii) of (xxxvii) wherein $R_1$ is $R_{1x}''$, $R_3$ is $R_3''$, $R_{13}$ hydrogen, $R_{14}$ is $R_{14}''$, each $R_{15}$ is $C_{1-2}$alkyl or both $R_{15}$'s taken together are —$(CH_2)_q$—, and X is (E)—CH=CH—, (xxxix) of (xxxviii) wherein $R_3$ is $R_3'''$, $R_{14}$ is $R_{14}'''$, and each $R_{15}$ is $C_{1-2}$alkyl, (xl) of (xxxix) wherein $R_1$ is $R_{1x}''''$ (especially i-propyl), $R_2$ is $R_{2x}'''$, and $R_3$ is $R_3''''$, (xli)-(xliv) of (xxxvii)-(xl) wherein Q is —CO—, (xlv)-(lii) of (xxxvii)-(xliv) wherein $R_{14}$ is M, preferably M' and especially sodium, (liii)-(lxviii) the 3R enantiomers of (xxxvii)-(liii), (lxix) of Group IBa wherein $R_1$ is $R_{1y}''$, $R_2$ is $R_{2y}'$, $R_3$ is $R_3'$, $R_{13}$ is $R_{13}'$, $R_{14}$ is $R_{14}'$, and X is X', (lxx) of (lxix) wherein $R_2$ is $R_{2y}''$, $R_3$ is $R_3''$, $R_{13}$ is hydrogen, $R_{14}$ is $R_{14}''$, and X is (E)—CH=CH—, (lxxi) of (lxx) wherein $R_3$ is $R_3'''$, and $R_{14}$ is, $R_{14}'''$, (lxxii) of (lxxi) wherein $R_1$ is $R_{1y}''''$, $R_2$ is $R_{2y}'''$ (especially i-propyl), and $R_3$ is $R_3''''$, (lxxiii)-(lxxvi) of (lxix)-(lxxii) wherein $R_{14}$ is M, preferably M', and especially sodium, (lxxvii)-(lxxxiv) of (lxix)-(lxxvi) wherein the hydroxy groups in the 3- and 5-positions of the group of Formula a have the erythro configuration, (lxxxv)-(xcii) the 3R,5S enantiomers of (lxxvii)-(lxxxiv) when X is —CH=CH—and the 3R,5R enantiomers of (lxxvii) when X is —$CH_2CH_2$—, (xciii) of Group IBb wherein $R_1$ is $R_{1y}''$, $R_2$ is $R_{2y}'$, $R_3$ is $R_3'$, is $R_{13}'$ and X is X', (xciv) of (xciii) wherein $R_2$ is $R_{2y}''$, $R_3$ is $R_3''$, $R_{13}$ is hydrogen, and X is (E)—CH=CH—, (xcv) of (xciv) wherein $R_3$ is $R_3'''$, (xcvi) of (xcv) wherein $R_1$ is $R_{1y}''''$, $R_2$ is $R_{2y}'''$ (especially i-propyl), and $R_3$ is $R_3''''$, (xcvii)-(c) of (xciii)-(xcvi) wherein $R_{13}$ and the hydrogen atom in the 6-position of the group of Formula b are trans to each other, (ci)-(civ) the 4R,6S enantiomers of (xcvii)-(c) when X is —CH=CH—and the 4R,6R enantiomers of (xcvii) when X is —$CH_2CH_2$—, (cv) of Group IBc wherein $R_1$ is $R_2$ is $R_{1y}''$, $R_2$ is $R_{2y}'$, $R_3$ is $R_{13}'$, $R_{13}$ is $R_{13}'$, $R_{14}$ is $R_{14}'$, each $R_{15}$ is $C_{1-3}$alkyl or both $R_{15}$'s taken together are —$(CH_2)_q$—, and X is X', (cvi) of (cv) wherein $R_2$ is $R_{2y}''$, $R_3$ is $R_3''$, $R_{13}$ is hydrogen, $R_{14}$ is $R_{14}''$, each $R_{15}$ is $C_{1-2}$alkyl or both $R_{15}$'s taken together are —$(CH_2)_q$—, and X is (E)—CH=CH—, (cvii) of (cvi) wherein $R_3$ is $R_3'''$, $R_{14}$ is $R_{14}'''$, and each $R_{15}$ is $C_{1-2}$alkyl, (cviii) of (cvii) wherein $R_1$ is $R_{1y}'''$, $R_2$ is $R_{2y}'''$ (especially i-propyl), and $R_3$ is $R_3''''$, (cix)-(cxii) of (cv)-(cviii) wherein Q is —CO—, (cxiii)-(cxx) of (cv)-(cxii) wherein $R_{14}$ is M, preferably M' and especially sodium, and (cxxi)-(cxxxvi) the 3R enantiomers of (cv)-(cxx).

Groups (ix)-(xvi) and (lxxvii)-(lxxxiv) embrace the 3R,5S-3S,5R racemate and the 3R,5S and 3S,5R enantiomers when X is —CH=CH—, the 3S,5R enantiomer being least preferred, and the 3R,5R-3S,5S racemate and the 3R,5R and 3S,5S enantiomers when X is —$CH_2CH_2$—, the 3S,5S enantiomer being least preferred.

Groups (xxix)-(xxxii) and (xcvii)-(c) embrace the 4R,6S-4S,6R racemate and the 4R,6S and 4S,6R enantiomers when X is —CH=CH—, the 4S,6R enantiomer being least preferred, and the 4R,6R-4S,6S racemate and the 4R,6R and 4S,6S enantiomers when X is —$CH_2CH_2$—, the 4S,6S enantiomer being least preferred.

Insofar as Groups ICa, ICb and ICc are concerned, the preferred subgroups are those that correspond to Groups (i)-(lxviii) wherein $R_{1x}'$ in Groups (i), (xxv) and (xxxvii) is replaced by "$R_{1y}''$", "$R_1$ is $R_{1x}''''$" is deleted from Groups (ii), (xxvi) and (xxxviii) and "$R_{1x}'''$ (especially i-propyl)" in Groups (iv), (xxviii) and (xl) is replaced by $R_{1y}'''$, i.e., Groups (cxxxvii)-(cciv).

Insofar as Groups IDa, IDb and IDc are concerned, the preferred subgroups are those that correspond to Groups (i)-(lxviii) wherein $R_{2x}''$ in Groups (i), (xxv) and (xxxvii) is replaced by $R_{2y}'$, "$R_2$ is $R_{2y}''''$" is added to Groups (ii), (xxvi) and (xxxviii), and $R_{2x}'''$Groups (iv), (xxviii) and (xl) is replaced by "$R_{2y}'''$ (especially i-propyl)", i.e., Groups (ccv)- (cclxxii).

It goes without saying that all of the provisos set forth above in connection with Formula I apply to Groups (i)(cclxxii) and any other group set forth in this specification.

A representative group of the compounds of Formula I and the pharmaceutically acceptable acid addition salts thereof are those wherein one of $R_1$ and $R_2$ is $R_{1x}'$ and the other is Ring A wherein $R_4$ is other than bromo and $R_5$ is other than bromo, —$COOR_{17}$ and —$N(R_{19})_2$ ($R_6$ being as defined above), $R_3$ is Ring C wherein $R_{10}$ is other than bromo and $R_{11}$ is other than bromo, —$COOR_{17}$ and —$N(R_{19})_2$ ($R_{12}$ being as defined above), X is X', and Z is a group of Formula a wherein $R_{13}$ is hydrogen, and $R_{14}$ is hydrogen, a physiologically acceptable and hydrolyzable ester group or M or a group of Formula b wherein $R_{13}$ is hydrogen, each of the variables not defined here being as defined above, with the provisos that not more than one substituent on each of Rings A and C independently is trifluoromethyl, not more than one substituent on each of Rings A and C independently is phenoxy, not more than one substituent on each of Rings A and C independently is benzyloxy, and the compounds must be in free base form when Z contains an M. The preferences for each variable and the preferred groups of these compounds and pharmaceutically acceptable acid addition salts are set forth in columns 3-6 of U.S. Pat. No. 4,668,794 which are hereby incorporated by reference as if set forth herein in their entirety.

The free bases of each group that embraces both free bases and pharmaceutically acceptable acid addition salts are preferred.

The compounds of Formula I and the pharmaceutically acceptable acid addition salts thereof may be synthesized as follows:

Reaction Scheme I

The compounds of Formula I wherein any $R_{17}$ is $R_{18}$ and either x is —CH=CH— or —$CH_2$—CH=CH—, and Z is a group of Formula b having the 4R,6S configuration or X is —$CH_2CH_2$— or —$CH_2CH_2CH_2$—, and Z is a group of Formula b having the 4R,6R configuration may be synthesized by the following series of reactions:

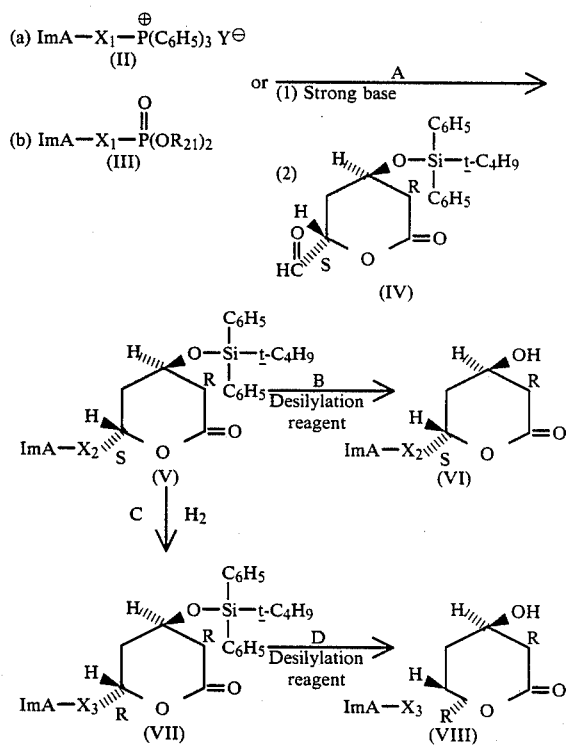

Reaction Scheme II

The compounds of Formula I wherein any $R_{17}$ is $R_{18}$, X is —$CH_2CH_2$—, —$CH_2CH_2CH_2$—, —CH=CH—, —CH=CH—$CH_2$— or —$CH_2$—CH=CH—, and Z is a group of Formula a wherein $R_{14}$ is $R_{16}'$ may be synthesized by the following series of reactions:

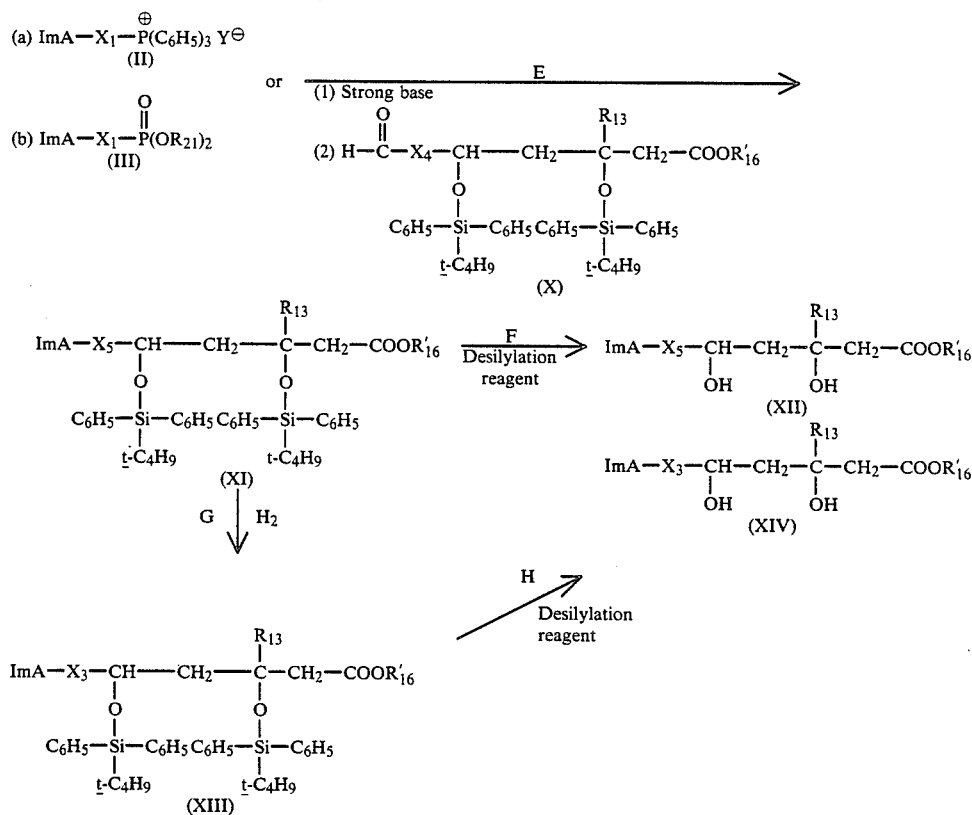

Reaction Scheme III

The compounds of Formula I wherein X is —(CH$_2$)$_m$— or (E)—CH=CH—, and (i) any R$_{17}$ is R$_{18}$, and Z is a group of Formula a wherein R$_{13}$ is hydrogen, and R$_{14}$ is R$_{16}'$ or (ii) R$_{13}$ is R$_{13a}$, R$_{14}$ is M$_2\oplus$ and any M as R$_{17}$ is M$_2\oplus$ may be synthesized by the following series of reactions:

Reaction Scheme IV

The compounds of Formula I wherein Z is a group of Formula a or b may be converted into the corresponding compounds of Formula I wherein Z has a different significance of Formula a or b, and the compounds of Formula I wherein Z is a group of Formula a or b except those containing an M may be converted into the

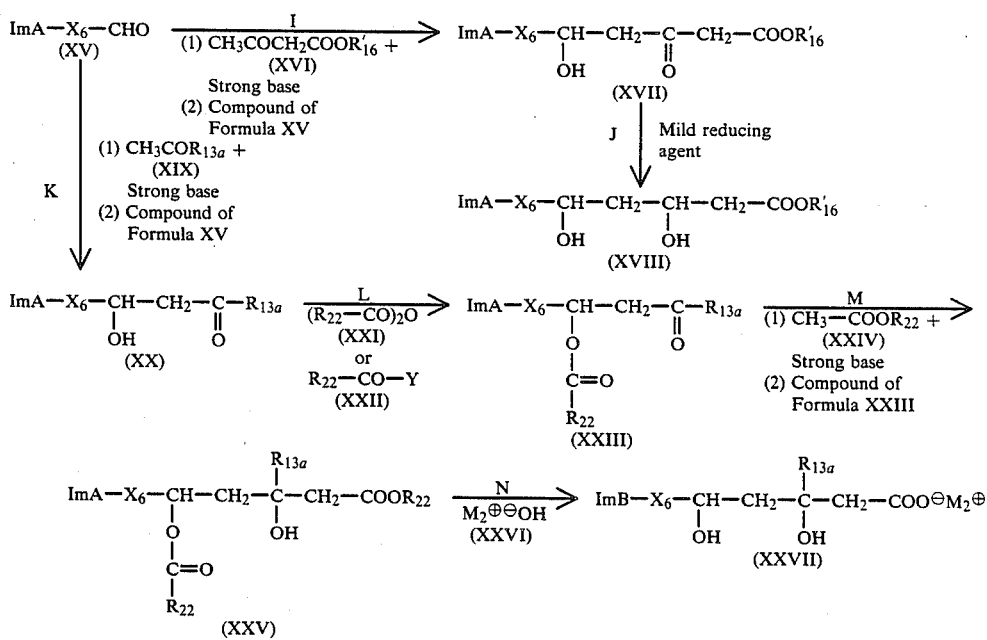

corresponding pharmaceutically acceptable acid addition salts by the following series of reactions:
Reaction Scheme V
The compounds of Formula I wherein Z is a group of Formula c may be synthesized by the following series of reactions:
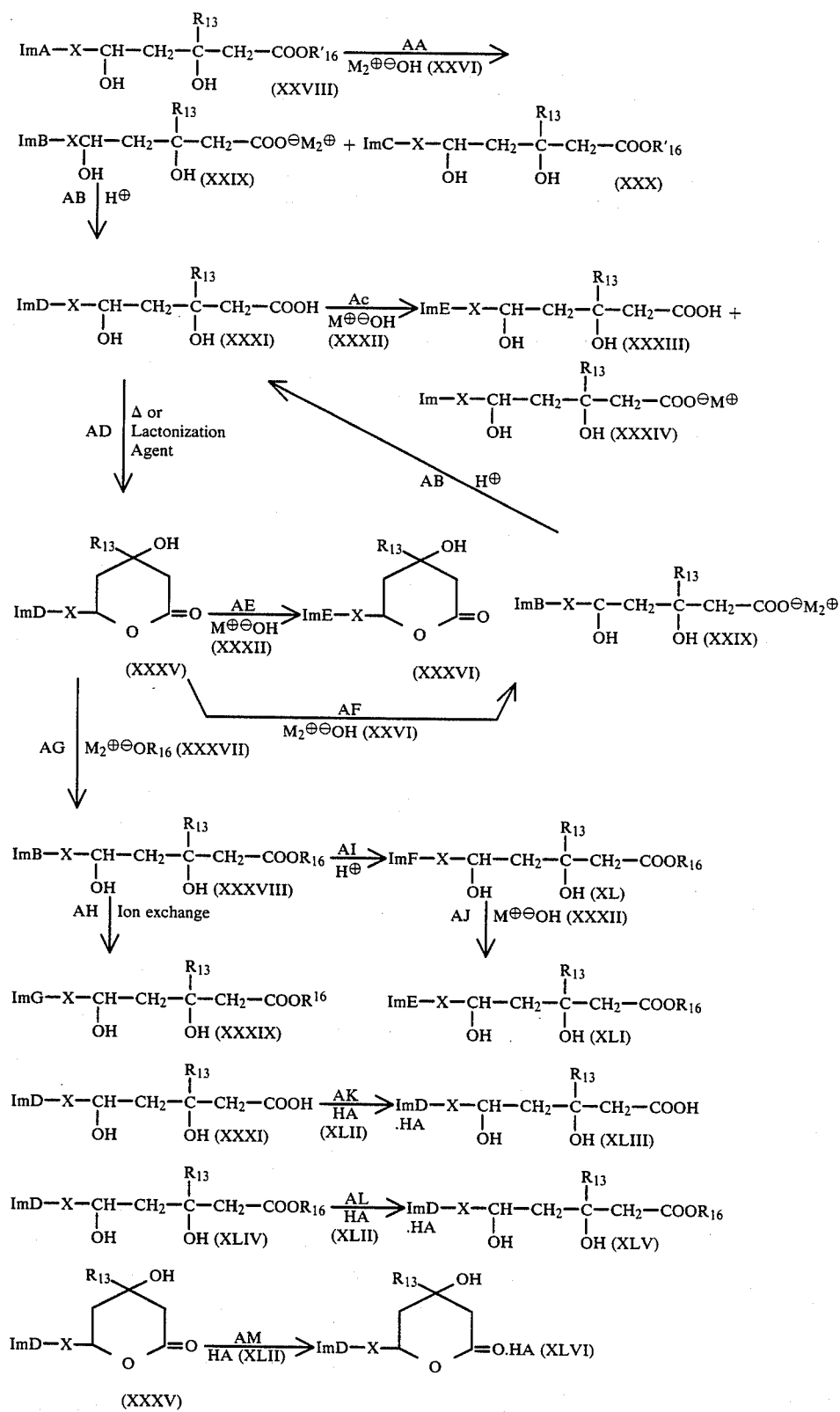

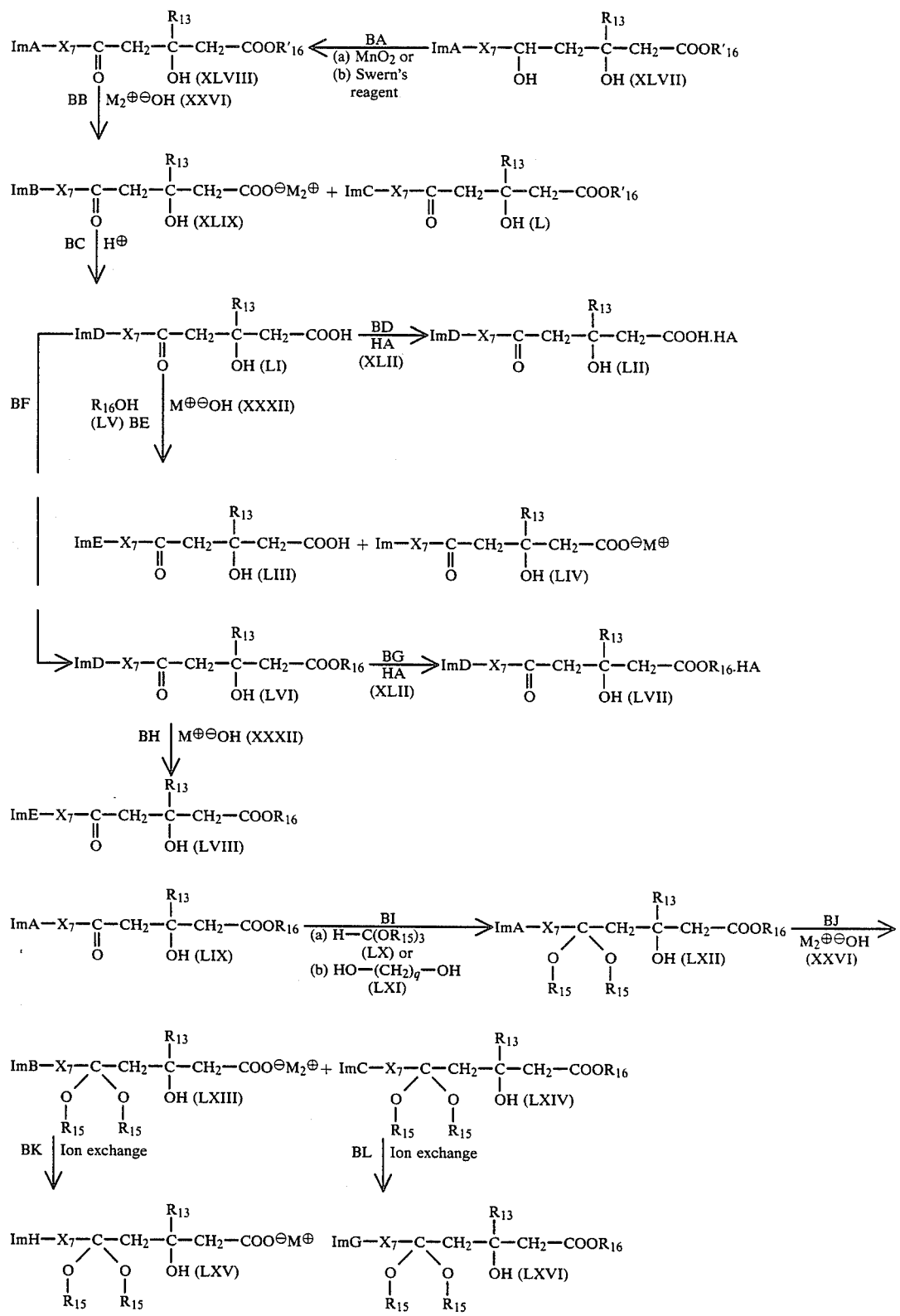
Reaction Scheme VI
The compounds of Formual XV may be synthesized by the following series of reactions:

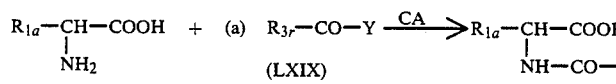
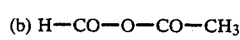
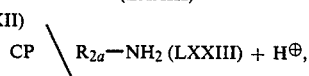
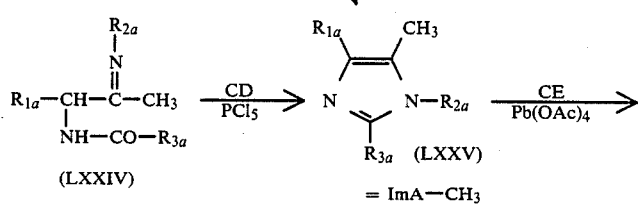
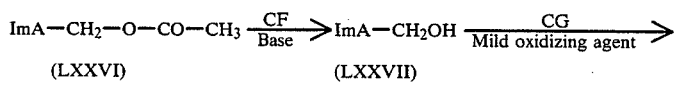
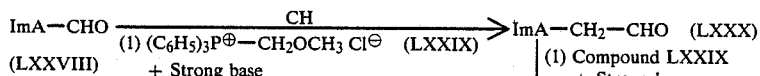
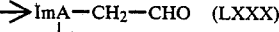
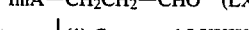
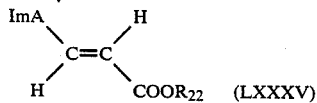
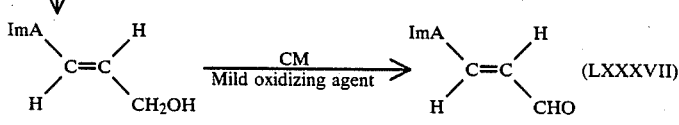
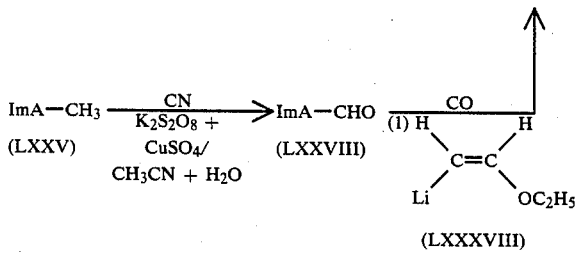

Reaction Scheme VII

The compounds of Formulae II and III and these of Formula LXVIII wherein $R_{1a}$ is $R_{1r}$ may be synthesized by the following series of reactions:

$$\text{ImA—CH}_2\text{OH} \xrightarrow[\text{SOCl}_2]{DA} \text{ImA—CH}_2\text{—Cl} \xrightarrow[(C_6H_5)_3P]{DB} \text{ImA—CH}_2\text{—}\overset{\oplus}{P}(C_6H_5)_3 \text{ Cl}^{\ominus}$$

(LXXVII)      .HCl (XCI)      (XCII)

DC (a) $P(OR_{21})_3$ (XCIII)
(b) (1) $HOP(OR_{21})_2$ (XCIII A) + Strong base
(2) Compound of Formula XCI DI | Mild reducing agent $$\text{ImA—CHO} \qquad \text{ImA—CH}_2\text{—}\overset{\overset{O}{\|}}{P}(OR_{21})_2 \quad (XCIV)$$

(LXXVIII)

$$\text{ImA—CH}_2\text{—CHO} \xrightarrow[\text{Reducing agent}]{DD} \text{ImA—CH}_2\text{CH}_2\text{OH} \xrightarrow[\text{SOCl}_2]{DE}$$

(LXXX)      (XCV)

$$\text{ImA—CH}_2\text{CH}_2\text{—Cl} \xrightarrow[(C_6H_5)_3P]{DF} \text{ImA—CH}_2\text{CH}_2\text{—}\overset{\oplus}{P}(C_6H_5)_3 \text{ Cl}^{\ominus}$$

.HCl (XCVI)      (XCVII)

DG (a) $P(OR_{21})_3$ (XCIII)
(b) (1) Compound of Formula XCIIIA + Strong base
(2) Compound of Formula XCVI $$\text{ImA—CH}_2\text{CH}_2\text{—}\overset{\overset{O}{\|}}{P}(OR_{21})_2 \quad (XCVIII)$$

$$R_{1r}\text{—CHO} + CHCl_3 + NH_3 + KOH + LiCl + C_6H_5CH_2\overset{\oplus}{N}(C_2H_5)_3 \text{ Cl}^{\ominus} \xrightarrow[\text{H}_2\text{O}]{DH}$$

(XCIX)

$$R_{1r}\text{—CH—COOH}$$
$$\quad | $$
$$\quad NH_2 \quad (C)$$

In the foregoing reaction schemes,
HA is a pharmaceutically acceptable acid,
Im is

[structure: imidazole ring with $R_1$, $R_2$ on nitrogens, $R_3$]

ImA is Im wherein each $R_{17}$ is independently $R_{18}$,
ImB is Im wherein each $R_{17}$ is independently $R_{18}$ or $M_2\oplus$,
ImC is Im wherein each $R_{17}$ is independently $R_{18}$ or $M_2\oplus$, with the proviso that at least one $-COO^{\ominus}$ $M_2\oplus$ group is present,
ImD is Im wherein each $R_{17}$ is independently hydrogen or $R_{18}$,
ImE is Im wherein each $R_{17}$ is independently hydrogen, $R_{18}$ or M, with the proviso that at least one $-COO^{\ominus} M\oplus$ group is present,
ImF is Im wherein each $R_{17}$ is independently hydrogen or $R_{18}$, with the proviso that at least one carboxy group is present,
ImG is Im wherein each $R_{17}$ is independently $R_{18}$ or M, with the proviso that at least one $-COO^{\ominus} M\oplus$ group is present,
ImH is Im wherein each $R_{17}$ is independently $R_{18}$ or M,
$R_{1a}$ is $R_1$ wherein $R_{17}$ is $R_{18}$,
$R_{1r}$ is Ring A wherein $R_{17}$ is $R_{18}$,
$R_{2a}$ is $R_2$ wherein $R_{17}$ is $R_{18}$,
$R_{3a}$ is $R_3$ wherein $R_{17}$ is $R_{18}$,
$R_{3r}$ is $R_{3a}$, with the proviso that $R_{3r}$ is other than hydrogen,
$R_{13a}$ is $C_{1-3}$alkyl, preferably methyl,
each $R_{21}$ is independently $C_{1-2}$alkyl, the two $C_{1-2}$alkyl groups preferably being the same,
each $R_{22}$ is independently $C_{1-3}$alkyl, preferably n—$C_{1-3}$alkyl, and most preferably $C_{1-2}$alkyl,
$X_1$ is $-CH_2-$ or $-CH_2CH_2-$,
$X_2$ is $-CH=CH-$ or $-CH_2-CH=CH-$, preferably $-CH=CH-$ and especially (E)$-CH=CH-$,
$X_3$ is $-CH_2CH_2-$ or $-CH_2CH_2CH_2-$, especially $-CH_2CH_2-$,
$X_4$ is a direct bond or $-CH_2-$,
$X_5$ is $-CH=CH-$, $-CH=CH-CH_2-$ or $-CH_2-CH=CH-$, preferably (E)$-CH=CH-$, (E)$-CH=CH-CH_2-$ or (E)$-CH_2-CH=CH-$ and especially (E)$-CH=CH-$,
$X_6$ is $-(CH_2)_m-$ or (E)$-CH=CH-$, especially (E)$-CH=CH-$,
$X_7$ is $-(CH_2)_m-$, $-CH=CH-$, $-CH_2-CH=CH-$ or $-CH=CH-CH_2-$ when $R_{13}$ is $C_{1-3}$alkyl and is $-CH=CH-$ or $-CH_2-CH=CH-$ when $R_{13}$ is hydrogen,
Y is chloro or bromo,
$Y^{\ominus}$ is chloride or bromide,
$M_2\beta$ is sodium or potassium, and
each of the other variables is as defined above.

| Reaction/Type | Reagents, Molar Ratios and Comments | Temperature | Time | Solvent | Inert Atmosphere |
|---|---|---|---|---|---|
| A (Wittig) | Alternative a: (1) 1-2 moles strong base, e.g., sodium hydride or pref. n-butyllithium, per mole II. Pref. slowly add n-butyllithium solution to solution of II. | −40°–5° C., pref. −35°–−20° C. | 5–60 min. | AIO, e.g., HC such as toluene or, pref, ES such as THF | Yes |
| | (2) 0.65–1.5 moles IV per mole II used in Step 1. | −55°–−25° C., pref. −35°–−5° C. | 0.75–18 hrs, pref. 1–4 hrs. | Same as Step 1 | Yes |
| | Alternative b: (1) 1–1.1 mole strong base, pref. n-butyllithium or lithium diisopropylamide, and, optionally, 1.75–2 moles lithium chloride per mole III. Add strong base to other reactants. | −10°–0° C. | 0.7–1.5 hrs. | AIO, pref. ES, esp. THF | Yes |
| | (2) 0.85–1.2 moles IV per mole III used in Step 1. | −10°–25° C. | 1–36 hrs. | Same as Step 1 | Yes |
| | Product (V) is a mixture of the (Z) and (E) (cis and trans, respectively) isomers which may be separated by chromatography. The (E) to (Z) ratio usually is substantially higher with Alternative b than with Alternative a, the former usually yielding only a very small quantity of the (Z) isomer. | | | | |
| B (Deprotection) | 1–4 moles, pref. 2–4 moles, fluoride reagent, esp. tetra-n-butylammonium fluoride or trihydrate thereof, per mole V and 0.99–2 moles, pref. 1–1.5 moles, glacial acetic acid per mole fluoride reagent. First add glacial acetic acid to solution of V, then add fluoride reagent or add V to solution of other reactants. | 20°–60° C. | 2–72 hrs. | AIO, e.g., ES, pref. THF, or acetonitrile | — |
| C (Hydrogenation) | Excess hydrogen (more than 1 mole per mole V) and catalytic amount of platinum dioxide (e.g., 1–5 g. per mole V). Initial hydrogen pressure is conveniently 30–60 p.s.i. | 20°–25° C. | Until 1 mole hydrogen per mole V is taken up | Lower alkanol, e.g., ethanol | — |
| D (Deprotection) | Same as Reaction B (Molar quantities are per mole VII). | Same as B | Same as B | Same as B | — |
| E (Wittig) | Same as Reaction A. (Reactant in Step 2 is X.) Product (XI) is a mixture of the (Z) and (E) (cis and trans, respectively) isomers which may be separated by chromatography. The (E) to (Z) ratio is usually substantially higher with Alternative b then with Alternative a, the former usually yielding only a very small quantity of the (Z) isomer. | Same as A | Same as A | Same as A | Yes |
| F (Deprotection) | Same as Reaction B except utilize 2–12 moles, pref. 4–10 moles, fluoride reagent per mole XI. | Same as B | Same as B | Same as B | — |
| G (Hydrogenation) | Same as Reaction C (Molar quantities are per mole XI). | Same as C | Same as C | Same as C | — |
| H (Deprotection) | Same as Reaction B except utilize 2–8 moles, pref. 4–8 moles, fluoride reagent per mole | Same as B | Same as B | Same as B | — |

-continued

| Reaction/Type | Reagents, Molar Ratios and Comments | Temperature | Time | Solvent | Inert Atmosphere |
|---|---|---|---|---|---|
| I | XIII. (1) Generation of dianion of XVI: 1 mole XVI and 2-2.4 equivalents strong base, pref. 1-1.1 moles sodium hydride then 1-1.1 moles n-butyllithium or 2-2.2 moles lithium diisopropylamide. | −50°–10° C., pref. −20°–5° C. | 0.5-3 hrs. | AIO, e.g., ES, pref. THF | Yes |
| | (2) 1-2.5 moles, pref. 1.2-2.2 moles, more pref. 1.3-2 moles, dianion of XVI (assuming 100% conversion of XVI to its dianion) per mole XV. Product (XVII) is racemic. | −80°–0° C., pref. −50°–0° C., more pref. −30°–−10° C. | 0.3-4 hrs, pref. 0.3 | Same as Step 1 | Yes |
| | (3) Quench with, e.g., saturated aqueous ammonium chloride solution. | Same as Step 2 | 1.5 hrs. | Same as Step 1 | — |
| J (Reduction) | (a) Non-stereoselective: 1-4, pref. 2-4, equivalents transferable hydride per mole XVII, pref. sodium borohydride of complex of t-butylamine and borane. When a racemic XVII is utilized, product (XVIII) is a mixture of all four possible stereoisomers (the erythro and threo racemates) wherein the ratio of the erythro stereoisomers to the threo stereo-isomers is about 3:2–2:3. | −10°–30° C. | 1-8 hrs. esp. ethanol | IO, e.g., lower alkanol, | Yes |
| | (b) Stereoselective: (1) 1-2 moles, pref. 1.02-2 moles, tri-(primary or secondary $C_{2-4}$ alkyl)-borane, pref. triethylborane or tri-n-butylborane, and, optionally, 0.5-8 liters, e.g., 0.75-6.5 liters, air (at 25° C. and 760 mm. Hg) per mole XVII. | 0°–50° C., pref. 0°–25° C. | 0.5-6 hrs., pref. 1-3.5 hrs. | AIO, pref. ES, esp. THF, or pref., mixture of THF and methanol, more pref., a 3-4:1 mixture | — |
| | (2) 0.4-10 moles, pref. 1-10 moles, sodium borohydride per mole XVII. After the reaction, quench reaction mixture with, for example, 10% hydrochloric acid and isolate crude product by extracting with a suitable inert organic solvent (e.g., diethyl ether) and evaporating the solvent at reduced pressure. It is pref. to crystallize the cyclic boron ester, if possible. | −100°–−20° C., pref. −90°–−70° C. | 2-96 hrs., pref. 12-72 hrs. | Same as Step 1 | — |
| | (3) Large excess of anhydrous methanol, e.g., 50-100 moles per mole XVII. | 20°–40° C. | 0.7-5 hrs., pref. 2-4 hrs. | Neat | — |
| | (c) Alternative stereoselective: (p) Preparation of zinc borohydride/diethyl ether: Add 1 mole zinc chloride to 5 l. anhydrous diethyl ether followed by 2 moles sodium borohydride. Stir for 16-18 hrs. and decant off the solution (a 0.15-0.2 M. solution of zinc borohydride in diethyl ether). N.B. The solid should be decomposed very carefully. | 20°–25° C. | 16-18 hrs. | Anhydrous diethyl ether | Yes |

| Reaction/Type | Reagents, Molar Ratios and Comments | Temperature | Time | Solvent | Inert Atmosphere |
|---|---|---|---|---|---|
| | (1) 1-6 moles zinc borohydride (in form of solution produced in Step p) per mole XVII. | $-80°$--$-50°$ C., pref. $-80°$--$-60°$ C. | 0.5-5 hrs., pref. 1-2 hrs. | AIO, pref. ES, esp. diethyl ether or mixture of diethyl ether with another ES | Yes |
| | (2) Add excess methanol, e.g., 10-100 moles per mole XVII. | $-80°$--$-25°$ C., pref. $-80°$--$-75°$ C. → $20°$--$25°$ C. | 1-2 hrs. | Same as Step 1 | — |
| | (3) Add water to excess dilute aqueous acetic acid to quench the reaction mixture or water followed by dilute aqueous acetic acid. | $-80°$--$-25°$ C. NOTE: Warming to $20°$--$25°$ C. can be done after addition of methanol, water or dilute aqueous acetic acid | — | Same as Step 1 | — |
| | When a racemic XVII is utilized in Alternative b or c, product (XVIII) is a mixture of the four possible stereoisomers wherein the ratio of the erythro isomers (racemate) to the threo isomers (racemate) is about 2-20:1, usually 5-15:1. Repeated recrystallization of the cyclic boron ester produced in Step 2 of Alternative b, if a solid, may raise the ratio of even yield pure erythro racemate and mother liquors enriched with the threo racemate. When, however, the solvent in Step 1 of Alternative b is a mixture of THF and methanol, said ratio may be as high as 50-100:1. | | | | |
| K | (1) Generation of monoanion of XIX: 1-1.1 equivalents strong base, pref. lithium diisopropylamide, per mole XIX. | $-80°$--$-40°$ C., pref. $-80°$--$-75°$ C. | 0.25-1.5 hrs. | AIO, e.g., ES, pref. THF | Yes |
| | (2) 1-4 moles, pref. 3 moles, monoanion of XIX (assuming 100% conversion of XIX to its monoanion) per mole XV. | $-80°$--$-40°$ C., pref. $-80°$--$-75°$ C. | 0.25-1.5 hrs. | Same as Step 1 | Yes |
| | (3) Quench with, for example, saturated aqueous ammonium chloride solution. Product (XX) is a racemate. | $-80°$--$-25°$ C. | 1-5 min. | — | — |
| L (Acylation) | 1-3 moles, pref. 2 moles, XXI or XXII per mole XX. When an ES is used as the solvent, also use 1-4 moles, pref. 2.5-3 moles, of a tertiary amine, e.g., pyridine or, pref., 4-dimethylaminopyridine, per mole XX. | $-10°$--$50°$ C., pref. $20°$--$30°$ C. | 2-18 hrs., pref. 4-12 hrs. | Pyridine or anhydrous ES, pref. THF | Yes |
| M | (1) Generation of monoanion of XXIV: 1-1.1 equivalents strong base, pref. lithium diisopropylamide, per mole XXIV. | $-80°$--$0°$ C. | 0.25-1 hr. | AIO, e.g., ES, pref. THF | Yes |
| | (2) 1-4 moles, pref. 3 moles, monoanion of XXIV (assuming 100% conversion of XXIV to its monoanion) per mole XXIII. | $-80°$--$-40°$ C., pref. $-80°$--$-70°$ C. | 0.25-1.5 hrs. | Same as Step 1 | Yes |
| | (3) Quench with, for example, saturated aqueous ammonium chloride solution. | $-80°$--$-25°$ C. | 1-5 min. | — | — |
| N (Hydrolysis) | 1-1.1 equivalents XXVI per mole of ester group to be hydrolyzed. To obtain a product (XXVII) containing one or more | $0°$ C.-reflux, pref. $0°$--$75°$ C., esp. $20°$--$50°$ C. | 1-4 hrs. | Inert aqueous organic, e.g., mixture of water and lower alkanol, pref. | — |

| Reaction/Type | Reagents, Molar Ratios and Comments | Temperature | Time | Solvent | Inert Atmosphere |
|---|---|---|---|---|---|
| AA (Hydrolysis) | —$COOR_{18}$ groups, utilize 1 or less than 1 equivalent XXVI per mole of ester group to be hydrolyzed and separate the desired product(s) from the resulting mixture. | when all ester groups are to be hydrolyzed and 0°-25° C. otherwise | | mixture of water and methanol or, esp. ethanol | — |
| | 1-1.3 equivalents XXVI per mole of ester group to be hydrolyzed. To obtain a product (XXIX or XXX) containing one or more ester groups and/or if it is desired to isolate XXIX or XXX, utilize 1 or less than 1 equivalent, e.g., 0.93-0.99 equivalent, XXVI per mole of ester group to be hydrolyzed and separate the desired product(s) from the resulting mixture if a mixture is obtained. | 0° C.-reflux, pref. 0°-75° C., esp. 20°-70° C. when all ester groups are to be hydrolyzed and 0°-25° C. otherwise | 1-4 hrs. | Inert aqueous organic, e.g., mixture of water and lower alkanol, pref. mixture of water and methanol or, esp. ethanol | — |
| AB (Acidification) | 1 equivalent acid, e.g., 2N. hydrochloric acid, per mole of —$COO^{\ominus} M_2^{\oplus}$ group to be acidified. | 0°-25° C., pref. 0°-15° C. when one or more —$COOR_{18}$ groups are present | 1-5 min. | Water or mixture of water and water-miscible inert organic solvent, e.g., methanol, ethanol, diethyl ether or THF | — |
| AC (Neutralization) | 0.95-1 equivalent, pref. 0.96-0.98 equivalent, XXXII per mole of carboxy group to be neutralized and separate the desired product(s) from the resulting mixture if a mixture is obtained. | 0°-25° C., pref. 20°-25° C. when no —$COOR_{18}$ group is present and otherwise 0°-15° C. | 2-10 min. | Same as AA | — |
| AD (Lactonization) | Alternative a: Use of catalytic amount of strong acid such as p-toluenesulfonic acid monohydrate is optional but usually omit. Use of Dean-Stark apparatus is pref. if solvent forms azeotrope with water. | 75° C.-reflux, pref. 75°-150° C., esp. 80°-120° C. | 3-18 hrs., pref. 4-7 hrs. | AIO, pref. HC, e.g., benzene, toluene or xylene or mixture thereof | — |
| | Alternative b: 1-1.5 moles of a lactonization agent, e.g., a carbodiimide, pref. a water-soluble carbodiimide such as N—cyclo-hexyl-N′—[2′-(N″—methylmorpholinium)-ethyl]carbodiimide p-toluenesulfonate, per mole XXXI. When ImD contains one or more carboxy groups, run reaction in relatively dilute solution to minimize formation of undesired by-products. Alternative b often results in higher yields of XXXV than Alternative a. Racemic erythro XXXI yields racemic trans (lactone) XXXV, racemic threo XXXI yields racemic cis (lactone) XXXV, mixture of racemic erythro and threo XXXI yields mixture of racemic trans and cis (lactones) XXXV, and single enantiomer of XXXI yields single enantiomer of XXXV, e.g., 3R,5S erythro XXXV yields 4R,6S trans XXXV. | 10°-35° C., pref. 20°-25° C. | 2-8 hrs., pref. 3-4 hrs. | AIO, pref. HLA, esp. methylene chloride | — |
| AE (Neutralization) | 0.95-1 equivalent, pref. 0.96-0.98 equivalent, XXXII per mole of carboxy group to be neutralized and separate the desired | 0°-25° C., pref. 0°-15° C. | 2-10 min. | Same as AA | — |

-continued

| Reaction/Type | Reagents, Molar Ratios and Comments | Temperature | Time | Solvent | Inert Atmosphere |
|---|---|---|---|---|---|
| AF (Hydrolysis) | product(s) from the resulting mixture if a mixture is obtained. 1-1.3 equivalents or, if it is desired to isolate XXXVII and/or if ImD contains one or more —COOR$_{18}$ groups not to be hydrolyzed, 0.95-1 equivalent, pref. 0.97-0.99 equivalent, XXVI per mole XXXV plus, in each case, 1-1.05 equivalents or, if it is desired to isolate XXXVII and/or if ImD contains one or more —COOR$_{18}$ groups not to be hydrolyzed, 0.95-1 equivalent, pref. 0.97-0.99 equivalent, XXVI per mole of carboxy group and —COOR$_{18}$ group to be hydrolyzed and separate the desired product(s) from the resulting mixture if a mixture is obtained. Racemic trans (lactone) XXXV yields racemic erythro XXXVII, racemic cis (lactone) XXXV yields racemic threo XXXVII, mixture of racemic trans and cis (lactones) XXXV yields mixture of racemic erythro and threo XXXVII, and single enantiomer of XXXV yields single enantiomer of XXXVII, e.g., 4R,6S trans XXXV yields 3R,5S erythro XXXVII. | 0° C.-reflux, pref. 0°–75° C., more pref. 20°–75° C., esp. 40°–60° C. | 1-6 hrs., pref. 1-4 hrs. | Same as AA | — |
| AG (Esterification) | At least 2 moles, e.g., 2-10 moles, pref. 2.05-2.5 moles, XXXVII per mole XXXV plus, in each case, 1 mole XXXVII per mole of carboxy group (in ImD) and separate the desired product(s) from the resulting mixture if a mixture is obtained. Racemic trans lactone XXXV yields racemic erythro XXXVIII, racemic cis (lactone) XXXV yields racemic threo XXXVIII, mixture of racemic trans and cis (lactones) XXXV yields mixture of racemic erythro and threo XXXVIII, and single enantiomer of XXXV yields single enantiomer of XXXVIII, e.g., 4R,6S trans XXXV yields 3R,5S erythro XXXVIII. | 0°–70° C., pref. 20°–25° C. | 2-12 hrs. | AIO, e.g., ES such as THF or alcohol of the formula R$_{16}$—OH (R$_{16}$ same as in XXXVII), if a liquid | — |
| AH (Ion Exchange) | Utilize an ion exchange resin such as Amberlite IR-P64 having the desired M$^{\oplus}$ ions by the conventional procedure, e.g., dissolve XXXVIII in water, load onto ion exchange resin column and elute the product(s) with appropriate buffer. | 20°–25° C. | — | — | — |
| AI (Acidification) | Same as Reaction AB | Same as AB | Same as AB | Same as AB | — |
| AJ (Neutralization) | Same as Reaction AC | Same as AC | Same as AC | Same as AC | — |
| AK (Acidification) | 1 equivalent XLII per mole XXXI. If XLII is a gas such as hydrogen chloride, can bubble excess XLII through solution of XXXI. Can start with XXIX, XXXIII, XXXIV, etc. and synthesize XXXI by or analogously to Reaction AB. | 0°–25° C., pref. 20°–25° C. | 1-15 min., pref. 1-5 min. | IO, pref. lower alkanol, e.g., methanol or ethanol, or ES, e.g., diethyl ether, water or mixture of water and IO | — |

-continued

| Reaction/Type | Reagents, Molar Ratios and Comments | Temperature | Time | Solvent | Inert Atmosphere |
|---|---|---|---|---|---|
| AL (Acidification) | Same as Reaction AK (Molar quantities are per mole XLIV). Can start with XXX, XXXVIII, XLI, etc. and synthesize XLIV by or analogously to Reaction AI. | Same as AK | Same as AK | Same as AK | — |
| AM (Acidification) | Same as Reaction AK (Molar quantities are per mole XXXV). Can start with XXXVI and synthesize XXXV analogously to Reactions AB and AI. | Same as AK | Same as AK | Same as AK | — |
| BA (Oxidation) | (a) When $X_7$ is $-CH=CH-$ or $-CH_2-CH=CH-$: 5–50 moles manganese dioxide (pref. activated) per mole XLVII. | 20°–80° C., pref. 40°–80° C. | 1–4 days | AIO, pref. ES or HC, esp. toluene | Yes |
|  | (b) When $X_7$ is $-(CH_2)_m-$ or $-CH=CH-CH_2-$: (1) Preparation of Swern's Reagent: 0.9596 l. oxalyl chloride and 1.561 l. dimethyl sulfoxide per mole XLVII to be used in Step. 2. | −20°–0° C. | 5–15 min. | Neat | Yes |
|  | (2) Swern's Reagent from Step 1 and 6.969 l. triethylamine per mole XLVII. | −60°–−40° C., pref. −50° C. | 1–6 hrs. | Methylene chloride | Yes |
| BB (Hydrolysis) | Same as Reaction AA | Same as AA | Same as AA | Same as AA | — |
| BC (Acidification) | Same as Reaction AB | Same as AB | Same as AB | Same as AB | — |
| BD (Acidification) | Same as Reaction AK (Molar quantities are per mole LI). Can start with XLIX or LIII and synthesize LI by or analogously to Reaction BC. | Same as AK | Same as AK | Same as AK | — |
| BE (Esterification) | Same as Reaction AC | Same as AC | Same as AC | Same as AC | — |
| BF (Esterification) | 1–5 moles LV and catalytic amount of acid, e.g., p-toluenesulfonic acid monohydrate, per mole LI. When reaction is run neat, use large excess of LV, e.g., 50–100 moles, per mole LI. When ImD contains one or more carboxy groups not to be esterified, use 0.9–1 mole LV per mole LI and separate the desired product from the resulting mixture. | 20°–40° C. | 1–6 hrs. | AIO, e.g., ES such as THF or neat (if LV is a liquid) | — |
| BG (Acidification) | Same as Reaction AK (Molar quantities are per mole LVI). Can start with L, LVIII, etc. and synthesize LVI by or analogously to Reaction BC. | Same as AK | Same as AK | Same as AK | — |
| BH (Neutralization) | Same as Reaction AC | Same as AC | Same as AC | Same as AC | — |
| BI (Ketalization) | (a) When each $R_{15}$ is $C_{1-6}$alkyl not containing an asymmetric carbon atom: 3–5 moles LX and catalytic amount of pyridinium p-toluenesulfonate per mole LIX. | 20°–25° C. | 24–72 hrs. | AIO, e.g., HLA or HC, esp. methylene chloride or benzene | Yes |
|  | (b) When the two $R_{15}$'s taken together are $-(CH_2)_q-$: 2–3 moles LXI and catalytic amount (e.g., 1–3 g.) of pyridinium p-toluenesulfonate per mole LIX. | 20°–25° C. | 24–72 hrs. | Same as Alternative a | Yes |
| BJ (Hydrolysis) | Same as Reaction AA | Same as AA | Same as AA | Same as AA | — |
| BK (Ion Exchange) | Same as Reaction AH | Same as AH | Same as AH | Same as AH | — |
| BL (Ion Exchange) | Same as Reaction AH | Same as AH | Same as AH | Same as AH | — |
| CA (Acylation) | (a) When $R_{1a}$ is other than hydrogen: | | | | |

| Reaction/Type | Reagents, Molar Ratios and Comments | Temperature | Time | Solvent | Inert Atmosphere |
|---|---|---|---|---|---|
| | 1-1.5 moles, pref. 1.1-1.3 moles, LXIX and 2-3 equivalents of a base such as sodium hydroxide per mole LXVIII. Simultaneously add solution of LXIX and base to basic solution of LXVIII or add LXIX neat or in solution to mixture of base and LXVIII. Reaction mixture must be basic at all times. Combine reactants at $-5°$ to $-15°$ C. and then, if desired, reaction mixture may be allowed to warm to 20°-25° C. if no ester group is present. After the reaction, acidify with, for example, concentrated sulfuric or hydrochloric acid.<br>(b) When $R_{3a}$ is hydrogen: 2-4 moles LXX per mole LXVIII. Start reaction at 0°-10° C. and after ~40 min. reaction mixture may be allowed to warm to 20°-25° C. See Muramatsu et al., Bull. Chem. Soc. Japan 38, 244-246 (1965). See Sheehan et al., J. Am. Chem. Soc. 80, 1154-1158 (1958) for alternate procedure. | $-5°-15°$ C. ($\rightarrow$ 20°-25° C. if no $-COOR_{18}$ group is present)<br>0°-10° C. $\rightarrow$ 20°-25° C. | 1-5 hrs.<br>1-2 hrs. | Mixture of ES, pref. dioxane or THF, and water<br>90% formic acid or acetic acid | —<br>— |
| CB | Alternative a: 2-4 moles, pref. 3 moles, acetic anhydride, 1-3 moles, pref. 2-2.2 moles, of an organic base, pref. 2 moles of a tri-($C_{1-3}$alkyl)amine, e.g., triethylamine, and catalytic amount, e.g., 0.1 mole, of 4-dimethylaminopyridine, per mole LXXI. After the reaction, reaction mixture may be quenched with, for example, methanol or water.<br>Alternative b: (1) 2-6 moles, pref. 3-5 moles, acetic anhydride, 4-6 moles of an organic base, pref. pyridine, and catalytic amount, e.g., 0.005-0.1 mole, of 4-dimethylaminopyridine per mole LXXI.<br>(2) Add solvent and heat. | 15°-140° C., pref. 20°-30° C.<br>20°-25° C.<br>100°-130° C. | 2-24 hrs.<br>0.5-1.5 hrs.<br>2-4 hrs. | Neat<br>Neat<br>Glacial acetic acid | Yes<br>Yes<br>Yes |
| CC | Alternative a: 1-5 moles LXXIII and catalytic amount (e.g., 0.1-5 g.) of p-toluenesulfonic acid monohydrate per mole LXXII. Pref. use Dean-Stark apparatus if solvent forms azeotrope with water.<br>Alternative b: 10-20 moles LXXIII, 30-50 moles of a dehydrating agent such as magnesium sulfate and catalytic amount (e.g., 0.5-5 g.) of p-toluenesulfonic acid monohydrate per mole LXXII. | 80° C.-reflux, pref. 100°-111° C.<br>20°-40° C. | 18-72 hrs.<br>4-6 days | AIO, pref. HC, e.g., benzene or toluene<br>AIO, pref. mixture of HLA and HC, esp. mixture of methylene chloride and benzene | Yes<br>Yes |
| CD | 1.5-3 moles, pref. 1.9-2.1 moles, phosphorus | $-30°-30°$ C. $\rightarrow$ | 2-72 hrs. | HLA, pref. chloroform or | Yes |

-continued

| Reaction/Type | Reagents, Molar Ratios and Comments | Temperature | Time | Solvent | Inert Atmosphere |
|---|---|---|---|---|---|
| | pentachloride per mole LXXIV. Combine reactants at −30°–30° C. and maintain at 20°–55° C. for balance of reaction time. Quench reaction mixture at 0°–30° C. with water and then make basic with, for example, 10–50% sodium hydroxide solution or quench with aqueous base, e.g., mixture of ice and sodium hydroxide solution. | 20°–55° C. | | methylene chloride, or mixture of HC and HLA, pref. mixture of toluene and methylene chloride | — |
| CE | 1–2.1 moles lead tetraacetate and, pref., catalytic amount (e.g., 0.5–2 g.) of benzoyl peroxide per mole LXXV. Generally, use of benzoyl peroxide and glacial acetic acid permits use of reaction times at lower end of the indicated range; the reaction temperature must usually be at least 50° C. when no benzoyl peroxide is used. | 20°–80° C. | 1.5–16 hrs. | Glacial acetic acid or HC such as benzene | — |
| CF (Hydrolysis) | 1–6 equivalents or, when ImA contains one or more —COOR$_{18}$ groups, 0.95–1 equivalent of a base, pref. sodium hydroxide or potassium hydroxide, per mole LXXVI and, if a mixture is obtained, separate the desired product from the mixture. | 0°–50° C., pref. 0°–5° C. when ImA contains one or more —COOR$_{18}$ groups and otherwise 20°–50° C. | 2–24 hrs. | Same as AA | — |
| CG (Oxidation) | 5–60 moles, pref. 10–40 moles, manganese dioxide, pref. activated manganese dioxide, or 2–4 moles N—methylmorpholine-N—oxide monohydrate and catalytic amount (e.g., 0.02–0.05 mole) of ((C$_6$H$_5$)$_3$P)$_3$RuCl$_2$ (tris-(triphenylphosphine)ruthenium(II) chloride) per mole LXXVII. | 20° C.-reflux, pref. reflux, esp. refluxing toluene with manganese dioxide and 20°–25° C. with N—methylmorpholine N—oxide monohydrate | 1 hr.–9 days, pref. 1–16 hrs. in refluxing toluene, with manganese dioxide and pref. 10–18 hrs. with N—methylmorpholine N—oxide monohydrate | AIO, pref. HC or ES, esp. toluene, diethyl ether or THF or mixture of diethyl ether and THF with manganese dioxide and dry acetone with N—methylmorpholine-N—oxide monohydrate | Yes with N—methylmorpholine N—oxide monohydrate |
| CH (Wittig) | (1) Synthesis of ylide: 1–1.05 moles strong base, e.g., sodium hydride, phenyllithium or, pref., n-butyllithium per mole LXXIX. Pref, slowly add solution of strong base to solution of LXXVIII.<br>(2) Synthesis of enol ether: Ylide from 1–1.05 moles LXXIX per mole LXXVIII.<br>(3) Hydrolysis of enol ether: Large molar excess, e.g., 2–20 moles, strong acid, e.g., 70% perchloric acid, per mole LXXVIII used in Step 2. | −40°–0° C., pref. −35°–−20° C.<br><br>−30°–0° C., pref. −20°–0° C.<br>0°–30° C. | 1–4 hrs.<br><br>1–4 hrs.<br>8–24 hrs. | AIO, pref. ES, e.g., THF<br><br>Same as Step 1<br>Mixture of aqueous acid and ES, e.g., mixture of 70% perchloric acid and THF | Yes<br><br>Yes<br>— |
| CI (Wittig) | Same as Reaction CH (Molar quantities in Steps 2 and 3 are per mole LXXX). | Same as CH | Same as CH | Same as CH | Same as CH |
| CJ (Wittig) | Same as Reaction CH (Molar quantities in Steps 2 and 3 are per mole LXXXI). | Same as CH | Same as CH | Same as CH | Same as CH |
| CK (Wittig) | Alternative a:<br>1–2 moles, pref. 1.1–1.7 moles, LXXXIII per mole LXXXII.<br>Alternative b:<br>(1) Synthesis of ylide: 1–1.08 moles strong base, pref. sodium hydride, per mole LXXXIV. If necessary to initiate the | 80° C.-reflux, esp. refluxing toluene<br><br>−20°–25° C., pref. −20°–0° C. | 6–18 hrs.<br><br>1–2 hrs. | AIO, pref. HC, esp. toluene<br><br>AIO, pref. ES, esp. THF | Yes<br><br>Yes |

-continued

| Reaction/Type | Reagents, Molar Ratios and Comments | Temperature | Time | Solvent | Inert Atmosphere |
|---|---|---|---|---|---|
| | reaction, add small amount of sodium hydride in THF stirred at 20°–25° C., cool to −20°–0° C. once the reaction commences and complete the addition and reaction at −20°–0° C. (2) 1–1.25 moles ylide from LXXXIV (assuming 100% conversion of LXXXIV to ylide) per mole LXXVIII. Add solution of LXXVIII to ylide solution at −20°–0° C., allow to warm to 20°–25° C. and stir at this temperature for balance of reaction time. (3) Quench with, for example, saturated aqueous ammonium chloride solution. | −20°–25° C. | 3–18 hrs. | Same as Step 1 | Yes |
| CL (Reduction) | (1) At least 2 equivalents of transferable hydride from a metal hydride reducing agent, e.g., lithium aluminum hydride or diisobutylaluminum hydride, per mole LXXXV, pref. 3.8–6 moles diisobutylaluminum hydride per mole LXXXV. When ImA contains one of more —COOR$_{18}$ groups, use just 2 equivalents of transferable hydride per mole LXXXV and separate the desired product from the resulting mixture (after Step 2). (2) Quench with, for example, water or saturated aqueous ammonium chloride solution. | −20°–25° C. −10°–25° C., pref. −10°–10° C. | 1–5 min. 0.7–4 hrs., pref. 2–3 hrs. | — AIO, pref. ES, e.g., THF, or mixture of THF and toluene or hexane | — Yes |
| CM (Oxidation) | Same as Reaction CG (Molar quantities are per mole LXXXVI). | 0°–25° C. | 1–5 min. | Same as Step 1 | — |
| CN (Oxidation) | 2–6 moles, pref. 4 moles, potassium persulfate and 1 mole cupric sulfate, pref. cupric sulfate pentahydrate, per mole LXXV. | 20°–40° C. 75°–reflux, pref. 78° C. | 1–24 hrs. 0.25–2 hrs, pref. 0.4–1 hr. | Same as CG Mixture of acetonitrile and water, pref. a 1.67:1 mixture | Yes |
| CO | Alternative a: (p1) Preparation of cis-1-ethoxy-2-tri-n-butylstannylethylene: 1 mole ethoxyacetylene and 1 mole tri-n-butyltin hydride. Add ethoxyacetylene to tri-n-butyltin hydride at 50° C. over 1 hr. period and stir at 50°–55° C. for 3 hrs. and at 60°–70° C. for 1 hr. (p2) Preparation of LXXXVIII: 1–1.08 moles n-butyllithium and 1 mole cis-1-ethoxy-2-tri-n-butylstannylethylene. Add n-butyllithium solution dropwise to solution of stannyl compound at −78° C. | 50°–55° C. for 4 hrs. and 60°–70° C. for 1 hr. −80°–−75° C. | 5 hrs. 1–3 hrs., pref. 2 hrs. | Neat AIO, e.g., ES, pref. THF | Yes Yes |
| | Alternative b: (p) Preparation of LXXXVIII: 2–2.1 moles, pref. 2 moles, t-butyllithium, pref. as 1–2 M. solution in pentane, and 1 mole 1-bromo-2-ethoxyethylene. | −80°–−75° C. | 1–3 hrs., pref. 2 hrs. | Same as Step (p2) | — |
| (Addition) | (1) 1–1.75 moles LXXXVIII (assuming 100% | −80°–−40° C., | 1–8 hrs, | Same as Step (p2) | Yes |

-continued

| Reaction/Type | Reagents, Molar Ratios and Comments | Temperature | Time | Solvent | Inert Atmosphere |
|---|---|---|---|---|---|
| CO (Hydrolysis) (Cont'd) | yield from Step p or p2) per mole LXXVIII. Crude enol ether product of this step may be used in next step without isolation and/or purification but isolation and purification of enol ether intermediate may improve yield of LXXXVII from next step. | pref. $-80°$ – $-60°$ C. | pref. 1.5–5 hrs. | | — |
| | (2) Catalytic amount of p-toluenesulfonic acid or monohydrate thereof (e.g., 0.5–2 g, pref. 1.2–1.8 g., per mole LXXVIII used in Step 1) and water. | $20°$–$40°$ C., pref. $20°$–$25°$ C. | 0.5–5 hrs., pref. 0.5–4 hrs. | Mixture of ES and water, pref. mixture of THF and water | — |
| CP | 1–1.3 moles LXXIII and catalytic amount of acid, e.g., 0.5–2 g., pref. 1 g., p-toluenesulfonic acid or monohydrate thereof, per mole LXXII. | $160°$ C.-reflux, pref. $160°$–$180°$ C. | 4–48 hrs. | High boiling HC, esp. mesitylene | — |
| DA (Halogenation) | 1.4–8 moles thionyl chloride per mole LXXVII. | $0°$–$80°$ C. | 2–24 hrs. | Neat | — |
| DB | Excess triphenylphosphine, e.g., 2–10 moles per mole XCI. | $60°$ C.-reflux, pref. $\leq 150°$ C., esp. $75°$–$78°$ C. (in absolute ethanol) | 0.5–24 hrs. | AIO, pref. absolute ethanol | Yes |
| DC | Alternative a: 1–1.1 moles XCIV per mole XCI. Can use excess XCIV as the solvent. | $20°$–$140°$ C., usually $110°$–$140°$ C. | 6–24 hrs., usually 10–16 hrs. | HC, e.g., benzene or xylene or neat (excess is solvent) | Yes |
| | Alternative b: (1) 2.3–2.35 moles XCIIIA per mole XCI to be used in Step 2 and 1.05–1.1 moles strong base, pref. sodium hydride, per mole XCIIIA. | $15°$–$25°$ C. | 1–2 hrs. | AIO, pref. ES, esp. THF | Yes |
| | (2) Add XCI. | $20°$–$30°$ C. | 10–24 hrs. | Same as Step 1 | Yes |
| | (3) Quench with, e.g., water. | $20°$–$25°$ | 1–5 min. | — | — |
| DD | Same as Reaction J, Alternative a (Molar quantities are per mole LXXX). | Same as J, a | Same as J, a | Same as J, a | Yes |
| DE (Halogenation) | Same as Reaction DA (Molar quantities are per mole XCV). | Same as DA | Same as DA | Same as DA | — |
| DF | Same as Reaction DB (Molar quantities are per mole XCVI). | Same as DB | Same as DB | Same as DB | Yes |
| DG | Same as Reaction DC (Molar quantities are per mole XCVI). | Same as DC | Same as DC | Same as DC | Yes |
| DH | (1) Combine 11. saturated aqueous ammonium hydroxide, 1.9–2.1 moles lithium chloride, 5.9–6.1 moles potassium hydroxide and 1–1.02 moles benzyltriethylammonium chloride per mole XCIX to be used in Step 3. See Step 1 of Example 3. | $20°$–$25°$ C. | — | Mixture of water and HLA, pref. methylene chloride | Yes |
| | (2) Bubble in ammonia for 30 min. | $0°$ C. | 30 min. | Same as Step 1 | Yes |
| | (3) Add XCIX and additional gaseous ammonia portionwise over period of 1 hr. | $0°$ C. | 1 hr. | Same as Step 1; pref. mixture of water, methylene chloride and chloroform | Yes |
| | (4) Bubble in additional ammonia for 5 hrs. | $0°$ C. | 5 hrs. | Same as Step 3 | Yes |
| | (5) Stir. | $20°$–$25°$ C. | 8–24 hrs. | Same as Step 3 | Yes |

-continued

| Reaction/Type | Reagents, Molar Ratios and Comments | Temperature | Time | Solvent | Inert Atmosphere |
|---|---|---|---|---|---|
| | (6) Acidify to pH 6.5 with, for example, concentrated hydrochloric acid. Product (C) is racemic. | 20°–25° C. | 1–5 min. | Water | — |
| DI (Reduction) | Same as Reaction J, Alternative a (Molar quantities are per mole LXXVIII). | Same as J, a | Same as J, a | Same as J, a or mixture of ES and lower alkanol, esp. 1:1 mixture of THF and methanol | Yes |

In the preceding table,

AIO = anhydrous inert organic solvent
ES = ether solvent, for example, diethyl ether, 1,2-diethoxyethane, 1,2-dimethoxyethane, tetrahydrofuran, dioxane and mixtures thereof
esp. = especially
HC = hydrocarbon solvent, for example, benzene, toluene, xylene and mixtures thereof
HLA = halogenated lower alkane solvent, for example, carbon tetrachloride, chloroform, 1,1-dichloroethane, 1,2-dichloroethane, methylene chloride and 1,1,2-trichloroethane, usually preferably methylene chloride
hr. (hrs.) = hour(s)
IO = inert organic solvent
min. = minutes
pref. = preferably, preferred
THF = tetrahydrofuran Most of the molar amounts (ratios) given in the preceding table are merely exemplary and may be varied, as is evident to one of ordinary skill in the art. For example, in a reaction of two compounds one of which is readily available and one of which isn't, an excess of the readily available compound may be used to drive the reaction further towards completion (unless the use of an excess would increase the synthesis of an undesired compound).

Likewise, most of the temperature ranges given in the preceding table are merely exemplary, and it is within the ability of one of ordinary skill in the art to vary those that are not critical.

The reaction times set forth in the preceding table are also merely exemplary and may be varied. As is well-known, the reaction time is often inversely related to the reaction temperature. Generally, each reaction is monitored by, for example, thin layer chromatography and is terminated when at least one starting material is no longer present, when it appears that no more of the desired product is being formed, etc.

Conventional work-up procedures have generally been omitted from the preceding table.

As utilized in the preceding table, the term "solvent" embraces mixtures of solvents and implies that the reaction medium is a liquid at the desired reaction temperature. It should, therefore, be understood that not all of the solvents listed for a particular reaction may be utilized for the entire recited temperature range. It should also be understood that the solvent must be at least substantially inert to the reactants employed, intermediates generated and end products under the reaction conditions utilized.

The term "inert atmosphere", as utilized in the preceding table, means an atmosphere that does not react with any of the reactants, intermediates or end products or otherwise interfere with the reaction. While a carbon dioxide atmosphere is suitable for certain reactions, the inert atmosphere is usually nitrogen, helium, neon, argon or krypton, or a mixture thereof, and most often dry nitrogen to maintain anhydrous conditions. Most reactions, including those where the use of an inert atmosphere is not specified, are carried out under an inert atmosphere, usually dry nitrogen, for convenience.

In the preceding table, n-butyllithium is preferably employed as a 1.3–1.7M. solution in hexane, and lithium diisopropylamide is preferably prepared in situ from n-butyllithium and diisopropylamine.

Reactions analogous to many of the reactions of this specification are described in detail in copending application Ser. No. 06/722,288, filed by Faizulla G. Kathawala on Apr. 11, 1985 and titled Indole Analogs of Mevalonolactone and Derivatives Thereof. These reactions may be carried out analogously to the corresponding reactions of said application. Said application, particularly pages 14–26, 28–52, 65–76, 82–96, 98–102, 106, 107 and 116–122 thereof, is hereby incorporated by reference. Generally, where the reaction conditions set forth in said application differ from those set forth in this specification, the reaction conditions set forth in said application may also be utilized for the compounds of this invention.

Reactions analogous to many of the reactions of this specification are also described in U.S. Pat. No. 4,613,610. Said patent, particularly columns 6–48 and 55–82 thereof, is hereby incorporated by reference. Generally, where the reaction conditions set forth in said patent differ from those set forth in this specification, the reaction conditions set forth in said patent may also be utilized for the compounds of this invention.

The product of each reaction may, if desired, be purified by conventional techniques such as recrystallization (if a solid), column chromatography, preparative thin layer chromatography, gas chromatography (if sufficiently volatile), fractional distillation under high vacuum (if sufficiently volatile) or high pressure (performance) liquid chromatography (HPLC). Often, however, the crude product of one reaction may be employed in the following reaction without purification.

Some of the reactions described above may yield mixtures of two or more products only one of which leads to the desired compound of Formula I. For example, Reaction CE may yield mixtures when, for example, at least one of $R_{1a}$, $R_{3a}$ and $R_4$–$R_{12}$ is primary or secondary alkyl, particularly methyl. Any obtained mixture may be separated by conventional techniques such as those set forth in the preceding paragraph.

The reactions disclosed above may be utilized to synthesize compounds of Formula I having an $R_{14}$ group and one or more $R_{17}$ groups or no $R_{14}$ group and two or more $R_{17}$ groups wherein the $R_{14}$ and/or $R_{17}$ groups are different. However, mixtures, from which the desired compound may be isolated by conventional means, such as those set forth above, are usually obtained.

It is, however, sometimes possible to increase the selectivity in, for example, Reactions AA, BB and BJ by utilizing therein compounds wherein the $R_{16}$ or $R_{16}'$ and/or $R_{18}$ group(s) to be hydrolyzed differ from each such group to be retained.

It is often preferable to synthesize compounds of Formula I having two or more different $R_{14}$ and/or $R_{17}$ groups (and sometimes other compounds of Formula I) by modifying the processes set forth above. For example, one can synthesize compounds of Formulae XXVIII, XLVIII and LXII having in lieu of $R_{16}$ or $R_{16}'$ and/or one or more $R_{18}$ groups other ester groups that may be hydrolyzed under conditions that do not affect the $R_{16}$, $R_{16}'$ and $R_{18}$ groups that are present and that are stable to the reaction conditions utilized to synthesize the compounds. For example, to synthesize a compound of Formula XXIX wherein ImB contains one or more —COOR$_{18}$ groups and no —COO$^{\ominus}$ M$_2^{\oplus}$ groups or a compound of Formula XXIX or XXX wherein ImB or ImC, as the case may be, contains one or two —COOR$_{18}$ groups and one —COO$^\ominus$ M$_2^\oplus$ group or one of the former and two of the latter, one can utilize the processes set forth for the synthesis of the compounds of Formula XXVIII to synthesize a corresponding compound having, in lieu of each R$_{16}'$ and/or R$_{18}$ group to be hydrolyzed, a group that may be cleaved by conditions that do not affect the R$_{16}'$ and/or R$_{18}$ group(s) to be retained, cleave said group(s) under said conditions (rather than those of Reaction AA) and, if necessary, utilize the processes set forth above to convert one or more carboxy groups into salt form. Examples of ester groups that may be cleaved without affecting some or all of the R$_{16}'$ and/or R$_{18}$ groups present are trityl, 2,2,2-trichloroethyl and allyl. It is well within the ability of one of ordinary skill in the art to synthesize compounds corresponding to those of Formulae XXVIII, LXII, etc. but having, in lieu of one or more R$_{16}$,R$_{16}'$ and/or R$_{18}$ groups, groups cleavable by conditions that do not affect the R$_{16}$, R$_{16}'$ and/or R$_{18}$ groups and to utilize said conditions to cleave said groups.

As between Reactions CE, CF and CG, on the one hand, and Reaction CN, on the other, Reaction CN is usually preferred, particularly when ImA contains one or more —COOR$_{18}$ groups, since —COOR$_{18}$ groups may be hydrolyzed by the reaction conditions utilized in Reaction CF. As between Reactions CK, CL and CM, on the one hand, and Reaction CO, on the other, Reaction CO is usually preferred, particularly when ImA contains one or more —COOR$_{18}$ groups, because —COOR$_{18}$ groups may be reduced by the reaction conditions utilized in Reaction CL.

The compounds of Formulae IV, X, XVI, XIX, XXI, XXII, XXIV, XXVI, XXXII, XLII, LV, LX, LXI, LXVIII-LXXI, LXXIII, LXXIX, LXXXIII, LXXXIV, LXXXVIII, XCIII and XCIX and the reagents not designated by a Roman number are known or, if unknown, may be synthesized by processes analogous to those described in the literature for similar known compounds. For example: (1) The compound of Formula IV is disclosed in World (P.C.T.) Published Patent Application No. 86/00307 See also columns 19, 20, 38-41 and 60 of U.S. Pat. No. 4,613,610, which are hereby incorporated by reference, U.S. Pat. No. 4,625,039 which patent, particularly columns 9-16 thereof, is also hereby incorporated by reference and columns 16-18 and 31-33 of U.S. Pat. No. 4,668,794, which are also hereby incorporated by reference. (2) Compounds of Formula X are also disclosed in World (P.C.T.) Published Patent Application No. 86/00307. See also columns 20-22, 42-44 and 70 of U.S. Pat. No. 4,613,610, which are hereby incorporated by reference, U.S. Pat. No. 4,650,890, which patent, particularly columns 9-11 thereof, is hereby incorporated by reference, and columns 18 and 33-35 of U.S. Pat. No. 4,668,794, which are also hereby incorporated by reference. A preferred process for the synthesis of the erythro racemate of the compound of Formula X wherein R$_{13}$ is hydrogen, R$_{16}'$ is methyl, and X$_4$ is a direct bond is disclosed in Kapa, Tetrahedron Letters 25, 2435-2438 (1984). The other compounds of Formula X wherein R$_{13}$ is hydrogen, and X$_4$ is a direct bond in racemic erythro form may be synthesized similarly. See also U.S. Pat. No. 4,571,428, which is also hereby incorporated by reference. A preferred process for the synthesis of the 3R,5S isomer of the compound of Formula X wherein R$_{13}$ is hydrogen, R$_{16}'$ is t-butyl, and X$_4$ is a direct bond is disclosed in Example A of this specification. The other compounds of Formula X wherein R$_{13}$ is hydrogen, and X$_4$ is a direct bond in 3R,5S form may be synthesized analogously or from the t-butyl ester by hydrolysis and esterification of the resulting carboxylic acid. Another process for the synthesis of the compounds of Formula X wherein R$_{13}$ is hydrogen, and X$_4$ is a direct bond in 3R,5S form is disclosed in U.S. Pat. No. 4,677,211, which is hereby incorporated by reference.

A preferred process for the synthesis of the compounds of Formula LXVIII wherein R$_{1a}$ is R$_{1r}$, particularly those not containing any —COOR$_{18}$ groups, is disclosed in Reaction Scheme VII.

As is evident to those in the art, each compound of Formula I wherein Z is a group of Formula c (including those of Formulae XLVIII-LI, LIII, LIV, LVI-LVIX, LXII-LXVI, etc.) and the pharmaceutically acceptable acid addition salts thereof, and Formulae XVII, XX and XXIII has a single center of asymmetry and, therefore, may be resolved into two optically active isomers. When a compound of Formula XVII or XXIII is converted into a compound of Formula XVIII or XXV, respectively, an additional center of asymmetry is generated. Consequently, when a racemic compound of Formula XVII or XXIII is utilized, four stereoisomers (two pairs of diastereoisomers) of the resulting compound of Formula XVIII or XXV are formed, whereas when an optically pure compound of Formula XVII or XXIII is utilized, two diastereoisomers of the compound of Formula XVIII or XXV are formed. The center of asymmetry of each compound of Formulae LXVIII, LXXI, LXXII, LXXIV, etc. may be ignored since it is destroyed in Reaction CD.

The compounds of Formula I wherein Z is a group of Formula a or b (including those of Formulae XII, XIV, XVIII, XXVII-XXXI, XXXIII-XXXVI, etc.) the pharmaceutically acceptable acid addition salts thereof, and Formulae X, XI, XIII and XXV have two centers of asymmetry and, therefore, may exist in four stereoisomeric forms. Except where the compound is formed from an optically pure precursor already having both chiral carbon atoms or where the reaction involves the use of a stereospecific reagent that gives an optically pure product, the compound is obtained as a mixture of two (if formed from an optically pure compound having one center of asymmetry) or four (if formed from a racemic compound having one center of asymmetry) stereoisomers.

The obtained mixtures of stereoisomers may be separated by conventional means. For example, diastereoisomers may be separated by fractional crystallization, column chromatography, preparative thin layer chromatography and HPLC. Each mixture of four stereoisomers of a compound of Formula XXXV may, for example, be separated by HPLC into its cis and trans (lactone) components, each of which is a racemate that may be resolved into two optically active enantiomers.

Techniques for separating a racemate into its two optically active enantiomers are known. For example, a racemic compound having a carboxylic acid group may be reacted with an optically pure organic base having at least one center of asymmetry to form a mixture of diastereoisomeric salts that may be separated by fractional crystallization, column chromatography, etc. or it may be reacted with an optically pure alcohol having at least one center of asymmetry to form a mixture of diastereoisomeric esters which may be separated by conventional techniques such as those set forth above or below. Likewise, a racemic compound having a carboxylic acid, acyl halide, ester or lactone group may be reacted with an optically pure organic base, i.e., an amine, to form a mixture of diastereoisomeric amides that may be separated by conventional means, e.g., fractional crystallization, column chromatography and/or HPLC. For example, a racemic lactone of Formula XXXV may be reacted with an excess of R-(+)-α-methylbenzylamine (or the corresponding S-(−) compound) to form a mixture of two diastereoisomeric α-methylbenzylamides which may be separated by, for example, column chromatography on a silica gel column and/or by HPLC using a Partisil column. Often it is desirable to utilize both techniques, i.e., to partially separate the diastereoisomers by column chromatography and to purify each fraction by HPLC. Typically, the α-methylbenzylamides are synthesized by reacting the racemic lactone with a large molar excess of the amine at 20°–25° C. for 16–24 hours. The reaction is run neat, with the excess amine serving as the solvent. After the reaction, the excess amine is removed by vacuum distillation at 25°–35° C. After separation, each chiral amide may be hydrolyzed to the corresponding, for example, sodium, salt by, for example, refluxing with 1.5–3, preferably 2–2.2, equivalents of a base such as sodium hydroxide for 5–25 hours in a mixture of water and ethanol. The resulting salts may be converted to the corresponding free acids, esters, lactones and other salts by conventional means such as the reactions set forth in Reaction Scheme IV. On the other hand, a racemic compound having a hydroxy group may be esterified with an optically pure carboxylic acid having at least one center of asymmetry to form a mixture of diastereoisomeric esters or it may be reacted with an optically pure trisubstituted silyl halide, e.g., (−)-α-naphthylphenylmethylchlorosilane (Sommer et al., J. Am. Chem. Soc. 80, 3271 (1958).), to form a mixture of two diastereoisomeric silyloxy compounds, which mixture may be separated by conventional techniques. For example, diastereoisomeric (−)-α-naphthylphenylmethylsilyl derivatives of a lactone of Formula XXXV may be separated on a silica column having covalently bound L-phenylglycine. After separation, the optically pure salts, amides, esters or silyloxy compounds are reconverted to the corresponding carboxy groupor hydroxy group-containing compounds with retention of optical purity. For example, the process conditions disclosed for Reactions B, D, F and H may be utilized to cleave (−)-α-naphthylphenylmethylsilyl and other silyl groups. The presence of one or more interfering groups may dictate which resolution procedure is preferred.

Since any compound of Formula I wherein Z is a group of Formula a or c wherein $R_{14}$ is a cation other than M may be converted into the corresponding compound wherein $R_{14}$ is hydrogen, M or $R_{16}$ by the processes of Reaction Schemes IV and V, the compounds of Formula I wherein Z is a group of Formula a or c and $R_{14}$ is a pharmaceutically unacceptable cation are also within the scope of this invention since they are useful as intermediates. However, such compounds are not compounds of Formula I as utilized in this specification, except where indicated to the contrary.

Also within the scope of this invention are the intermediates of Formulae II, V, VII, XI, XIII, XV, XVII, XX, XXIII, XXV, LXXXV and LXXXVI. The preferences for each variable are the same as those set forth for the compounds of Formula I, with the preferred groups of such compounds including those that correspond to Groups (xxv)-(xxviii), (xciii)-(xcvi), (clxi)-(clxiv) and (ccxxix)-(ccxxxii) (for Formulae V and VII) and Groups (i)-(xxiv), (lxix)-(xcii), (cxxxvii)-(clx) and (ccv)-(ccxxviii) for each of the other formulae) to the extent consistent therewith.

The entire specification of U.S. Pat. No. 4,668,794, particularly columns 1-23 and 40-42 and especially columns 1-6, is hereby incorporated by reference as if set forth herein in its entirety.

Besides having the utility set forth below, every compound of Formula I is useful as an intermediate in the synthesis of one or more other compounds of Formula I utilizing the reactions set forth in Reaction Schemes IV and V.

The compounds of Formula I and the pharmaceutically acceptable acid addition salts thereof are competitive inhibitors of 3-hydroxy-3-methylglutaryl coenzyme A (HMG-CoA) reductase, the rate limiting enzyme in cholesterol biosynthesis, and, therefore, they are inhibitors of cholesterol biosynthesis. Their biological activity may be demonstrated in the following two tests:

Test A. In Vitro Microsomal Assay of HMG—CoA Reductase Inhibition:

200 μl. aliquots (1.08–1.50 mg./ml.) of rat liver microsomal suspensions, freshly prepared from male Sprague-Dawley rats (150–225 g. body weight), in Buffer A with 10 mmol. dithiothreitol are incubated with 10 μl. of a solution of the test substance in dimethylacetamide and assayed for HMG—CoA reductase activity as described in Ackerman et al., J. Lipid Res. 18, 408–413 (1977), the concentration of the test substance in the assay system being 0.0001–2,000 μmolar. In the assay the microsomes are the source of the HMG-CoA reductase enzyme which catalyzes the reduction of HMG-CoA to mevalonate. The assay employs a chloroform extraction to separate the product, [$^{14}$C]mevalonolactone, formed by the HMG-CoA reductase reduction of the substrate, [$^{14}$C]HMG-CoA. [$^{3}$H]mevalonolactone is added as an internal reference. Inhibition of HMG-CoA reductase is calculated from the decrease in specific activity ([$^{14}$C/$^{3}$H]mevalonate) of test groups compared to controls.

The $IC_{50}$ is the concentration of the test substance in the assay system calculated or observed to produce a 50% inhibition of HMG-CoA reductase activity.

Test B. In Vivo Cholesterol Biosynthesis Inhibition Test:

In vivo studies utilize male Wistar Royal Hart rats weighing 150±20 g. which have been kept for 7–10 days on an altered light cycle (6:30 A.M. - 6:30 P.M. dark) housed two per cage and fed powdered Purina Rat Chow and water ad libitum. Three hours before the diurnal maximum of cholesterol synthesis at mid-dark, the rats are administered orally the test substance (e.g., 0.001–200 mg./kg. body weight) dissolved or as a suspension in 0.5% carboxymethylcellulose in a volume of 1 ml./100 g. body weight. Controls receive vehicle alone. One hour after receiving the test substance (or the vehicle alone), the rats are injected intraperitoneally with about 25 μCi/100 g. body weight of sodium [1-$^{14}$C]acetate 1-3 mCi/mmol. Two hours after mid-dark, blood samples are obtained under sodium hexobarbitol anesthesia, and the serum is separated by centrifugation.

Serum samples are saponified and neutralized, and the 3β-hydroxysterols are precipitated with digitonin basically as described in Sperry et al., J. Biol. Chem. 187, 97 (1950). The [$^{14}$C]digitonides are then counted by liquid scintillation spectrometry. After correcting for efficiencies, the results are calculated in nCi (nanocuries) of 3β-hydroxysterol formed per 100 ml. of serum. Inhibition of 3β-hydroxysterol synthesis is calculated from the reduction in the nCi of 3β-hydroxysterols formed from test groups compared to controls.

the $ED_{50}$ is the dose of the test substance calculated or observed to produce a 50% inhibition of 3β-hydroxysterol synthesis.

Since they inhibit cholesterol biosynthesis, the compounds of Formula I and the pharmaceutically acceptable acid addition salts thereof (including those of each subgroup thereof) are useful for lowering the blood cholesterol level in animals, e.g., mammals, especially larger primates, in particular humans, and, therefore, as hypolipoproteinemic and anti-atherosclerotic agents.

The precise dosage of the compound of Formula I or the pharmaceutically acceptable acid addition salt thereof to be employed for inhibiting cholesterol biosynthesis depends upon several factors including the host, the nature and the severity of the condition being treated, the mode of administration and the particular active substance employed. However, in general, suitable oral daily dosages of the compounds of Formula I and the pharmaceutically acceptable acid addition salts thereof for the satisfactory inhibition or reduction of cholesterol biosynthesis (i.e., the satisfactory reduction of the blood cholesterol level and satisfactory treatment of hyperlipoproteinemia and atherosclerosis) are indicated to be 0.002–100 mg./kg. body weight, e.g., 0.002–10 mg./kg. body weight for the more active compounds. For most larger primates such as humans, a suitable oral daily dosage is indicated to be 0.1–2,000 mg., e.g., 0.1–200 mg. for the more active compounds. For administration by injection, a dosage somewhat lower than would be used for oral administration of the same active substance to the same host having the same condition is usually employed. However, the above dosages are also typically used for i.v. administration.

The daily dosage may be administered in a single dose but more typically is administered in two to four equal portions, typical doses being 0.025–2,000 mg. Often, a small dosage is administered initially, and the dosage is gradually increased until the optimal dosage for the host under treatment is determined.

A typical dosage unit for oral administration may contain 0.025–500 mg. of a compound of Formula I or a pharmaceutically acceptable acid addition salt thereof.

The compounds of Formula I and the pharmaceutically acceptable acid addition salts thereof may be formulated into conventional pharmaceutical compositions and administered by any conventional mode of administration, in particular enterally, e.g., in the form of capsules or tablets, or parenterally, e.g., in the form of sterile injectable solutions or suspensions. The pharmaceutical compositions comprise a compound of Formula I or a pharmaceutically acceptable acid addition salt thereof and at least one pharmaceutically acceptable solid or liquid carrier (or diluent). They may be formulated in conventional manner. The compounds and pharmaceutically acceptable acid addition salts of each subgroup thereof may likewise be formulated into such pharmaceutical compositions and administered by such routes.

The compounds of Formula I and the pharmaceutically acceptable acid addition salts thereof (including those of each subgroup thereof) may be formulated into such pharmaceutical compositions containing an amount of the active substance that is effective for inhibiting cholesterol biosynthesis in unit dosage form and such compositions comprising at least one solid pharmaceutically acceptable carrier.

The compound of Example 2 exhibited an $IC_{50}$ in Test A of 0.0026 μmolar, that of Example 2A, the preferred compound of this invention, exhibited an $IC_{50}$ of 0.002 μmolar in this test, and that of Example 10 exhibited an $IC_{50}$ of 0.036 μmolar in this test whereas that of Compactin was 1.01 μmolar and that of Mevinolin was 0.14 μmolar in this test. Other tested compounds of this invention exhibited $IC_{50}$'s of 0.005→10 μmolar in this test. In Test B the compound of Example 2 exhibited an $ED_{50}$ of 0.025 mg./kg., that of Example 2A exhibited an $ED_{50}$ of 0.02 mg./kg., and that of Example 10 exhibited an $ED_{50}$ of 0.028 mg./kg. whereas that of Compactin was 3.5 mg./kg. and that of Mevinolin was 0.38 mg./kg. Other tested compounds of this invention exhibited $ED_{50}$'s of 0.045–0.26 mg./kg. in this test. The daily dosage for the compounds of Examples 2 and 2A is, therefore, indicated to be 0.1–50 mg., e.g., 1–20 mg., preferably 0.2–10 mg., especially 0.5–2 mg., for most larger primates such as humans. The daily dosage for the compound of Example 10 for most larger primates such as humans is indicated to be about 10% higher than that of Examples 2 and 2A.

Representative formulations suitable for encapsulation in a hard gelatin capsule by conventional techniques are:

| | | |
|---|---|---|
| A. | Compound of Formula I, e.g., the compound of Example 2 | 5 mg. |
| | Corn starch | 244 mg. |
| | Magnesium stearate | 1 mg. |
| B. | Compound of Formula I, e.g., the compound of Example 2 | 1 mg. |
| | Corn starch | 248 mg. |
| | Magnesium stearate | 1 mg. |
| C. | Compound of Formula I, e.g. the compound of Example 2A | 0.5 mg. |
| | Corn starch | 248.5 mg. |
| | Magnesium stearate | 1 mg. |

The following examples show representative compounds encompassed by this invention and their synthesis. However, it should be understood that they are for purposes of illustration only.

EXAMPLE 1

Ethyl (±)-erythro-(E)-3,5-dihydroxy-7-1,'-(4''-fluorophenyl)-4'-(1''-methylethyl)-2'-phenyl-1H-imidazol-5'-yl]hept-6-enoate

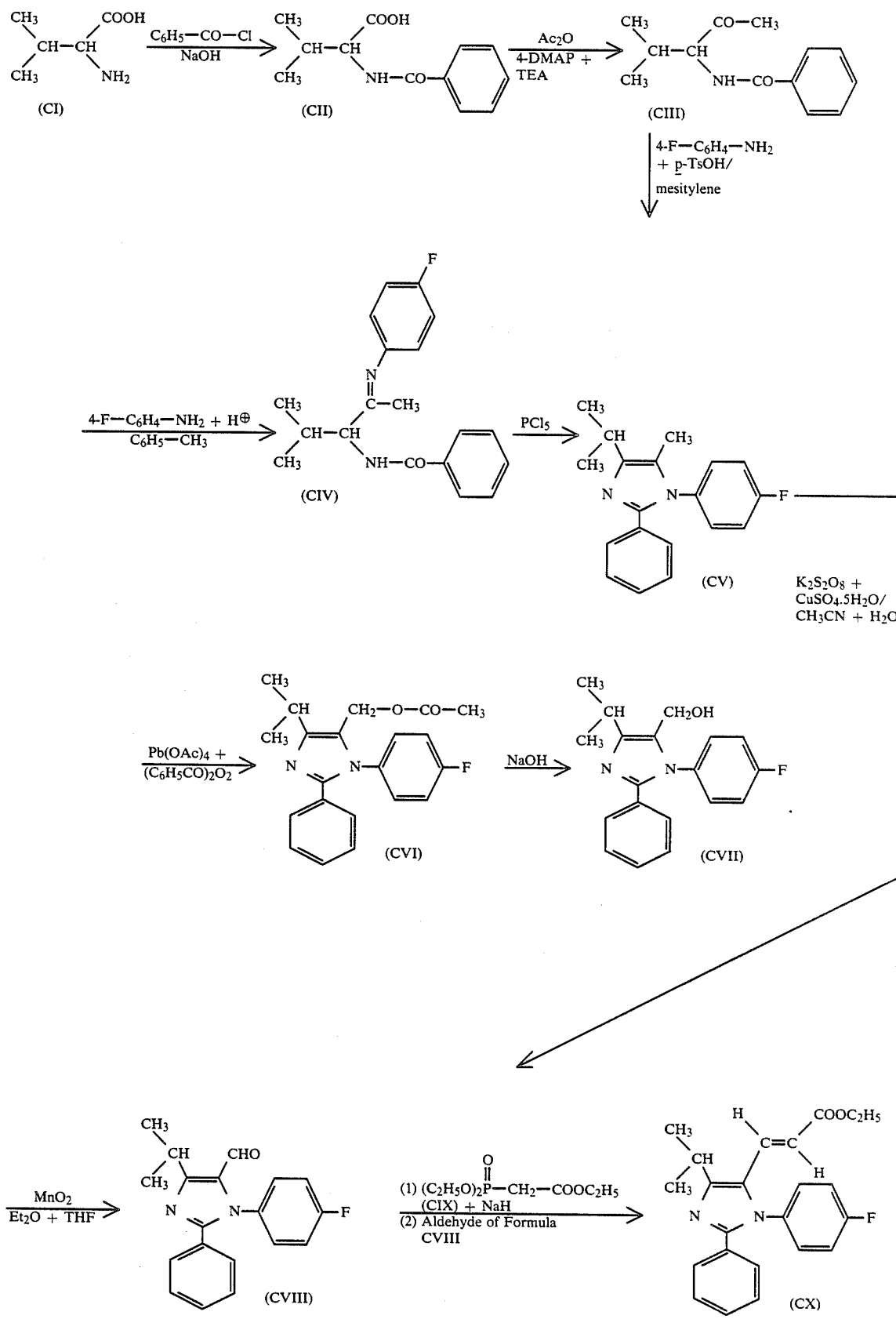

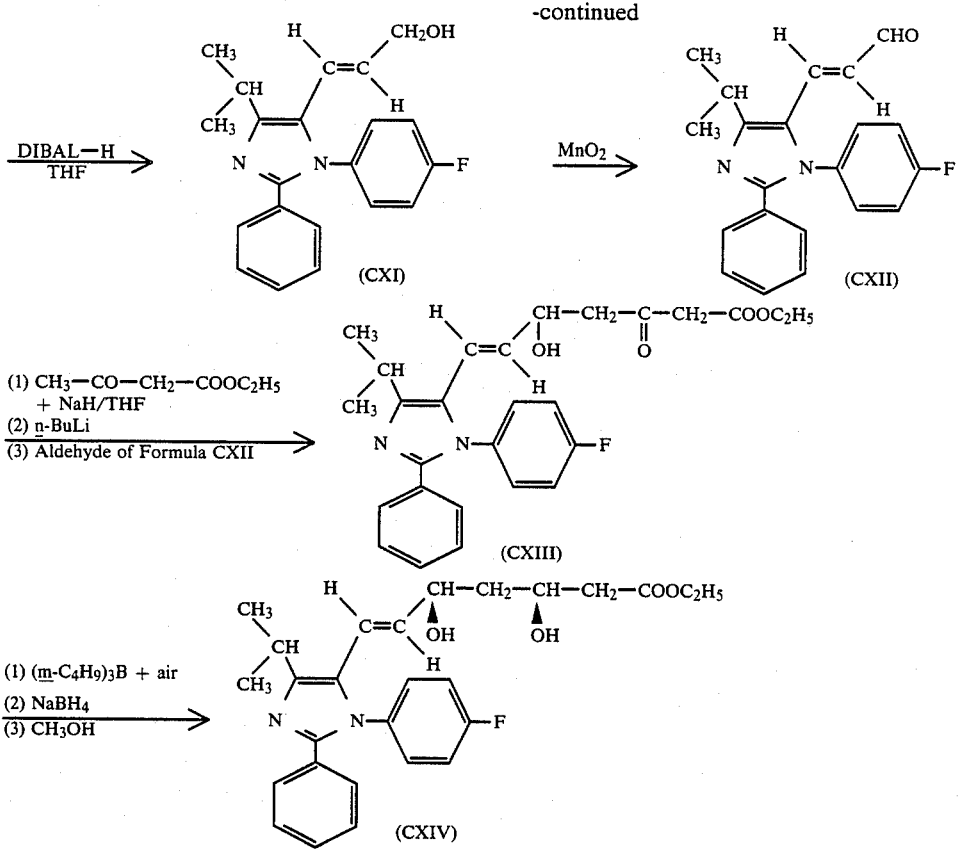

Step 1.

(Reaction CA)

N-Benzoyl-DL-valine (Compound CII)

119 ml. (1.025 moles) of benzoyl chloride and 760 ml. of 2N. sodium hydroxide solution (1.52 moles) are simultaneously added to a mixture of 100 g. (0.854 mole) of DLvaline, 200 ml. of dioxane and 350 ml. of 2N. sodium hydroxide solution (0.7 mole) stirred at 0°-5° C., the additions being at rates such that the pH of the reaction mixture is always basic and the temperature does not exceed 5° C., the reaction being exothermic. The reaction mixture is allowed to warm to 20°-25° C., stirred at 20°-25° C. for 2 hours, cooled to 0° C. and acidified with about 40 ml. of concentrated sulfuric acid. The precipitate is collected by filtration, washed with water, air dried for 16 hours and dissolved in ethyl acetate. The ethyl acetate solution is decanted from some residual water, and petroleum ether is added to obtain a precipitate. The precipitate is subjected to high vacuum for 8 hours to remove some residual dioxane and obtain the product (165.81 g. (88%)), m.p. 125°-128° C. Lit.: 132° C.

Revised procedure:

5.1 kg. (36.28 moles) of benzoyl chloride is added portionwise to a mixture of 3.5 kg. (29.88 moles) of DL-valine, 39.0 l. of 2N. sodium hydroxide solution (78 moles) and 7 l. of tetrahydrofuran stirred at ~10° C. at a rate such that the temperature is maintained at 10°-15° C., and the reaction mixture is warmed to ~20° C. and stirred at ~20° C. for 3 hours, the reaction mixture being stirred under nitrogen throughout. 1.4 l. of concentrated sulfuric acid is carefully added at a rate such that the temperature does not exceed 25° C., and the mixture is cooled to ~5°-10° C. and stirred at this temperature for about 30 minutes to obtain a solid. (If necessary, the mixture is seeded.) The resulting solid is collected by filtration, washed three times with 20 l. portions of hot water, washed three times with 20 l. portions of hexane and dried at 40° C. and reduced pressure for ~12 hours to obtain the product (6.4 kg.), m.p. 123°-126° C.

Step 2

(Reaction CB)

(±)-N-[1-(1'-methylethyl)-2-oxopropyl]benzamide (Compound CIII)

7.4 g. (60.6 mmoles, a catalytic amount) of 4-dimethylaminopyridine is added in two portions to a mixture of 134 g. (0.606 mole) of Compound CII, 172 ml. (185.6 g., 1.818 moles) of acetic anhydride and 169 ml. (122.6 g., 1.212 moles) of triethylamine stirred at 20°-25° C. under nitrogen, and the reaction mixture is stirred at 20°-25° C. under nitrogen for 16 hours, cooled to 0°-5° C. and quenched with 350 ml. of methanol. The mixture is poured into 2 l. of icewater, and the precipitated solid is collected by filtration, washed with about 4 l. of water and allowed to air dry for 16 hours. The resulting brown powder is recrystallized from diethyl ether, and the obtained tan needles are recrystallized from diethyl ether to obtain the product (58.83 g.), m.p. 89.5°-91.5° C. A second crop may be obtained from the combined mother liquors.

Revised procedure:

402 g. (1.82 moles) of Compound CII is added rapidly to 558.3 g. (5.45 moles) of acetic anhydride stirred at 23°–25° C., 368 g. (3.64 moles) of triethylamine is added over a 6 minute period with stirring, the addition being slightly exothermic, the reaction mixture is cooled to 25° C., 22.2 g. (0.18 mole) of 4-dimethylaminopyridine is added over a period of 3 minutes with stirring at 25° C., the reaction mixture is stirred at 25°–28° C. for 2 hours with cooling because the reaction is exothermic, and the reaction mixture is stirred at 22° C. for 16 hours, the reaction mixture being stirred under nitrogen throughout. The reaction mixture is slowly added to a mixture of 3 l. of water and 3 l. of toluene stirred at 20°–25° C. at a rate such that the temperature does not exceed 28° C. The reaction vessel is rinsed with 100 ml. of toluene, and the rinse is combined with the quenched reaction mixture. The organic layer is separated, washed three times with 500 ml. portions of water and filtered through 100 g. of Celite filter aid. The Celite is washed three times with 100 ml. portions of toluene, and the washings are combined with the filtrate. Toluene is distilled at 45° C. and 20–50 mm. Hg until a thick stirrable slurry results, 250 ml. of toluene is added, the mixture is heated at 60° C. to obtain a solution, and the solution is cooled to 4° C. to obtain a yellow solid. The yellow solid is collected by filtration, washed with a cold (5° C.) mixture of 250 ml. of toluene and 250 ml. of heptane, washed with 300 ml. of cold (5° C.) heptane and vacuum dried for 16 hours at 47° C. to obtain the product (294.3 g. (73.9%)), m.p. 90°–92° C.

Step 3

(Reaction CC)

(±)-N-[2-(4′-Fluorophenyl)imino-1-(1′-methylethyl)-propyl]-benzamide (Compound CIV)

A mixture of 72.91 g. (332.5 mmoles) of Compound CIII, 35 ml. (40.63 g., 365.7 mmoles) of 4-fluoroaniline, a catalytic amount (50 mg.) of p-toluenesulfonic acid.-monohydrate and 500 ml. of dry toluene (dried over alumina) is refluxed in a Dean-Stark apparatus for 16 hours under nitrogen, the reaction mixture is allowed to cool, and the toluene is evaporated at reduced pressure to obtain the crude product as a black oil.

Revised procedure:

A mixture of 500 g. (2.28 moles) of Compound CIII, 280 g. (2.52 moles) of 4-fluoroaniline, 2.5 g. (0.013 mole) of p-toluenesulfonic acid monohydrate and 5 l. of toluene is refluxed in a Dean-Stark apparatus for 20 hours under nitrogen, and the reaction mixture is cooled to −10° C. to obtain a cold solution of the crude product.

Step 4

(Reaction CD)

1-(4′-Fluorophenyl)-5-methyl-4-(1′-methylethyl)-2-phenyl-1H-imidazole (Compound CV)

A solution of crude Compound CIV from Step 3, initial procedure (332.5 mmoles assuming 100% yield) in 250 ml. of chloroform is added dropwise to a suspension of 138.5 g. (665 mmoles) of phosphorus pentachloride in 500 ml. of chloroform stirred at −20°–−15° C. under nitrogen. The reaction mixture is allowed to warm to 20°–−25° C. with stirring and stirred at 20°–25° C. for 16 hours, the reaction mixture being maintained under nitrogen throughout. The reaction mixture is quenched with 500 ml. of water and made basic with 10% sodium hydroxide solution. The organic phase is separated, washed twice with saturated sodium chloride solution, dried over anhydrous magnesium sulfate, filtered and concentrated at reduced pressure.

The obtained pale green solid is recrystallized from acetone to obtain the product as white needles (54.83 g.), m.p. 145°–148° C. A 10.83 g. second crop may be obtained from the acetone mother liquor.

Revised procedure:

The cold (−10° C.) solution of crude Compound CIV from Step 3, revised procedure (2.28 moles assuming 100% yield) is diluted with 4 l. of methylene chloride, the dilution being slightly exothermic. 950 g. (4.56 moles) of phosphorus pentachloride is slowly added to the solution stirred at 0° C. at a rate such that the temperature does not exceed 20°–30° C., the addition being exothermic, and the reaction mixture is heated to reflux, refluxed for 2.5 hours and cooled to −15° C., the reaction mixture being stirred under nitrogen throughout. The reaction mixture is slowly poured into a mixture of 8 kg. of ice and 1.83 kg. of 50% sodium hydroxide solution, the temperature of the mixture not being allowed to exceed 30° C. The organic layer is separated and washed with 8 l. of water. The bottom organic layer is separated and filtered, the solvent is distilled at 60° C. and 30–50 mm. Hg to obtain a thick heterogeneous mixture, and 750 ml. of acetone is added at 60° C. The mixture is cooled to 0° C. and maintained at 0° C. for 30 minutes. The resulting off-white solid is collected by filtration, washed three times with 150 ml. portions of cold (10° C.) acetone and vacuum dried at 50° C. to obtain the product (425 g. (64% (Steps 3 and 4 combined))), m.p. 146.5°–148.5° C.

Step 4A (Reaction CP)

1-(4′-Fluorophenyl)-5-methyl-4-(1′-methylethyl)-2-phenyl-1H-imidazole (Compound CV)

A mixture of 657.8 g. (3 moles) of Compound CIII, 400.3 g. (3.60 moles) of 4-fluoroaniline, 3.0 g. (0.016 mole) of p-toluenesulfonic acid.monohydrate and 3.1 l. of mesitylene is refluxed under nitrogen for 4 hours using a Dean-Stark trap to collect 54 ml. of water, 2.4 l. of mesitylene is distilled off at 178°–180° C., and the reaction mixture is refluxed under nitrogen for an additional 44 hours using a Dean-Stark trap to collect another 46 ml. of water and cooled to 60° C. 1.5 l. of acetone is added, and the mixture is cooled to 0°–5° C. and maintained at this temperature for 30 minutes. The resulting off-white solid is collected by filtration, washed three times with 300 ml. portions of cold (5° C.) acetone and vacuum dried to constant weight at 25 mm. Hg and 60° C. for 15 hours to obtain the product (726 g. (82.2%)), m.p. 148°–150° C.

Step 5

(Reaction CE)

5-Acetoxymethyl-1-(4′-fluorophenyl)-4-(1′-methylethyl)-2-phenyl-1H-imidazole (Compound CVI)

A mixture of 21.75 g. (73.9 mmoles) of Compound CV, 65.5 g. (148 mmoles) of lead tetraacetate, 0.05 g. (0.21 mmole) of benzoyl peroxide and 500 ml. of glacial acetic acid is heated at 80° C. for 16 hours under nitrogen, cooled to 0°–5° C. and made basic (pH 8–9) with 10N. sodium hydroxide solution. The resulting suspension is filtered through a pad of Celite, the Celite is washed with water and ethyl acetate successively, and the washings are combined with the initial filtrate. The organic phase is separated, and the aqueous phase is extracted with ethyl acetate. The organic phases are combined, washed twice with saturated sodium chloride solution, dried over anhydrous magnesium sulfate, filtered and evaporated at reduced pressure to obtain the crude product as a dark brown foam (22.94 g.).

Step 6

(Reaction CF)

1-(4'-Fluorophenyl)-4-(1'-methylethyl)-2-phenyl-1H-imidazole-5-methanol (Compound CVII)

100 ml. of 10% sodium hydroxide solution is added to a solution of 22.94 g. (≦65.1 mmoles) of crude Compound CVI from Step 5 in absolute ethanol, and the resulting reaction mixture is stirred at 20°–25° C. under nitrogen for 4 hours. The ethanol is evaporated at reduced pressure, and the resulting yellow paste is partitioned between ethyl acetate and water. The ethyl acetate phase is separated, and the aqueous phase is extracted twice with ethyl acetate. The three ethyl acetate phases are combined, washed twice with saturated sodium chloride solution, dried over anhydrous magnesium sulfate, filtered and concetrated at reduced pressure to a volume of about 200 ml. Petroleum ether is added to precipitate the product as a tan powder (11.54 g.). An analytical sample is recrystallized from ethyl acetate. M.p. 183°–186° C.

Step 7

(Reaction CG)

1-(4'-Fluorophenyl)-4-(1'-methylethyl)-2-phenyl-1H-imidazole-5-carboxaldehyde (Compound CVIII)

13.45 g. (43.3 mmoles) of Compound CVII is dissolved in 650 ml. of toluene with heating, 53.8 g. (619 mmoles) of activated manganese dioxide is added, and the reaction mixture is refluxed under nitrogen for 16 hours with stirring, cooled to 20°–25° C. and filtered through a pad of Celite. The Celite is washed with ethyl acetate, and the filtrate and ethyl acetate washings are combined and evaporated at reduced pressure to a tan solid. The tan solid is recrystallized from diethyl ether to obtain the product (5.12 g.). A second crop is obtained from the mother liquor by adding hexane. M.p. 159°–161° C.

Step 5A (Reaction CN)

1-(4'-F-uorophenyl)-4-(1'-methylethyl)-2-phenyl-1H-imidazole-5-carboxaldehyde (Compound CVIII)

A mixture of 5 l. of acetonitrile, 3 l. of water, 736 g. (2.72 moles) of potassium persulfate and 170 g. (0.68 mole) of copper (II) sulfate pentahydrate is heated at 65° C., 200 g. (0.68 mole) of Compound CV is added over a period of 8 minutes (the addition being slightly exothermic), and the reaction mixture is slowly heated to 75°–77° C., maintained at 75°–77° C. for 38 minutes and immediately cooled to 23° C., the reaction mixture being stirred under nitrogen throughout. The reaction solution is decanted, the solids in the reaction vessel are washed four times with 1 l. portions of methylene chloride, and the methylene chloride washings are combined with the decanted reaction solution. The aqueous layer is separated, and the organic layer is washed with 2 l. of water. The organic (bottom) layer is separated, and the solvent is distilled at a maximum external temperature of 55°–60° C. and 20-30 mm. Hg until a thick stirrable mixture results. 500 ml. of methylene chloride is added, and the mixture is heated at ~35° C. for 5 minutes, cooled to 25° C. and filtered. The filter cake is washed twice with 50 ml. portions of methylene chloride. The methylene chloride washings are combined with the filtrate, and as much of the methylene chloride as possible is distilled at 30°–45° C. and 20-30 mm. Hg until a thick stirrable slurry results. 1.5 l. of hexane is added, and the mixture is distilled at atmospheric pressure, the vapor temperature rising from 56° C. to 67° C. as the acetonitrile is azeotroped. The atmospheric distillation is continued for ~5 minutes after the vapor temperature rises to 67° C. to ensure complete removal of the acetonitrile, and as much of the remaining solvent as possible is distilled at ~50° C. and 20-30 mm. Hg. The resulting thick stirrable mixture is cooled to 30° C., 1 l. of dry tetrahydrofuran and 100 g. of aluminum oxide (90 activity) are added, and the mixture is stirred for 15 minutes and filtered. The filter cake is washed three times with 200 ml. portions of dry tetrahydrofuran, and the washing are combined with the initial filtrate to obtain a solution of about 192 g. of crude Compound CVIII in 1.6 l. of tetrahydrofuran which solution may be utilized in Part (b) of either the initial procedure or the revised procedure of Step 8.

Revised procedure:

200 g. (0.68 mole) of Compound CV is added over a period of 8 minutes to a mixture of 736 g. (2.72 moles) of potassium persulfate, 170 g. (0.68 mole) of copper (II) sulfate pentahydrate, 5 l. of acetonitrile and 3 l. of water stirred at an internal temperature of 65° C., the internal temperature rising to 68° C. during the exothermic addition, the reaction mixture is slowly heated to an internal temperature of 75° C., it exotherms to 77° C., and it is maintained at ~77° C. for 38 minutes and immediately cooled to 0° C., the reaction mixture being stirred under nitrogen throughout. 900 ml. of 20% sodium hydroxide solution is added over a period of 25 minutes to adjust the pH to 5-6 while maintaining a maximum internal temperature of 10° C., the addition being very exothermic. 2 l. of methylene chloride is added, the mixture is filtered, the blue filtercake is washed with 2 l. of methylene chloride, the filtrate and washing are combined, and the organic layer (usually the top layer) is separated and washed with 2 l. of water. The aqueous washing and the initial aqueous layer are combined and extracted with 500 ml. of methylene chloride. The methylene chloride washing is combined with the previous organic layer, and the solvent is distilled at 20-30 mm. Hg and an internal temperature of 30°-45° C. to obtain a thick stirrable slurry. 500 ml. of acetonitrile is added, the solvent is distilled at 20-30 mm. Hg. and a maximum internal temperature of 50° C., and this is repeated twice more. The obtained thick stirrable slurry is heated at 80° C. for 5-10 minutes and cooled to 0°-5° C., and the solid is collected by filtration, washed four times with 50 ml. portions of cold (5° C.) acetonitrile and vacuum dried at 50° C. for 15 hours to obtain the 93.4% pure product (130 g.), m.p. 157°–161° C. Recrystallization raised the m.p. to 161°–164° C.

Step 8

(Reaction CK)

Ethyl (E)-3-[1'-(4"-fluorophenyl)-4'-(1"-methylethyl)-2'-phenyl-1H-imidazol-5'-yl]propenoate (Compound CX)

(a) 1.8 g. of 60% sodium hydride/mineral oil (45.0 mmoles) is washed twice with hexane, the sodium hydride is suspended in 50 ml. of dry tetrahydrofuran (distilled from ketyl), the suspension is stirred at 20°–25° C., 1 ml. of triethyl phosphonoacetate (Compound CIX) is added, the reaction mixture is cooled to −20°–−15° C. with stirring, 7.6 ml. of Compound CIX is added dropwise with stirring at −20°–−15° C. (the total amount of Compound CIX being 8.6 ml. (9.6 g., 42.84 mmoles)), and the reaction mixture is stirred at −20°–−15° C. for 1 hour to obtain a solution of the ylide, the reaction mixture being stirred under nitrogen throughout.

(b) A solution of 11.0 g. (35.7 mmoles) of Compound CVIII in 100 ml. of dry tetrahydrofuran (distilled from ketyl) is added dropwise to the ylide solution of Part (a) of this step stirred at −20°–−15° C., the reaction mixture is allowed to warm to 20°–25° C. with stirring, an additional 150 ml. of dry tetrahydrofuran (distilled from ketyl) is added to dissolve the solids, and the reaction mixture is stirred at 20°–25° C. for 16 hours, the reaction mixture being maintained under nitrogen throughout. The reaction mixture is poured into water, diethyl ether, ethyl acetate and chloroform are successively added to dissolve all of the solids, the organic phase is separated, the aqueous phase is extracted with chloroform, and the organic phases are combined, washed twice with saturated sodium chloride solution, dried over anhydrous magnesium sulfate, filtered and evaporated at reduced pressure to obtain the product as a pale yellow powder (13.78 g.). An analytical sample is recrystallized from methylene chloride/n-hexane. M.p. 187°–189° C.

Revised procedure:

(a) A solution of 76.8 ml. (396.3 mmoles) of Compound CIX in 50 ml. of dry tetrahydrofuran is added over a period of 1 hour to a mixture of 16.7 g. of 60% sodium hydride/mineral oil (417.5 mmoles) and 500 ml. of dry tetrahydrofuran (dried over 4521 . ° molecular sieves) stirred at −5°–0° C., and the reaction mixture is stirred at −5°–0° C. for 1 hour, the reaction mixture being stirred under nitrogen throughout.

(b) The ylide solution from Part (a) is cooled to −5° C., a solution of 101.8 g. (330.0 mmoles) of Compound CVIII in 750 ml. of dry tetrahydrofuran is added rapidly over a 20 minute period with stirring at −5°–0° C., and the reaction mixture is allowed to warm to 20°–25° C. over a period of about 1 hour with stirring and stirred at 20°–25° C. for 2 hours, the reaction mixture being maintained under nitrogen throughout. The reaction mixture is poured into a mixture of 1.0 l. of saturated ammonium chloride solution and 1.0 l. of methylene chloride, the reaction flask is washed with 200 ml. of water and 500 ml. of methylene chloride successively, and the washings are combined with the quenched reaction mixture. The organic (lower) phase is separated, the aqueous phase is extracted with 500 ml. of methylene chloride, and the methylene chloride extract is combined with the aforementioned organic phase. The combined organic solution is washed with 500 ml. of saturated sodium chloride solution, dried over anhydrous sodium sulfate, filtered and evaporated to a thick white slurry at 50° C. and reduced pressure. 300 ml. of acetone is added, and the mixture is similarly evaporated to a thick white slurry. 250 ml. of acetone and 150 ml. of n-heptane are added, the mixture is cooled, and the product is collected by suction filtration and vacuum dried (98.1 g.), m.p. 189°–190° C. A less pure second crop is obtained by evaporating the mother liquor at reduced pressure to about 50% of its original volume, cooling, collecting the precipitate by suction filtration and vacuum drying the precipitate (23.4 g.), m.p. 185°–187° C.

Step 9

(Reaction CL)

3-[1'-(4''-Fluorophenyl)-4'-(1'''-methylethyl)-2'-phenyl-1H-imidazol-5'-yl]prop-2-en-1-ol (Compound CXI)

95.2 ml. of 1.5M. diisobutylaluminum hydride/toluene (142.8 mmoles) is added dropwise to a solution of 13.78 g. (36.4 mmoles) of Compound CX in 350 ml. of dry tetrahydrofuran (distilled from ketyl) stirred at 0° C. under nitrogen, and the reaction mixture is stirred at 0° C. under nitrogen for 45 minutes and quenched at 0° C. with saturated sodium sulfate solution. Sufficient 10% hydrochloric acid is added to dissolve the gel, and the resulting two phase mixture is extracted twice with diethyl ether. The organic phases are combined, washed twice with saturated sodium chloride solution, dried over anhydrous magnesium sulfate, filtered and evaporated to dryness at reduced pressure to obtain the crude product as a pale yellow solid (11.42 g.). A previous batch melted at 190°–193° C. (dec.)

Revised procedure:

1.268 l. of 1.0M. diisobutylaluminum hydride/hexane (1.268 moles) is added to a suspension of 120 g. (317.04 mmoles) of Compound CX in 1.0 l. of dry tetrahydrofuran (dried over 4Å. molecular sieves) stirred at −8° C. at a rate such that the temperature of the reaction mixture does not exceed 0° C., and the resulting nearly clear yellow solution is stirred for 2.5 hours while being allowed to gradually warm to 25° C., the reaction mixture being stirred under nitrogen throughout. The reaction mixture is carefully poured into a mixture of 2.0 l. of saturated ammonium chloride solution, 500 ml. of concentrated hydrochloric acid and 2.5 kg. of ice, 1.0 l. of methylene chloride is added, sufficient 10% hydrochloric acid is added to dissolve any aluminum salts (if necessary), the organic phase is separated, and the aqueous phase is extracted three times with 1 l. portions of methylene chloride. The methylene chloride extracts are combined with the aforementioned organic phase, and the combined organic solution is washed with 1 l. of saturated sodium chloride solution, dried over anhydrous sodium sulfate, filtered and concentrated at 50° C. and reduced pressure to a thick slurry. 500 ml. of n-heptane is added, the mixture is cooled to 0° C., and the resulting solids are collected by suction filtration, washed twice with 200 ml. portions of -n-heptane and vacum dried to constant weight (2 hours) at 40° C. to obtain the crude product as a very pale yellow powder (85.4 g.), m.p. 153°–160° C. (dec.) A second crop is obtained by concentrating the mother liquor at reduced pressure to about 50% of its original volume, cooling and collecting and air drying the resulting solid (1.4 g.).

Step 10

(Reaction CM)

(E)-3-[1-(4''-Fluorophenyl)-4'-(1'''-methylethyl)-2'-phenyl-1H-imidazol-5'-yl]prop-2-enal (Compound CXII)

11.4 g. (33.9 mmoles) of Compound CXI is dissolved in 250 ml. of dry tetrahydrofuran (distilled from ketyl), 29.5 g. (339 mmoles) of activated manganese dioxide is added, the reaction mixture is strirred at 20°–25° C. for about 3 hours, an additional 29.5 g. (339 mmoles) of activated manganese dioxide is added, and the reaction mixture is stirred at 20°–25° C. for 16 hours and filtered through a pad of Celite. The Celite is washed with ethyl acetate, the washing is combined with the filtrate, and the combined solution is evaporated to dryness at reduced pressure to obtain a yellow solid (10.03 g.). The yellow solid is crystallized from ethyl acetate/hexane to obtain an orange solid (6.74 g.) which is recrystallized from ethyl acetate to obtain the product as a yellow powder (4.29 g.). The mother liquors from the two crystallizations are combined, evaporated to dryness at reduced pressure and flash chromatographed on 300 g. of 230–400 mesh A.S.T.M. silica gel utilizing 30% diethyl ether/hexane as the eluant. The fractions containing the product are combined and evaporated to dryness at reduced pressure, and the residue is recrystallized from ethyl acetate/hexane to obtain additional product (3.72 g.). A previous batch melted at 163°–166° C.

Revised procedure:

400 g. (4.6 moles) of activated manganese dioxide is added in one portion to a suspension of 85 g. (252.7 mmoles) of Compound CXI in 1.0 l. of dry tetrahydrofuran (dried over 4Å. molecular sieves) stirred at 20°–25° C., the addition being slightly exothermic, and the reaction mixture is stirred at 20° C. under nitrogen for 17 hours and suction filtered through a 2.54 cm. pad of 70–230 mesh A.S.T.M. silica gel topped with a 7.62 cm. pad of Celite filter aid. The pads are washed with three 500 ml. portions of tetrahydrofuran, and the combined filtrate and washings are concentrated at 50° C. and reduced pressure to a volume of 150–200 ml. 500 ml. of n-heptane is added, the mixture is cooled to 0° C., and the resulting solids are collected by suction filtration, washed twice with n-heptane and vacuum dried at 45° C. to obtain the crude product as a pale yellow solid (54.0 g.).

Step 11

(Reaction I)

Ethyl (±)-(E)-7-[1'-(4''-fluorophenyl)-4'-(1''-methylethyl)-2'-phenyl-1H-imidazol-5'-yl]-5-hydroxy-3-oxohept-6-enoate (Compound CXIII)

1.54 g. of 60% sodium hydride/mineral oil (38.5 mmoles) is washed twice with hexane, the remaining powdered sodium hydride is suspended in 100 ml. of dry tetrahydrofuran, the suspension is cooled to −20°–−15° C., 4.55 g. (35.0 mmoles) of ethyl acetoacetate is added dropwise with stirring at −20°–−15° C., the reaction mixture is stirred at −20–−15° C. for 30 minutes, 23.0 ml. of 1.6M. n-butyllithium/hexane (36.75 mmoles) is added dropwise with stirring at −20°–−15° C., the reaction mixture is stirred at −20°–−15° C. for 10 minutes, a solution of 5.857 g. (17.5 mmoles) of Compound CXII in 100 ml. of dry tetrahydrofuran is added dropwise with stirring at −20°–−15° C., and the reaction mixture is stirred at −20°–−15° C. for 30 minutes, the reaction mixture being maintained under dry argon throughout. The reaction mixture is quenched at −20°–−15° C. with saturated ammonium chloride solution and warmed to 20°–25° C., the tetrahydrofuran is evaporated at reduced pressure, and the residue is partitioned between water and diethyl ether. The aqueous phase is reextracted with diethyl ether, and the diethyl ether phases are combined, washed twice with saturated sodium chloride solution, dried over anhydrous magnesium sulfate, filtered and evaporated at reduced pressure to a yellow foam. The foam is flash chromatographed on 350 g. of 230–400 mesh A.S.T.M. silica gel utilizing 70% diethyl ether/hexane as the eluant to obtain the product as a yellow solid (7.91 g.).

The product is a racemate that may be resolved by conventional means to obtain the 5R and 5S enantiomers.

Step 12

(Reaction J)

Ethyl (±)-erythro-(E)-3,5-dihydroxy-7-[1'-(4''-fluorophenyl)-4'-(1''-methylethyl)-2'-phenyl-1H-imidazol-5'-yl]hept-6-enoate (Compound CXIV)

(a) 34 ml. of 1.0M. tri-n-butylborane/tetrahydrofuran (34.0 mmoles) is added rapidly dropwise to a solution of 7.91 g. (17.0 mmoles) of Compound CXIII in 100 ml. of dry tetrahydrofuran (distilled from ketyl) stirred at 20°–25° C. under nitrogen, air is bubbled in for 1 minute, the reaction mixture is stirred at 20°–25° C. under nitrogen for 1 hour and cooled to −78° C., 3.22 g. (85.0 mmoles) of sodium borohydride is added in one portion, the reaction mixture is stirred at −78° C. under nitrogen for 16 hours, an additional 3.22 g. (85.0 mmoles) of sodium borohydride is added in one portion, and the reaction mixture is stirred at −78° C. under nitrogen for 64 hours, warmed to −25° C., stirred at −25° C. under nitrogen for 16 hours, quenched with 10% hydrochloric acid and partitioned between diethyl ether and water. The aqueous phase is neutralized with saturated sodium bicarbonate solution and extracted with diethyl ether. The two diethyl ether phases are combined, washed twice with saturated sodium chloride solution, dried over anhydrous magnesium sulfate, filtered and evaporated at reduced pressure to a yellow wax (11.79 g.). The yellow wax is recrystallized from isopropanol to obtain a white powder (2.61 g.) which is recrystallized from isopropanol to obtain the cyclic boron ester as a white powder (1.83 g.).

(b) 4.0 g. of the cyclic boron ester of Part (a) of this step is dissolved in methanol with warming (35°–40° C.) and the methanol is evaporated at reduced pressure and 35°–40° C., this procedure is repeated two more times, the residue is dissolved in warm methylene chloride, and hexane is added to obtain the product as a white solid (2.93 g.). A second crop may be obtained from the mother liquor. M.p. 149°–151° C. N.M.R. (CDCl$_3$): 1.26 (t, 3H), 1.36 (d, 6H), 1.61 (m, 2H), 2.45 (d, 2H), 3.13 (m, 1H), 3.23 (d, 1H), 3.30 (d, 1H), 4.16 (q, 2H), 4.19 (bm, 1H), 4.36 (bm, 1H,), 5.50 (dd, 1H), 6.19 (dd, 1H), 7.0–7.37 (m, 9H).

The product, the erythro racemate, may be resolved to obtain the 3R,5S and 3S,5R enantiomers, of which the former is preferred. The use of a non-stereoselective reduction would afford a mixture of all four stereoisomers wherein the ratio of the erythro stereoisomers to the threo stereoisomers ranges from 3:2 to 2:3. A mixture of the erythro and threo racemates wherein the ratio of the former to the latter is about 7:3 may be obtained by omitting the isopropanol recrystallizations from Part (a) of this step.

EXAMPLE A 1,1-Dimethylethyl (3R,5S)-3,5-di-(1',1'-dimethylethyl)-diphenylsilyloxy)-6-oxohexanoate

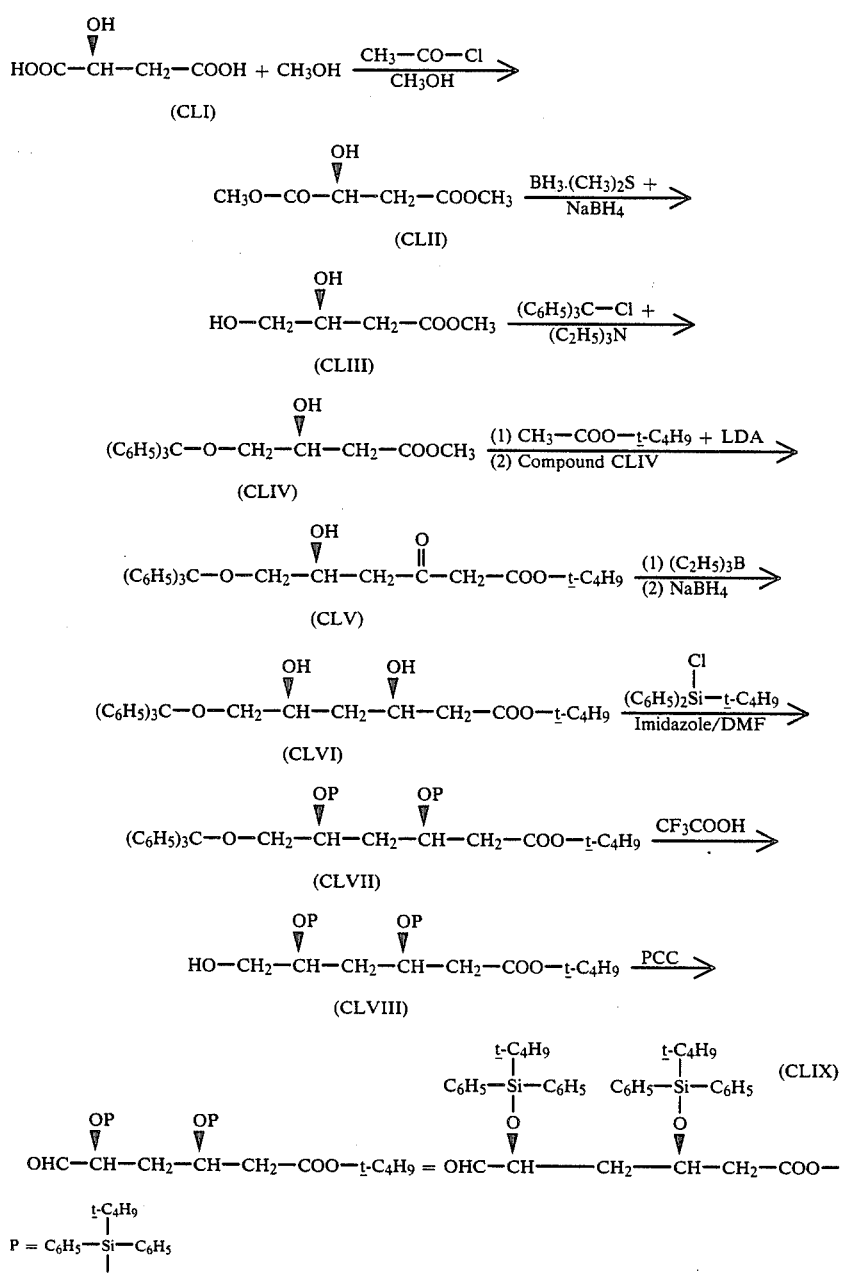

Step 1

Dimethyl (S)-2-hydroxybutanedioate (Compound CLII)

(a) 750 g. (9.6 moles) of acetyl chloride is added over a period of 30 minutes to 13.5 l. of methanol sitrred at −5°° C. while maintaining an internal temperature of 0°-2° C. (the addition being very exothermic), the reaction mixture is stirred at 0° C. for 1 hour, 1.76 kg. (13.1 moles) of (S)-2-hydroxybutanedioic acid is added over a period of 30 minutes while maintaining an internal temperature of 0°-2° C. (the addition being slightly exothermic), and the reaction mixture is stirred at 0°-2° C. for 2 hours and at 20°-25° C. for 16 hours, the reaction mixture being stirred under nitrogen throughout. 898 g. (8.47 moles) of anhydrous sodium carbonate is added over a period of 15 minutes while maintaining an internal temperature of 20°-25° C. to adjust the pH to 7-8 (the addition being slightly exothermic), and the reaction mixture is stirred at 20°-25° C. for 30 minutes and filtered. The filter cake is washed twice with 500 ml. portions of methanol, the filtrate and washings are combined, and the solution is evaporated at 25-30 mm. Hg while maintaining an internal temperature of 35°-40° C. to a volume of about 2.5 l. and filtered. The filter cake is washed with 500 ml. of methanol, the filtrate and washing are combined, and the solvent is distilled at 25-35 mm. Hg and an internal temperature of 40° C. to obtain the crude product (2.22 kg.).

(b) A solution of 300 g. of crude product from Part (a) of this step in 300 ml. of methylene chloride is added to a slurry of 300 g. of 70–230 mesh A.S.T.M. silica gel in 1.4 l. of methylene chloride, and the product is eluted with 7–8 l. of methylene chloride. The methylene chloride is distilled at 30–40 mm. Hg and an external temperature of 50° C. to obtain the partially purified product which is vacuum distilled at 0.6 mm. Hg and an internal temperature of 96°–98° C. to obtain the 96.7% pure product (239 g.). B.p. 90°–92° C./1.5–2 mm. Hg, 78°–80° C./0.6 mm. Hg.

(c) The remainder of the crude product is similarly purified.

Step 2 Methyl (S)-3,4-dihydroxybutanoate (Compound CLIII)

7.5 g. (0.2 mole) of sodium borohydride is added in one portion to a mixture of 523 ml. of 10M. borane-dimethylsulfide complex (5.23 moles borane) and 1.8 l. of dry tetrahydrofuran stirred at 20°–25° C., the reaction mixture is stirred at 20°–25° C. for 30 minutes, a solution of 744 g. of 94% pure Compound CLII (4.31 moles) in 1.2 l. of dry tetrahydrofuran is added over a period of 1 hour while maintaining with external cooling at 3°–5° C. an internal temperature of 20°–25° C. (the reaction is very exothermic, and hydrogen is evolved), and, after the exotherm stops, the reaction mixture is stirred at 20°–25° C. for 1 hour and cooled to 20° C., the reaction mixture being stirred under nitrogen throughout. 1.8 l. of methanol is slowly added while maintaining an internal temperature of 20°–25° C. (The first third of the addition is very exothermic and foaming occurs.) The reaction mixture is stirred for 30 minutes while maintaining an internal temperature of 20°–25° C., the solvent is distilled at 20–30 mm. Hg and an external temperature of 40°–45° C., 500 ml. of toluene is added, the solvent is distilled at 20–30 mm. Hg and an external temperature of 40°–45° C., an additional 500 ml. of toluene is added, and the solvent is distilled at 20–30 mm. Hg and an external temperature of 40°–45° C. to obtain the crude (89.7% pure) product as a very thick stirrable oil (633 g.). The entire reaction and the solvent distillations must be vented through bleach to trap any escaping dimethylsulfide.

Step 3

Methyl (S)-3-hydroxy-4-(triphenylmethoxy)butanoate (Compound CLIV)

(a) A solution of 1.82 kg. (6.53 moles) of triphenylmethyl chloride in 2.5 l. of methylene chloride is added over a period of 12 minutes to a mixture of 716 g. of 81.7% pure Compound CLIII (4.40 moles), 880 g. (8.7 moles) of triethylamine and 4.9 l. of methylene chloride stirred at 15° C. while maintaining an internal temperature of 15°–20° C. (the addition being exothermic), and the reaction mixture is stirred at 23° C. for 16 hours, stirred at an internal temperature of 38°–40° C. for 15 minutes (during which gas evolves) and cooled to 25° C., the reaction mixture being maintained under nitrogen throughout. 7.4 l. of water is added, the bottom organic layer is separated, the aqueous layer is extracted with 500 ml. of methylene chloride, the methylene chloride extract is combined with the bottom organic layer, and the combined organic layers are washed successively with 7.4 l. of water, 7.4 l. of saturated sodium bicarbonate solution and 3.7 l. of water and filtered to remove any insolubles. The solvent is distilled at 20–30 mm. Hg and a maximum external temperature of 50°–60° C. to obtain a thick dark stirrable oil. 2.5 l. of methanol is added with stirring at 50° C., and the mixture is stirred at 50° C. for 5 minutes, cooled to 20° C. and filtered. The filter cake is washed with 1 l. of methanol, the filtrate and washing are combined, and the solvent is distilled at 20–30 mm. Hg and an external temperature of about 50° C. to obtain the crude product as a thick stirrable brown oil (1.75 kg.).

(b) A 90 cm.×13 cm. chromatographic column is charged with 7.2 l. of 1:2 ethyl acetate/mixed hexanes, 450 g. of sea sand is added, a slurry of 4 kg. of 70–230 mesh A.S.T.M. silica gel in 12 l. of 1:2 ethyl acetate/mixed hexanes is added while draining some of the solvent from the bottom of the column, sufficient solvent to lower the liquid level to the top of the silica gel is drained from the column, a solution of 1.0 kg. of the crude product of Part (a) of this step in 1.0 l. of methylene chloride is added, sufficient solvent to lower the liquid level to the top of the silica gel is drained from the column, the column is eluted with 18 l. of 1:2 ethyl acetate/mixed hexanes to obtain six fractions, and the column is eluted with 12 l. of 1:1 ethyl acetate/mixed hexanes to obtain eight fractions containing relatively pure product. These eight fractions are combined, the solvent is distilled at 20–30 mm. Hg and 60° C. to obtain a thick stirrable oil, 1 l. of isopropanol is added, the solvent is distilled at 20–30 mm. Hg and a maximum internal temperature of 60° C., an additional 1 l. of isopropanol is added, the solvent is distilled at 20–30 mm. Hg and a maximum internal temperature of 60° C., and the residue is added to 2 l. of isopropanol. The resulting solution is cooled to 0°–5° C. and maintained at this temperature for 3–4 hours. The solid is collected by filtration, washed twice with 250 ml. portions of cold (0°–5° C.) isopropanol and vacuum dried at 50°–60° C. to constant weight to obtain the 94.9% pure product (473 g.), m.p. 80°–82° C., $[\alpha]_{589}^{25} = -5.52°$ (c = 1.5580, $CH_2Cl_2$). All chromatography fractions and mother liquors containing impure product may be combined and rechromatographed, etc. to obtain additional product.

(c) The balance of the crude product is similarly purified.

Step 4

1,1-Dimethylethyl (S)-5-hydroxy-3-oxo-6-(triphenylmethoxy)hexanoate (Compound CLV)

1.98 l. of 1.6M. n-butyllithium/hexane (3.17 moles) is added over a 30 minute period to a mixture of 321 g. (3.17 moles) of diisopropylamine and 1.5 l. of dry tetrahydrofuran stirred at −50°−−40° C. during which the internal temperature rises to −5°-0° C., the pale yellow solution is stirred at −5°-0° C. for 30 minutes and cooled to −65° C., 367 g. (3.16 moles) of t-butyl acetate is added over a period of 40 minutes while maintaining an internal temperature of −63°-60° C. (the addition being exothermic), the reaction mixture is stirred at −62°−−60° C. for 40 minutes, a solution of 300 g. (0.80 mole) of 95+% pure Compound CLIV in 1.35 l. of dry tetrahydrofuran is added over a period of 25 minutes while maintaining an internal temperature of −62°−−58° C. (the addition being exothermic), and the reaction mixture is stirred at −62°−−58° C. for 1 hour, warmed to −5°-0° C. over a period of 45 minutes and stirred at −5°-0° C. for 30 minutes, the reaction mixture being stirred under nitrogen throughout. 1.8 l. of saturated ammonium chloride solution is added over a period of 3 minutes while maintaining an internal temperature of below 15° C. (the addition being exothermic), the mixture is stirred at 10°-15° C. for 10 minutes, 2.1 l. of toluene is added, and the top organic layer is separated, washed three times with 1.5 l. portions of water and, if any insolubles are present, filtered. The solvent is distilled at 20-30 mm. Hg and an internal temperature of 50°-60° C. to obtain the crude (87.1% pure) product as a very thick yellow oil that is stirrable at 50° C. (415 g.)

Step 5

1,1-Dimethylethyl (3R,5S)-3,5-dihydroxy-6-(triphenylmethoxy)hexanoate (Compound CLVI)

A mixture of 715 ml. of 1M. triethylborane/tetrahydrofuran (715 mmoles), 4.76 l. of dry tetrahydrofuran and 1.44 l. of methanol is stirred at 18°-22° C. for 45 minutes and cooled to −75° C., a solution of 254.4 g. of crude (90% pure) Compound CLV (0.497 mole) in 960 ml. of dry tetrahydrofuran is added over a period of 15 minutes while maintaining an internal temperature of −75°−−72° C., the reaction mixture is stirred at −76°−−75° C. for 1 hour, 24.9 g. (0.66 mole) of sodium borohydride is added in portions over a period of 15 minutes while maintaining an internal temperature of −76°−−72° C., and the reaction mixture is stirred at −77°−−76° C. for 4.5 hours, the reaction mixture being stirred under nitrogen throughout. 756 ml. of saturated ammonium chloride solution is slowly added over a period of 25 minutes while maintaining an internal temperature of −76°−−67° C. (the addition is exothermic, and some foaming occurs), the mixture is stirred at −68°−−67° C. for 30 minutes and warmed to 10°-15° C. over a period of 30 minutes, 360 ml. of water is added, the mixture is extracted with 3.6 l. of ethyl acetate, the top organic layer is separated and washed successively with 750 ml. of a 1:1 mixture of water and saturated sodium chloride solution and 750 ml. of saturated sodium chloride solution, and the solvent is distilled at 20-30 mm. Hg and a maximum external temperature of 50° C. 180 ml. of ethyl acetate is added, the solvent is distilled at 20-30 mm. Hg and a maximum external temperature of 50° C., and these two steps are repeated once. 2.91 l. of ethyl acetate is added to the obtained thick oil (the cyclic boronate), 290 ml. of 30% hydrogen peroxide solution (2.84 moles) is slowly added over a period of 20-30 minutes while maintaining an internal temperature of 20°-25° C. (the addition initially being exothermic), and the reaction mixture is stirred at 20°-25° C. for 2.5 hours and added to 360 ml. of water. The top organic layer is separated, washed three times (for 10-15 minutes each time) with 480 ml. portions of cold (0°-5° C.) 10% sodium sulfite solution (until the organic layer is free of peroxide) while maintaining an internal temperature of 25° C. and washed successively with 480 ml. of saturated sodium bicarbonate solution, 480 ml. of water (any emulsion that forms will separate within about an hour) and 480 ml. of saturated sodium chloride solution. The top organic layer is separated, and the solvent is distilled at 20-30 mm. Hg and a maximum external temperature of 50°-60° C. 326 ml. of methanol is added, the solvent is distilled at 20-25 mm. Hg and an internal temperature of 50°-60° C., and these two steps are repeated four more times. 100 ml. of toluene is added, the solvent is distilled at 20-30 mm. Hg and an internal temperature of 60° C., and these two steps are repeated three more times. The obtained oil is heated for an additional 3-4 hours at 20-30 mm. Hg and 50°-60° C. to obtain the crude (66.8% pure) product (255 g.). (The ratio of the 3R,5S isomer to the 3S,5S isomer is about 69:1 although in other batches it was as low as about 23:1.)

Step 6 1,1-Dimethylethyl (3R,5S)-3,5-di-[(1',1'-dimethylethyl)diphenylsilyloxy]-6-(triphenylmethoxy)hexanoate (Compound CLVII)

132.5 g. (1.95 moles) of imidazole is added to a mixture of 267 g. of crude (55.8% pure) Compound CLVI (0.322 mole) and 900 ml. of N,N-dimethylformamide while maintaining an internal temperature of 23°-25° C., the mixture is heated to 70°-72° C., 235.8 g. (0.86 mole) of t-butyldiphenylchlorosilane is added over a period of 2 minutes, and the reaction mixture is stirred at 70°-72° C. for 18 hours and cooled to 10° C., the reaction mixture being stirred under nitrogen throughout. The reaction mixture is added to a mixture of 2.5 l. of hexane and 1.1 l. of water, the mixture is stirred for 5 minutes, the organic top layer is separated and washed twice with 1.1 l. portions of water, and the solvent is distilled at 20-30 mm. Hg and an external temperature of 40°-60° C. to obtain the crude (62.8% pure) product (437.7 g.).

Step 7

1,1-Dimethylethyl (3R,5S)-3,5-di-[(1',1'-dimethylethyl)diphenylsilyloxy]-6-hydroxyhexanoate (Compound CLVIII)

(a) A cold solution prepared from 960 g. of water, 600 g. of ice and 740 g. (6.49 moles) of trifluoroacetic acid is added over a period of 2 minutes to a solution of 432 g. of crude (62.8% pure) Compound CLVII (0.29 mole) in 3.4 l. of methylene chloride while maintaining a maximum internal temperature of 25° C., and the reaction mixture is stirred at 22°-26° C. for 2.5 hours, the reaction mixture being stirred under nitrogen throughout. The organic bottom layer is separated and washed successively with 1.1 l. of saturated sodium bicarbonate solution and 1.0 l. of water, and the solvent is distilled at 20-30 mm. Hg and a maximum external temperature of 60° C. 100 ml. of mixed hexanes is added to the residue, the solvent is distilled at 20-30 mm. Hg and a maximum internal temperature of 60° C., and these two steps are repeated once, the distillation being continued until no more solvent distills off. 1.1 l. of mixed hexanes is added to the obtained thick semi-solid, the mixture is heated at 40°-45° C. for 10-15 minutes, cooled to 0°-5° C. and maintained at 0°-5° C. for 10 minutes, and the solid is collected by filtration and washed twice with 100 ml. portions of cold (10° C.) mixed hexanes. The filtrate and hexane washings are combined, and the solvent is distilled at 20-30 mm. Hg and an external temperature of 40°-60° C. to obtain the crude product as an oil (330 g.).

(b) The crude product of Part (a) is purified by HPLC using a Kiloprep 250 Millipore Process HPLC system with a reverse phase Kiloprep 250 $C_{18}$ cartridge (80 microns) and a 200 nm. detector. The column is flashed with methylene chloride until it is decontaminated (as indicated by the UV detector) and flushed with methanol for about 10 minutes and then with 9:1 methanol/water for about 6 minutes at a flow rate of 0.5 l./min. A solution of the crude product of Part (a) of this step in a mixture of 393 ml. of methanol and 22 ml. of water is placed on the column, and the column is eluted with 9:1 methanol/water for about 22 minutes, 11 minutes and 3 minutes to obtain fractions 1-3 and with methanol for about 4 minutes and 7 minutes to obtain fractions 4 and 5, the flow rate being 0.5/min. Fractions 4 and 5 are combined, the solvent is distilled at 20-40 mm. Hg and a maximum internal temperature of 40° C., 250 ml. of methylene chloride is added to the residue, the mixture is stirred at 30° C. for 5 minutes, the organic bottom layer is separated, and the solvent is distilled at 20-30 mm. Hg and a maximum internal temperature of 40°-45° C. 100 ml. of n-heptane is added, the solvent is distilled at 20-30 mm. Hg and 40°-45° C., and these two steps are repeated once. 460 ml. of n-heptane is added to the residue, and the mixture is heated to 80°-90° C. to dissolve the oil, allowed to cool to 20°-25° C. with stirring until solid forms and maintained at 10° C. for 2-3 hours. The resulting white solid is collected by filtration, washed twice with 50 ml. portions of cold (10° C.) n-heptane and vacuum dried to constant weight at 50° C. for 15 hours to obtain the 95.5% pure product as a white solid (122 g.). m.p. 79°-80° C., $[\alpha]_{589}^{20} = +8.35°$ (c=5.0, $CH_2Cl_2$). (The ratio of the 3R,5S isomer to the 3S,5S isomer is about 76:1.)

Step 8

1,1-Dimethylethyl (3R,5S)-3,5-di-[(1',1'-dimethylethyl)diphenylsilyloxy]-6-oxohexanoate (Compound CLIX)

150 g. (0.70 mole) of pyridinium chlorochromate is added over a period of 3 minutes to a mixture of 200 g. (0.28 mole) of 96.6% pure Compound CLVIII, 2 l. of methylene chloride and 400 g. of 4Å. powdered molecular sieves stirred at 20° C. while maintaining an internal temperature of 20°-22° C. (the addition being slightly exothermic), and the reaction mixture is vigorously stirred for 1 hour at 22°-25° C., the reaction mixture being stirred under nitrogen throughout. 3.32 l. of n-heptane is added, and the mixture is stirred at 23° C. for 5 minutes and filtered through 250 g. of Celite® filter aid pre-wet with n-heptane. The filter cake is washed twice with 200 ml. portions of n-heptane, the filtrate and the n-heptane washings are combined, and the solvent is distilled at 20-30 mm. Hg and a maximum external temperature of 45°-50° C. 100 ml. of n-heptane is added, the solvent is distilled at 20-30 mm. Hg and a maximum external temperature of 45°-50° C., and this is repeated once. The resulting oil is dissolved in 400 ml. of 1:12 ethyl acetate/mixed hexanes and chromatographed on 420 g. of 70-230 mesh A.S.T.M. silica gel topped with about 2.5 cm. of sea sand utilizing a column having a 7 cm. inside diameter and 4 l. of 1:12 ethyl acetate/mixed hexanes as the eluant. The solvent is distilled at 20-30 mm. Hg and an external temperature of 50°-55° C. 100 ml. of n-heptane is added, the solvent is distilled at 20-30 mm. Hg and an external temperature of 50°-55° C., this is repeated once, and the residue is maintained at this pressure and temperature for 2 hours. 335 ml. of mixed hexanes is added at 40°-50° C. to the obtained thick oil, and the mixture is cooled to −35°−−30° C., seeded and maintained at −35°−−30° C. for 1 hour. The resulting white solid is collected by filtration, washed twice with 50 ml. portions of cold (−25°−−20° C.) mixed hexanes and dried to constant weight at 20-30 mm. Hg and 45°-50° C. for 24 hours to obtain the 99% pure product (175.2 g.), m.p. 81°-82° C., $[\alpha]_{589}^{25} = +5.21°$ (c=5.0, $CH_2Cl_2$). (The ratio of the 3R,5S isomer to the 3S,5S isomer is about 99:1.)

The stereochemistry of the compound may also be designated as R[R*,S*].

EXAMPLE 1A 1,1-Dimethylethyl (3R,5S)-(E)-3,5-dihydroxy-7-[1'-(4"-fluorophenyl)-4'-(1"-methylethyl)-2'-phenyl-1H-imidazol-5'-yl hept-6-enoate

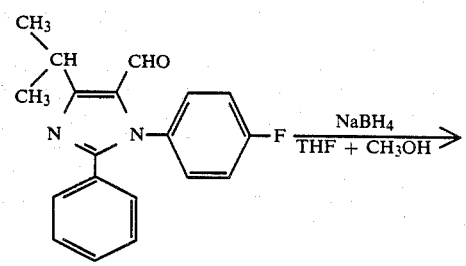

(CVIII)

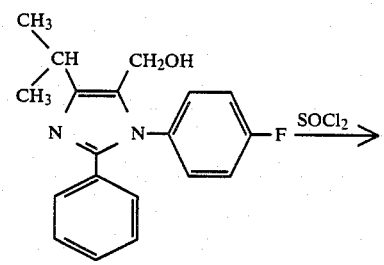

(CVII)

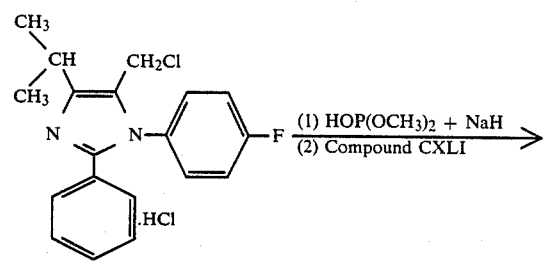

(CXLI)

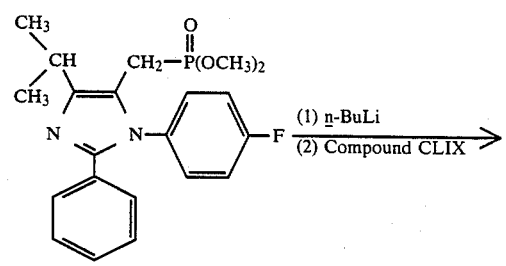

(CXLII)

-continued

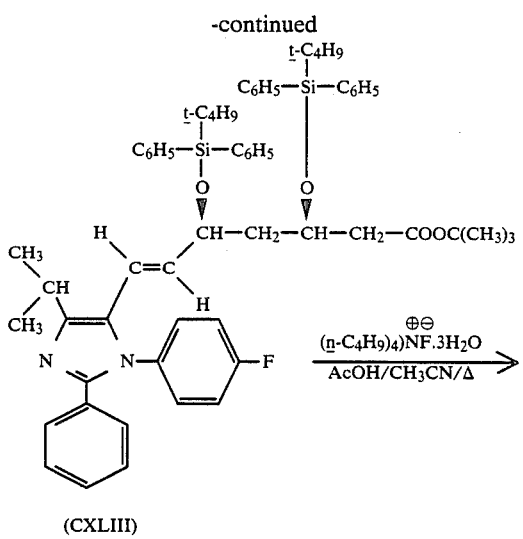

(CXLIII)

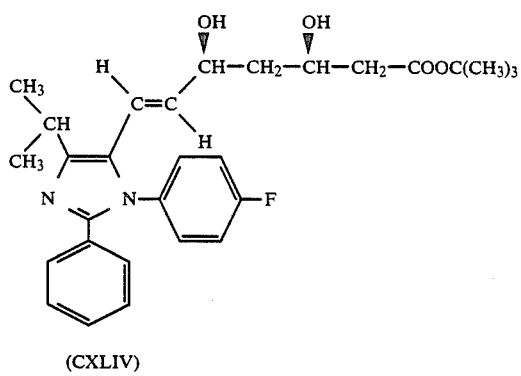

(CXLIV)

Step 1

(Reaction DI)

1-(4'-Fluorophenyl)-4-(1'-methylethyl)-2-phenyl-1H-imidazole5-methanol (Compound CVII)

8.73 g. (0.23 mole) of sodium borohydride is added over a period of 10-15 minutes to a mixture of 103.2 g. (0.335 mole) of Compound CVIII, 335 ml. of dry tetrahydrofuran and 335 ml. of methanol stirred at 5° C. while maintaining an internal temperature of 5°-25° C., the addition being exothermic, and the reaction mixture is stirred at 20°-25° C for 1.5 hours, the reaction mixture being stirred under nitrogen throughout. The reaction mixture is filtered, and the solvent is distilled at 20-30 mm. Hg and an external temperature of 50° C. to obtain a thick stirrable slurry. The slurry is cooled to 17° C., 350 ml. of water is added over a period of 10 minutes, and the mixture is stirred for 10-15 minutes and filtered. The resulting solid is collected by filtration, washed twice with 100 ml. portions of water and vacuum dried at 40° C. for 16 hours. The solid is added to 200 ml. of toluene, and the mixture is refluxed for 10-15 minutes, cooled 0° C. and stirred at 0° C. for 10-15 minutes The solid is collected by filtration, washed with 100 ml. of cold toluene, washed with 50 ml. of n-hexane and vacuum dried to constant weight at 50° C. for 16 hours to obtain the 98.5% pure off-white solid product (91 g. (87.6%)), m.p. 186°-188° C.

Step 2

(Reaction DA)

5-Chloromethyl-1-(4'-fluorophenyl)-4-(1'-methylethyl)-2-phenyl-1H-imidazole.hydrochloride (Compound CXLI)

127.1 g. (1.07 moles) of thionyl chloride is added over a period of 30 minutes to a mixture of 221 g. (0.712 mole) of Compound CVII and 890 ml. of methylene chloride stirred at 5° C. while maintaining a maximum internal temperature of 10° C., the addition being exothermic, and the reaction mixture is stirred at 20°-25° C. for 22 hours, the reaction mixture being stirred under nitrogen throughout. 300 ml. of toluene is added, the mixture is distilled at 160-216 mm. Hg, a maximum internal temperature of 40°-49° C. and a vapor temperature of 35°-41° C. to recover 480 ml. of distillate, an additional 300 ml. of toluene is added, the mixture distilled under the same conditions to recover 370 ml. of distillate, an additional 300 ml. of toluene is added, and the mixture is distilled under the same conditions to recover 330 ml. of distillate, the final pressure being 77 mm. Hg and the final pot and vapor temperatures being 45° C. The mixture is cooled to 0°-5° C. and maintained at this temperature for 1 hour, and the light beige solid is collected by filtration, washed with 250 ml. of cold (0° C.) toluene, washed with 300 ml. of n-heptane and vacuum dried under a nitrogen sweep at 40°-45° C. for 18 hours to obtain the product (260 g. (99.9%)), m.p. 169°-172° C.

Step 3

(Reaction DC)

Dimethyl [[1-(4'-fluorophenyl)-4-(1'-methylethyl)-2-phenyl-1H-imidazol-5-yl]methyl]phosphonate (Compound CXLII)

51.7 g. of 60% sodium hydride/mineral oil (1.293 moles) is added portionwise over a period of 10 minutes to 1.83 l. of dry tetrahydrofuran stirred at 20°-25° C., 156.4 g. (1.421 moles) of dimethyl phosphite is added dropwise over a 20 minute period with stirring while maintaining an internal temperature of 20°-25° C., the addition being slightly exothermic, the reaction mixture is stirred at 25° C. for 1.25 hours, 225 g. (0.616 mole) of Compound CXLI is added portionwise over a period of 20 minutes while maintaining an internal temperature of 20°-27° C., the addition being slightly exothermic, and the reaction mixture is stirred at 20°-25° C. for 19 hours, the reaction mixture being stirred under nitrogen throughout. 1.83 l. of methylene chloride is added over a period of 2 minutes while maintaining an internal temperature of 25°-30° C., the mixture is cooled to 20° C., and 430 ml. of water is added over a period of 2 minutes while maintaining an internal temperature of 20° C. The organic top layer is separated, washed with 300 ml. of water and distilled at 170-218 mm. Hg, a maximum internal temperature of 22° −27° C. and a vapor temperature of 20°-26° C. to recover 2.5 l. of distillate. The cloudy mixture is cooled to 5° C., stirred at this temperature for 30 minutes and filtered. The filtrate is distilled at 170-210 mm. Hg, a maximum internal temperature of 25°-26° C. and a vapor temperature of 24°-27° C. to recover 82 ml. of distillate. 400 ml. of toluene is added, and the mixture is distilled at 82-128 mm. Hg, a maximum internal temperature of 30°-48° C. and a vapor temperature of 25°-42° C. to recover 230 ml. of distillate, an additional 230 ml. of toluene is added, and the mixture is distilled under the same conditions to recover 190 ml. of distillate. The resulting light brown mixture is heated to 80° C., cooled to 0° (crystallization commences at ~40° C.) and stirred at 0° C. for 30 minutes. The resulting off-white solid is collected by filtration, washed with 100 ml. of toluene, washed with 100 ml. of n-heptane and vacuum dried under a nitrogen sweep at 45° C. for 19 hours to obtain the product (175 g. (70.8%)), m.p. 143°–145° C.

Step 4

(Reaction E) 1,1-Dimethylethyl (3R,5S)-(E)-3,5-di-[(1',1'-dimethylethyl)diphenyl-silyloxy]-7-[1'-(4"-fluorophenyl)-4'-(1"'-methylethyl)2'-phenyl-1H-imidazol-5'-yl]hept-6-enoate (Compound CXLIII)

104.5 ml. of 1.6M. n-butyllithium/hexane (0.1672 mole) is added dropwise over a period of 20–25 minutes to a suspension of 63.5 g. (0.158 mole) of Compound CXLII in 275 ml. of dry tetrahydrofuran stirred at −10° C. while maintaining an internal temperature of −10°-−3° C., the addition being exothermic, the reaction mixture is stirred at −10°-−3° C. for 30–40 minutes, a solution of 99.0 g. (0.1372 mole) of 96.3% pure Compound CLIX in 200 ml. of dry tetrahydrofuran is added dropwise over a period of 25–35 minutes while maintaining an internal temperature of −10°-−5° C., the addition being moderately exothermic, the reaction mixture is stirred for 1 hour while allowing the internal temperature to rise to 20°–25° C., and the reaction mixture is stirred at 20°–25° C. for 28–30 hours and cooled to 10° C., the reaction mixture being stirred under nitrogen throughout. 500 ml. of saturated ammonium chloride solution is added dropwise with stirring while maintaining an internal temperature of 10°–16° C., the reaction vessel is rinsed with 500 ml. of toluene, the toluene rinse is combined with the quenched two-phase reaction mixture, the mixture is thoroughly mixed, the organic top layer is separated, the aqueous lower layer is extracted with 200 ml. of toluene, and the toluene extract and the previous organic top layer are combined and evaporated at reduced pressure and 55°–60° C. to obtain a thick red-brown oil. The obtained oil is dissolved in 75 ml. of toluene, and the solution is applied to a bed of 1.0 kg. of 70–230 mesh A.S.T.M. silica gel slurry-packed in toluene in a 3 l. filtration funnel. The silica gel bed is eluted with ~3.15 l. of toluene until the product begins to be eluted (as determined by thin layer chromatography) and then with ~4.45 l. of 10% ethyl acetate/toluene. The fractions containing the product are combined and evaporated at reduced pressure and 55°–60° C. to obtain the crude product as a thick orange gum (83.1 g.).

Step 5

(Reaction F)

1,1-Dimethylethyl (3R,5S)-(E)-3,5-dihydroxy-7-[1'-(4"-fluorophenyl)-4'-(1"'-methylethyl)-2'-phenyl-1H-imidazol-5'-yl]hept-6-enoate (Compound CXLIV)

A solution of 166.2 g. (≦0.171 mole) of Compound CXLIII in 1.2 l. of acetonitrile is added rapidly to a mixture of 539.0 g. (1.708 moles) of tetra-n-butylammonium fluoride trihydrate, 97 ml. (1.694 moles) of glacial acetic acid and 1.0 l. of acetonitrile stirred at an internal temperature of 50° C., and the resulting solution is heated to 60° C., maintained at 60° C. for 48 hours and cooled to 25° C., the reaction mixture being stirred under nitrogen throughout. The reaction mixture is poured into 1.0 l. of saturated sodium bicarbonate solution, 2.0 l. of ethyl acetate is added, the two-phase mixture is mixed and allowed to separate, the organic upper layer is separated, the aqueous lower layer is extracted three times with 1.0 l. portions of ethyl acetate, and the three ethyl acetate extracts and the previous organic upper layer are combined, washed four times with 2.0 l. portions of water, washed once with 1.0 l. of saturated sodium chloride solution and evaporated at 50°–55° C. and reduced pressure to a dark red-brown oil. The obtained oil is applied to a bed of 800 g. of 70–230 mesh A.S.T.M. silica gel slurry packed in 1:1 ethyl acetate/n-hexane in a 2 l. filtration funnel, and the silica gel bed is eluted with ~7 l. of 1:1 ethyl acetate/n-hexane. The fractions containing more than a trace of the product (as determined by thin layer chromatography) are combined, evaporated at 50°–55° C. and reduced pressure to a volume of 75–100 ml., 350 ml. of n-hexane and a seed crystal (if available) are added, the mixture is stirred at 0° C. for 30 minutes, and the resulting solid is collected by filtration, washed twice with 50 ml. portions of n-hexane and vacuum dried at 45° C. for 18 hours to obtain the product as a very pale cream-colored solid (42.5 g. (56%)), m.p. 143°–144° C., $[\alpha]_D^{25} = +5.7°$ (c=3.2, $CH_2Cl_2$). Another batch, recrystallized from ethyl acetate/n-hexane, had an m.p. of 145°–146° C.

EXAMPLE 2

Sodium (±)-erythro-(E)-3,5-dihydroxy-7-[1'-(4"-fluorophenyl)-4'-(1"'-methylethyl)-2'-phenyl-1H-imidazol-5'-yl]hept-6-enoate (Reaction AA)

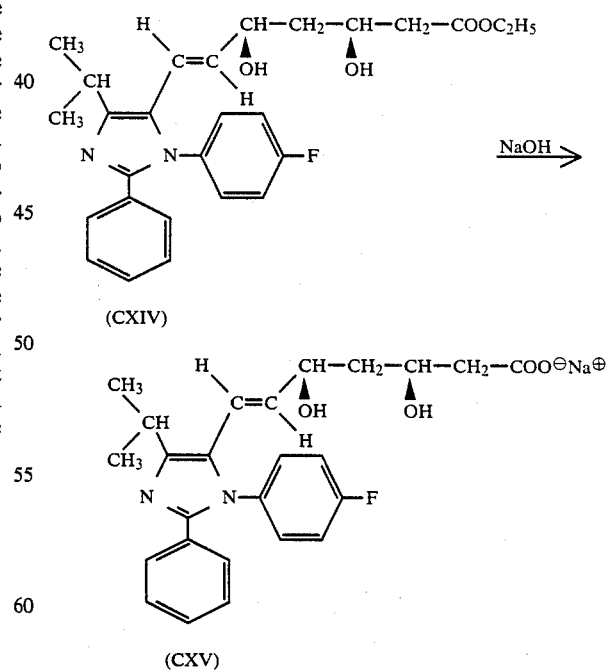

6.2 ml. of 1N. sodium hydroxide solution (6.2 mmoles) is added dropwise to a solution of 3.0 g. (6.52 mmoles) of Compound CXIV in 125 ml. of absolute ethanol stirred at 20°–25° C., the reaction mixture is stirred at 20°–25° C. for 2 hours and evaporated at reduced pressure to dryness, the residue is partitioned between water and methylene chloride, sufficient water is added to break the resulting emulsion, the aqueous layer is carefully separated, most of the water is evaporated at reduced pressure, and the resulting slurry is frozen at −78° C. and lyophilized to obtain the product as a pale yellow powder (3.02 g.), m.p. 217°–224° C. (dec.) (softens and loses water at 100°–116° C.) N.M.R. (CDC13 +CD3SOCD3): 1.32 (d, 6H), 1.53 (m, 2H), 2.30 (m, 2H), 3.13 (m, 1H), 4.08 (bm, 1H), 4.24 (bm, 1H), 5.50 (dd, 1H), 6.18 (dd, 1H), 7.0–7.3 (m, 9H).

The product, the erythro racemate, may be resolved to obtain the 3R,5S and 3S,5R enantiomers, of which the former is preferred. The use of a starting material synthesized by using a non-stereoselective reduction in Step 12 of Example 1 would afford a mixture of all four stereoisomers wherein the ratio of the erythro stereoisomers to the threo stereoisomers ranges from 3:2 to 2:3.

EXAMPLE 2A

Sodium (3R,5S)-(E)-3,5-dihydroxy-7-[1'-(4''-fluorophenyl)-4'-(1''-methylethyl)-2'-phenyl-1H-imidazol-5'-yl]hept-6-enoate (Reaction AA)

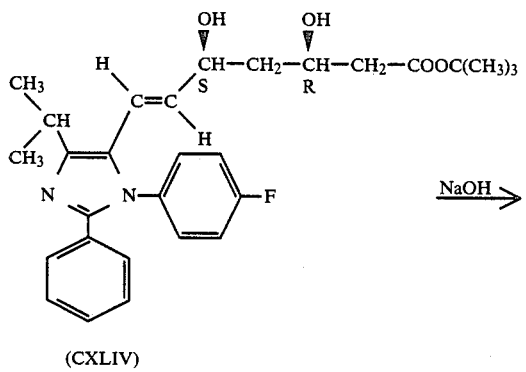

(CXLIV)

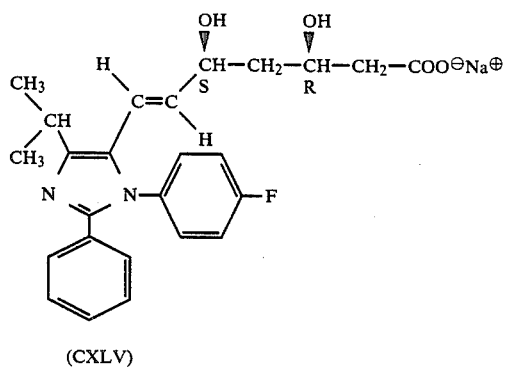

(CXLV)

182.6 ml. of freshly prepared 1.0N. sodium hydroxide solution (0.1826 mole) is added dropwise to a solution of 90.94 g. (0.184 mole) of Compound CXLIV in 750 ml. of ethanol stirred at 25° C., the internal temperature rising to 29° C. during the addition, and the reaction mixture is stirred for 1 hour while allowing the internal temperature to drop to 22° C., the pH of the reaction mixture being about 7.5–8 and the reaction mixture being stirred under nitrogen throughout. 850 ml. of methyl t-butyl ether is added, the mixture is mixed for ~5 minutes, and the solid is collected by suction filtration and washed once with 200 ml. of methyl t-butyl ether. The solid is suspended in 500 ml. of methyl t-butyl ether, the suspension is stirred at 20°–25° C. for ~15 minutes, the solid is collected by suction filtration, and this is repeated once. The solid is vacuum dried at 60° C. for 20–24 hours to obtain the product as a nearly colorless amorphous powder (74.38 g.). A second crop is obtained by combining and evaporating at reduced pressure the mother liquors from all of the filtrations, dissolving the residue in 70 ml. of ethanol and sufficient water at 60°–65° C. to form a clear light yellow solution, cooling the solution to 25° C., adding 200 ml. of methyl t-butyl ether, collecting the solid by suction filtration, washing the solid with 100 ml. of methyl t-butyl ether, repeating the entire procedure (commencing with dissolution in a mixture of 70 ml. of ethanol and water) as many times as necessary to remove any deeply yellow colored material or other extraneous material as indicated by thin layer chromatography, slurrying the resulting solid in 200 ml. of methyl t-butyl ether for 10–15 minutes at 20°–25° C., collecting the solid by suction filtration and vacuum drying the solid at 60° C. for 24 hours (5.03 g.). Total yield: 79.41 g. 94.4%), m.p. 218°–220° C. (dec.) (yellow at 190°–205° C.), $[\alpha]_D^{20} = +18.98°$ (c=3.16, CH3OH).

The product contains ~0.5% of threo compound.

EXAMPLE 3

Ethyl (±)-erythro-(E)-3,5-dihydroxy-7-[4'-(4''-fluorophenyl)-1'-(1''-methylethyl)-2'-phenyl-1H-imidazol-5'-yl]hept-6-enoate

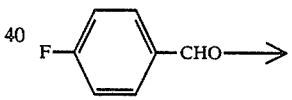

(CXVIII)

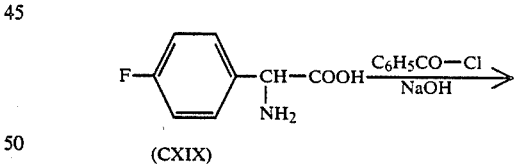

(CXIX)

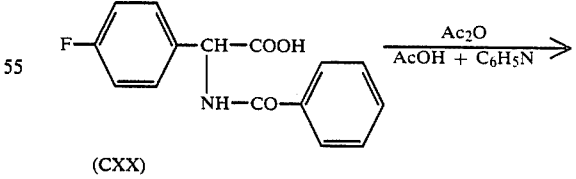

(CXX)

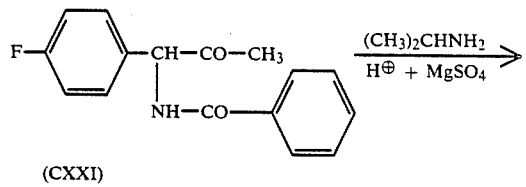

(CXXI)

-continued
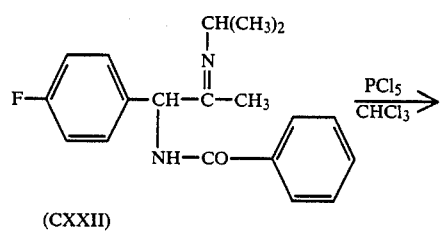
(CXXII)
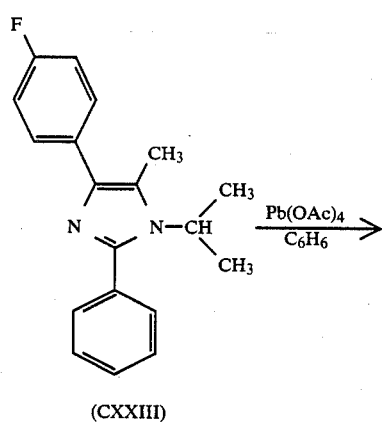
(CXXIII)
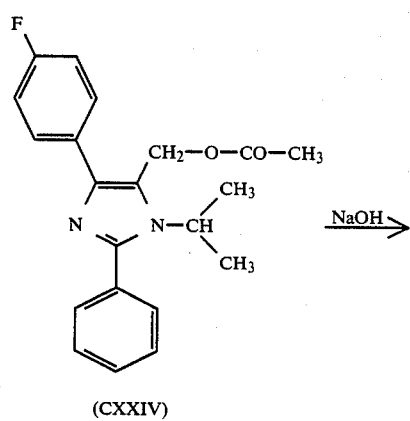
(CXXIV)
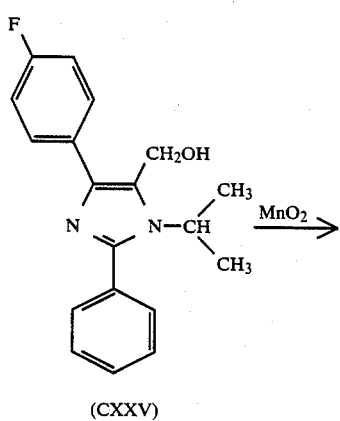
(CXXV)
-continued
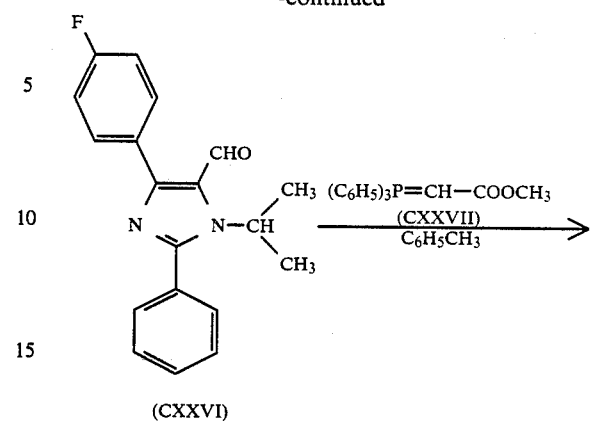
(CXXVI)
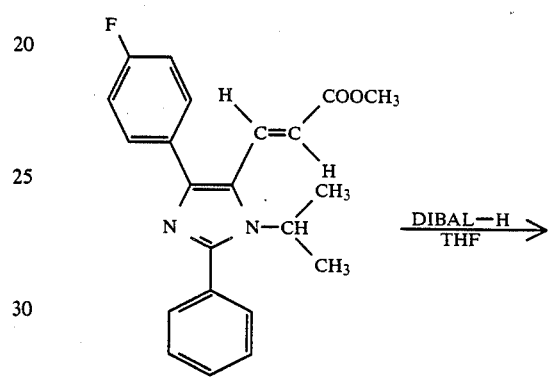
(CXXVIII)
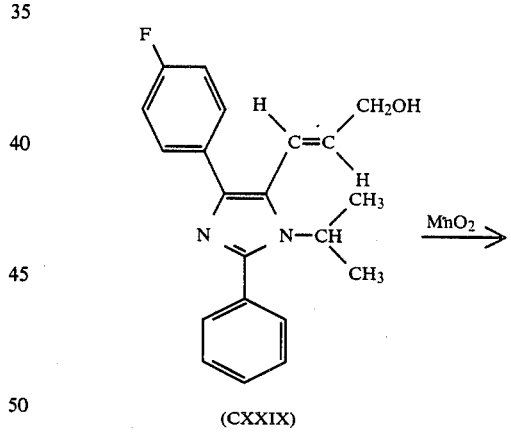
(CXXIX)
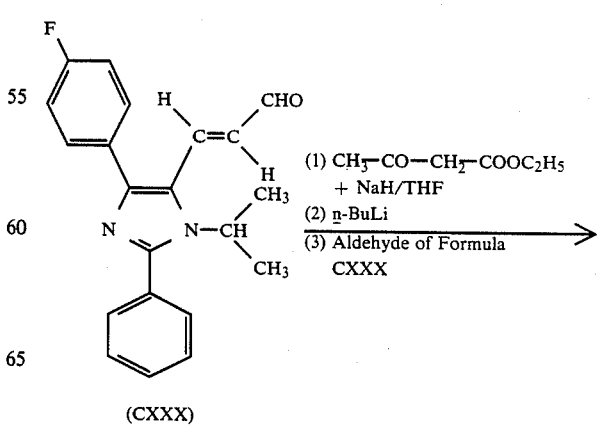
(CXXX)

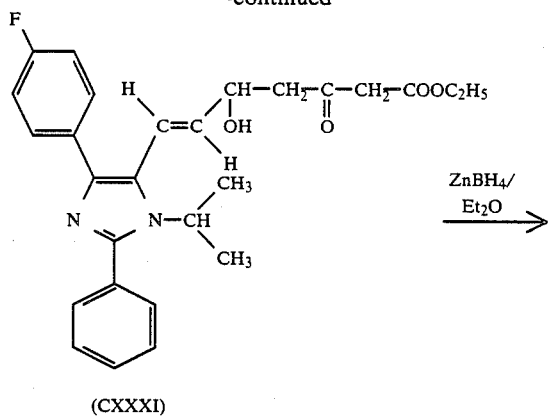

(CXXXI)

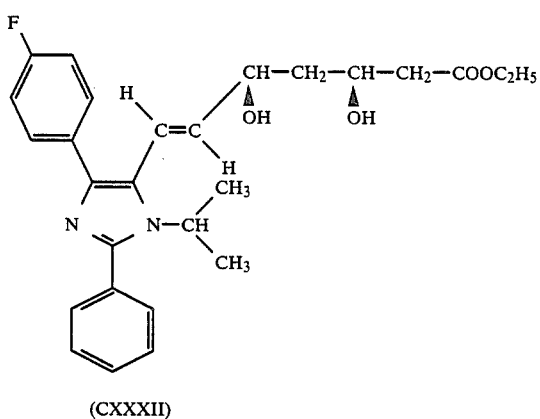

(CXXXII)

Step 1

(Reaction DH)

DL-4-Fluorophenylglycine (Compound CXIX)

800 ml. of saturated ammonium hydroxide solution is slowly added to 67.6 g. (1.59 moles) of lithium chloride, 268.8 g. (4.79 moles) of potassium hydroxide is slowly added portionwise (the addition being exothermic), and a solution of 18.4 g. (0.81 mole) of benzyltriethylammonium chloride in 400 ml. of methylene chloride is added, the reaction mixture being stirred at 20°–25° C. under nitrogen throughout. The reaction mixture is cooled to 0° C., ammonia is bubbled in for 30 minutes with vigorous stirring, and, over a period of 1 hour, a solution of 99.2 g. (0.80 mole) of 4-fluorobenzaldehyde in a mixture of 400 ml. of methylene chloride and 102 ml. of chloroform is added dropwise while simultaneously bubbling in ammonia, the reaction mixture being stirred at 0° C. throughout. Ammonia is bubbled in for 5 hours with stirring at 0° C., and the reaction mixture is allowed to warm to 20°–25° C. and stirred at 20°–25° C. for 16 hours. The aqueous phase is separated, washed three times with 150 ml. portions of methylen chloride, concentrated to one half of its volume at reduced pressure and filtered. The filtrate is acidified to pH 6.5 with concentrated hydrochloric acid, and the resulting fine precipitate is collected by filtration, washed with 1.5 l. of water, washed with 500 ml. of ethanol, washed with 200 ml. of diethyl ether and dried to obtain the product as a fine white solid (40 g.). A previous batch melted at about 280° C. (softened at about 260° C.).

Step 2

(Reaction CA)

N-Benzoyl-DL-4-fluorophenylglycine (Compound CXX)

A solution of 23.2 ml. (28.1 g., 200 mmoles) of benzoyl chloride in 70 ml. of dioxane and 500 ml. of 2N. sodium hydroxide solution (1 mole) are simultaneously added dropwise over a period of about 45 minutes to a solution of 25.35 g. (150 mmoles) of Compound CXIX in a mixture of 300 ml. of dioxane and 600 ml. of 2N. sodium hydroxide solution (1.2 moles) stirred at 0° C. under nitrogen, the additions being at rates such that the pH of the reaction mixture is always basic and the temperature is 0° C., the reaction being exothermic. The reaction mixture is stirred at 0° C. under nitrogen for 1 hour and warmed to 20°–25° C., the tetrahydrofuran is evaporated at reduced pressure, and the mixture is acidified to pH 1 with concentrated hydrochloric acid and cooled to 0° C. The obtained white solid is collected by filtration, washed with 2 l. of distilled water, air dried and vacuum dried to obtain the product as a white powder (31.4 g.). An analytical sample is recrystallized from ethanol/water. M.p. 169°–171° C.

Step 3

(Reaction CB)

(±)-N-[1-(4'-Fluorophenyl)-2-oxopropyl]benzamide (Compound CXXI)

50 ml. (618 mmoles) of pyridine and 50 ml. (530 mmoles) of acetic anhydride are added to 30 g. (110 mmoles) of Compound CXX, the mixture is stirred at 20°–25° C., 100 mg. (0.82 mmole) of 4-dimethylaminopyridine is added, the reaction mixture is stirred at 20°–25° C. for 45 minutes, 150 ml. (2.62 mmoles) of glacial acetic acid is added, and the reaction mixture is stirred at 130° C. for 3 hours and cooled to 20°–25° C., the reaction mixture being maintained under nitrogen throughout. The reaction mixture is cooled to 0°–5° C., 100 ml. of methanol is added, and the reaction mixture is stirred at 0°–5° C. for 30 minutes and poured into 1.5 l. of ice water. The mixture is allowed to stand for 16 hours, and the precipitate is collected by filtration, washed with 2 l. of distilled water and air dried to obtain a yellow powder which is recrystallized from methanol to obtain the yellow crystalline product (8.6 g.), m.p. 134°–136° C. A second crop is obtained from the mother liquor by adding water and cooling (2.5 g.).

Step 4

(Reaction CC)

(±)-N-[1-(4'-Fluorophenyl)-2-(1'-methylethyl)iminopropyl]-benzamide (Compound CXXII)

100 mg. (0.53 mmole) of p-toluenesulfonic acid. monohydrate is added to a solution of 5.42 g. (20.0 mmoles) of Compound CXXI and 8.2 ml. (5.69 g., 96.3 mmoles) of isopropylamine in 100 ml. of benzene and 25 ml. of methylene chloride, 25 g. (208 mmoles) of anhydrous magnesium sulfate is added, the reaction mixture is stirred at 20°–25° C. under nitrogen for 48 hours, an additional 16.4 ml. (11.38 g., 192.6 mmoles) of isopropylamine and 50 g. (415 mmoles) of anhydrous magnesium sulfate are added, the reaction mixture is stirred at 20°–25° C. under nitrogen for 4 hours, an additional 10 g. (42 mmoles) of anhydrous magnesium sulfate is added, and the reaction mixture is stirred at 20°–25° C. under nitrogen for 64 hours and filtered. The solid is washed with methylene chloride, the washing is combined with the filtrate, and the combined filtrate and washing is evaporated at reduced pressure to obtain the crude product as a yellow oil (about 7.5 g.).

Step 5

(Reaction CD)

4-(4′-Fluorophenyl)-5-methyl-1-(1′-methylethyl)-2-phenyl-1H-imidazole (Compound CXXIII)

A solution of about 7.5 g. (≦20 mmoles) of crude Compound CXXII from

Step 4 in 50 ml. of chloroform is added over a 30 minute period to 8.12 g. (39 mmoles) of phosphorus pentachloride in 100 ml. of chloroform stirred at −30° C., and the reaction mixture is allowed to warm to 20°–25° C., stirred at 20°–25° C. for 16 hours and cooled to 0° C., the reaction mixture being stirred under nitrogen throughout. 10 ml. of water is added, the mixture is stirred for 5 minutes, and 200 ml. of 2N. sodium hydroxide solution is added. The organic phase is separated, and the aqueous phase is extracted with chloroform. The chloroform extract and the organic phase are combined, washed twice with saturated sodium chloride solution, dried over anhydrous magnesium sulfate, filtered and evaporated at reduced pressure to a tan solid. The tan solid is recrystallized from benzene to obtain the product as a white solid (2.33 g.). A second crop is obtained from the mother liquor (200 mg.). An analytical sample is recrystallized from aqueous ethanol. M.p. 161°–162° C.

Step 6

(Reaction CE)

5-Acetoxymethyl-4-(4′-fluorophenyl)-1-(1′-methylethyl)-2-phenyl-1H-imidazole (Compound CXXIV)

3.5 g. (7.9 mmoles) of lead tetraacetate is added to a solution of 2.30 g. (7.81 mmoles) of Compound CXXIII in 300 ml. of dry benzene, and the reaction mixture is refluxed under nitrogen for 3 hours, an additional 0.35 g. (0.79 mmole) of lead tetraacetate is added, the reaction mixture is refluxed under nitrogen for 30 minutes, an additional 0.70 g. (1.58 mmoles) of lead tetraacetate is added, and the reaction mixture is refluxed under nitrogen for 1 hour, cooled, filtered and evaporated at reduced pressure to obtain the crude product as a tan gum (3.59 g.).

Step 7

(Reaction CF)

4-(4′-Fluorophenyl)-1-(1′-methylethyl)-2-phenyl-1H-imidazole-5-methanol (Compound CXXV)

100 ml. of 2N. sodium hydroxide solution (200 mmoles) is added to a solution of 3.59 g. (≦7.81 mmoles) of crude Compound CXXIV (from Step 6) in 100 ml. of ethanol, the reaction mixture is stirred at 20°–25° C. under nitrogen for 16 hours, the ethanol is evaporated at reduced pressure, 200 ml. of water is added, the mixture is stirred for 2 minutes, and the insoluble solid is collected by filtration, washed with 200 ml. of water (until the washings are pH 7) and dried to obtain the crude product as a yellow solid (1.88 g.). An analytical sample is recrystallized from aqueous ethanol. M.p. 190°–193° C.

Step 8

(Reaction CG)

4-(4′-Fluorophenyl)-1-(1′-methylethyl)-2-phenyl-1H-imidazole-5-carboxaldehyde (Compound CXXVI)

10 g. (115 mmoles) of activated manganese dioxide is added to a solution of 1.55 g. (5.0 mmoles) of Compound CXXV in 50 ml. of tetrahydrofuran, and the reaction mixture is stirred at 20°–25° C. under nitrogen for 16 hours and filtered. The solid is washed with 100 ml. of tetrahydrofuran, and the washing and filtrate are combined and evaporated at reduced pressure to obtain a yellow oil which is vacuum dried to obtain a yellow solid. The yellow solid is recrystallized from diethyl ether/hexane to obtain the yellow crystalline product (1.2 g.), m.p. 130°–134° C.

Step 9

(Reaction CK)

Methyl (E)-3-[4′-(4″-fluorophenyl)-1′-(1″-methylethyl)-2′-phenyl-1H-imidazol-5′-yl]propenoate (Compound CXXVIII)

2.004 g. (6.0 mmoles) of (carbomethoxymethylene)triphenylphosphorane (Compound CXXVII) is added to a solution of 1.23 g. (4.0 mmoles) of Compound CXXVI in 25 ml. of dry toluene, the reaction mixture is refluxed under nitrogen for 5 hours and stirred at 20°–25° C. under nitrogen for 16 hours, an additional 200 mg. (0.6 mmole) of Compound CXXVII is added, and the reaction mixture is refluxed under nitrogen for 1 hour, allowed to cool, evaporated at reduced pressure to about one-half of its volume and flash chromatographed on 150 g. of 230–400 mesh A.S.T.M. silica gel utilizing 1:1 diethyl ether/hexane as the eluant to obtain the product as a pale yellow solid (1.22 g.). An analytical sample is recrystallized from diethyl ether. M.p. 129°–131° C.

Step 10

(Reaction CL)

(E)-3-[4′-(4″-Fluorophenyl)-1′-(1″-methylethyl)-1H-imidazol-5′-yl]prop-2-en-1-ol (Compound CXXIX)

10 ml. of 1.5M. diisobutylaluminum hydride/toluene (15 mmoles) is added dropwise over a period of 5 minutes to a solution of 1.092 g. (3.0 mmoles) of Compound CXXVIII in 50 ml. of dry tetrahydrofuran stirred at 0° C. under nitrogen, and the reaction mixture is stirred at 0° C. under nitrogen for 2 hours and quenched with 0.5 ml. of saturated ammonium chloride solution. 5 ml. of water is added to dissolve the precipitate, 100 ml. of saturated sodium chloride solution and 50 ml. of 10% sodium hydroxide solution are added, the organic phase is separated, the aqueous phase is extracted three times with 50 ml. portions of diethyl ether, and the organic phase and the three diethyl ether extracts are combined, washed with 100 ml. of saturated sodium chloride solution, dried over anhydrous magnesium sulfate, filtered and evaporated at reduced pressure to obtain the product as a colorless oil which solidifies upon standing (910 mg.).

Step 11

(Reaction CM)

(E)-3-[4'-(4''-Fluorophenyl)-1'-(1'''-methylethyl)-2'-phenyl-1H-imidazol-5'-yl]prop-2-enal (Compound CXXX)

8 g. (92 mmoles) of activated manganese dioxide is added to a solution of 900 mg. (2.68 mmoles) of Compound CXXIX in 100 ml. of 1:1 diethyl ether/tetrahydrofuran, and the reaction mixture is stirred at 20°-25° C. under nitrogen for 1 hour and filtered through a pad of Celite. The solid is washed with 100 ml. of diethyl ether and washed with 100 ml. of tetrahydrofuran, the two washing are combined with the filtrate, and the combined washings and filtrate are evaporated at reduced pressure to obtain a yellow oil (740 mg.) which solidifies upon standing. The solid is recrystallized from diethyl ether to obtain the product as yellow needles (405 mg.). The residue from the mother liquor is recrystallized from aqueous ethanol to obtain a second crop (74 mg.) and a third crop (55 mg.). Additional product may be obtained by chromatographing the residue from the mother liquor from the third crop on 10 g. of silica gel utilizing 2:1 diethyl ether/hexane as the eluant (44 mg.).

Step 12

(Reaction I)

Ethyl (±)-(E)-7-[4'-(4''-fluorophenyl)-1'-(1'''-methylethyl)-2'-phenyl-1H-imidazol-5'-yl]-5-hydroxy-3-oxohept-6-enoate (Compound CXXXI)

21.12 mg. of 50% sodium hydride/mineral oil (0.44 mmole) is washed with 3 ml. of hexane, the liquid is decanted, 5 ml. of dry tetrahydrofuran is added, the suspension is cooled to $-15°$ C., 51 µl. (52 mg., 0.40 mmole) of ethyl acetoacetate is added via syringe, the reaction mixture is stirred at $-15°$ C. for 1.5 hours, allowed to warm to 0° C., stirred at 0° C. for 1 hour and cooled to $-15°$ C., 0.31 ml. of 1.6M. n-butyllithium/hexane (0.50 mmole) is added with stirring at $-15°$ C., the reaction mixture is stirred at $-15°$ C. for 10 minutes, a solution of 66.8 mg. (0.20 mmole) of Compound CXXX in 3 ml. of dry tetrahydrofuran is added dropwise with stirring at $-15°$ C., and the reaction mixture is stirred at $-15°$ C. for 15 minutes, the reaction mixture being maintained under nitrogen throughout. The reaction mixture is quenched at $-15°$ C. with 5 drops of saturated ammonium chloride solution, the tetrahydrofuran is evaporated at reduced pressure, diethyl ether and saturated sodium chloride solution are added, and the organic layer is separated, washed twice with 25 ml. portions of saturated sodium chloride solution, dried over anhydrous magnesium sulfate, filtered and evaporated at reduced pressure to obtain a gum (92 mg.). The gum is chromatographed on 5 g. of 230-400 mesh A.S.T.M. silica gel utilizing 9:1 diethyl ether/hexane as the eluant to obtain the product as a pale yellow gum (39.1 mg.).

The product is a racemate that may be resolved by conventional means to obtain the 5R and 5S enantiomers.

Step 13

(Reaction J)

Ethyl (±)-erythro-(E)-3,5-dihydroxy-7-[4'-(4''-fluorophenyl)-1'-(1'''-methylethyl)-2'-phenyl-1H-imidazol-5'-yl]hept-6-enoate (Compound CXXXII)

A solution of 39 mg. (0.084 mmole) of Compound CXXXI in 1 ml. of anhydrous diethyl ether is added dropwise via syringe over a period of 5 minutes to 2.4 ml. of 0.15M. zinc borohydride/diethyl ether (0.36 mmole) stirred at $-65°$ C. under nitrogen, and the reaction mixture is stirred at $-65°$ C. under nitrogen for 2 hours and quenched at $-65°$ C. with 0.5 ml. of methanol. The mixture is stirred for 3 minutes, 1 ml. of water is added, the mixture is allowed to warm to 20°-25° C., 10 ml. of very dilute acetic acid is added, 10 ml. of diethyl ether is added, and the organic phase is separated, washed twice with 20 ml. portions of saturated sodium chloride solution, dried over anhydrous magnesium sulfate, filtered and evaporated at reduced pressure to a yellow oil. The yellow oil is chromatographed on 10 g. of 230-400 mesh A.S.T.M. silica gel utilizing 30% ethyl acetate/chloroform as the eluant. The fractions containing the product (as indicated by thin layer chromatography) are combined and evaporated at reduced pressure, and the obtained pale yellow oil is vacuum dried to obtain the product as a solid foam (31 mg.). N.M.R. (CDCl$_3$): 1.28 (t, 3H), 1.48 (d, 6H), 1.56 (m, 2H), 2.46 (d, 2H), 4.18 (q, 2H), 4.21 (bm, 1H), 4.47 (bm, 1H), 4.59 (m, 1H), 5.78 (dd, 1H), 6.7 (d, 1H), 6.98 (t, 2H), 7.4-7.7 (m, 7H)

The product is a mixture of the erythro and threo racemates wherein the ratio of the former to the latter is about 17:3, which mixture may be separated by conventional means. The principal product, the erythro racemate, may be resolved into two optically pure enantiomers, the 3R,5S and 3S,5R enantiomers, of which the former is preferred. The minor product, the threo racemate, may be resolved to obtain the 3R,5R and 3S,5S enantiomers. The use of a nonstereoselective reduction would afford a mixture of all four stereoisomers wherein the ratio of the erythro stereoisomers to the threo stereoisomers ranges from 3:2 to 2:3.

EXAMPLE 4

Sodium (±)-erythro-(E)-3,5-dihydroxy-7-[4'-(4''-fluorophenyl)1'-(1'''-methylethyl)-2'-phenyl-1H-imidazol-5'-yl]hept-6-enoate (Reaction AA)

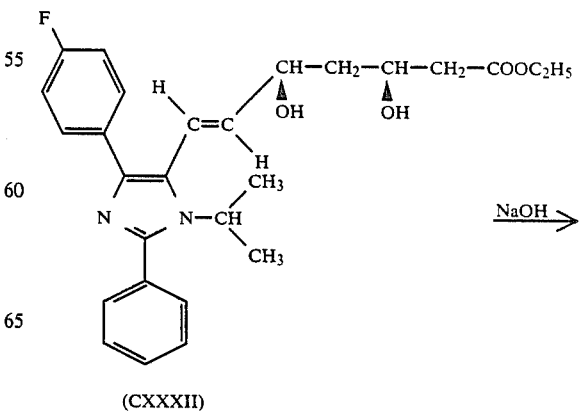

(CXXXII)

-continued

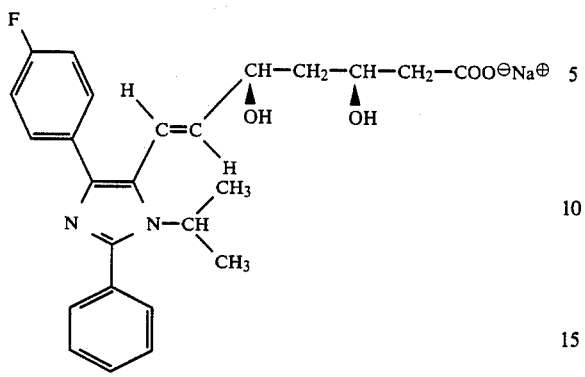

(CXXXIII)

0.04 ml. of 0.5N. sodium hydroxide solution (0.02 mmole) is added to a solution of 10 mg. (0.0214 mmole) of Compound CXXXII in 1 ml. of ethanol and 10 drops of water, the reaction mixture is stirred at 20°-25° C. under nitrogen for 1 hour, the ethanol is evaporated at reduced pressure, 0.5 ml. of water is added, and the mixture is extracted three times with 5 ml. portions of diethyl ether. The aqueous phase is lyophilized to obtain the product as a pale yellow solid (9.8 mg.).

N.M.R. (CDCl$_3$ +CD$_3$OD): 1.45 (d, 6H), 1.55 (m, 2H), 2.35 (m, 2H), 4.14 (bm, 1H), 4.40 (bm, 1H), 4.57 (m, 1H), 5.75 (dd, 1H), 6.67 (d, 1H), 6.98 (t, 2H), 7.4–7.7 (m, 7H)

The product is a mixture of the erythro and threo racemates wherein the ratio of the former to the latter is about 17:3, which mixture may be separated by conventional means. The principal product, the erythro racemate, may be resolved into two optically pure enantiomers, the 3R,5S and 3S,5R enantiomers, of which the former is preferred. The minor product, the threo racemate, may be resolved to obtain the 3R,5R and 3S,5S enantiomers. The use of a starting material synthesized by using a non-stereoselective reduction in Step 13 of Example 3 would afford a mixture of all four stereoisomers wherein the ratio of the erythro stereoisomers to the threo stereoisomers ranges from 3:2 to 2:3.

EXAMPLE 5

Ethyl (±)-(E)-3,5-dihydroxy-7-[1'-(4''-fluorophenyl)-4'-1''-methylethyl)-2'-phenyl-1H-imidazol-5'-yl]hept-6-enoate hydrochloride

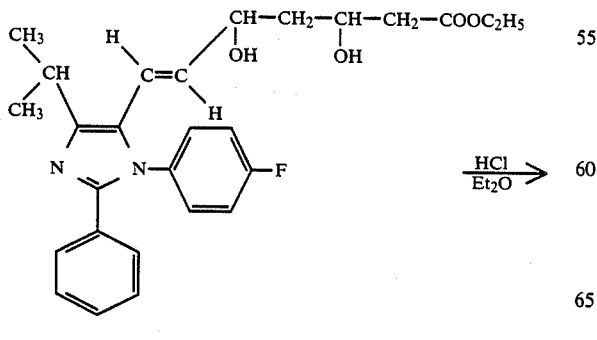

(CXXXIV)

-continued

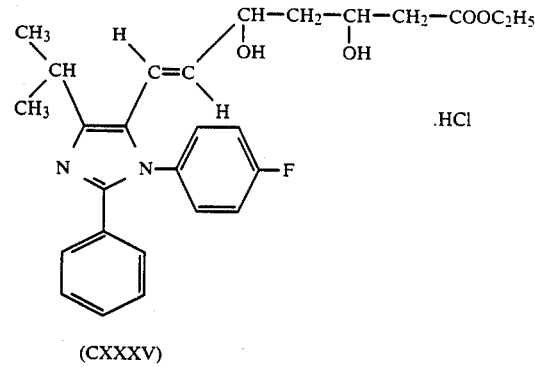

(CXXXV)

Hydrogen chloride is bubbled for 10 minutes through a solution of 18.5 mg. of Compound CXXXIV wherein the ratio of the erythro racemate to the threo racemate is about 7:3 in diethyl ether stirred at 20°-25° C., the diethyl ether is evaporated at reduced pressure, the resulting gum is dissolved in methylene chloride and the methylene chloride is evaporated at reduced pressure to obtain the product as a yellow foam, m.p. 85°-95° C.

The product is a mixture of the erythro and threo racemates wherein the ratio of the former to the latter is about 7:3.

EXAMPLE 6

Ethyl (±)-(E)-7-[1'-(4''-fluorophenyl)-4'-(1''-methylethyl)-2'-phenyl-1H-imidazol-5'-yl]—3-hydroxy-5-oxohept-6-enoate

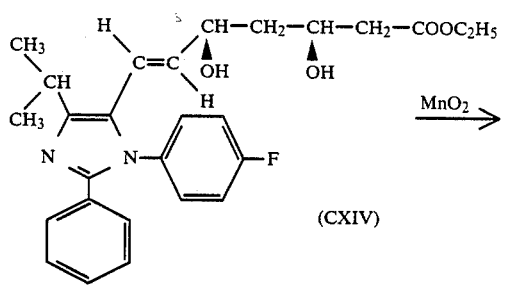

(CXIV)

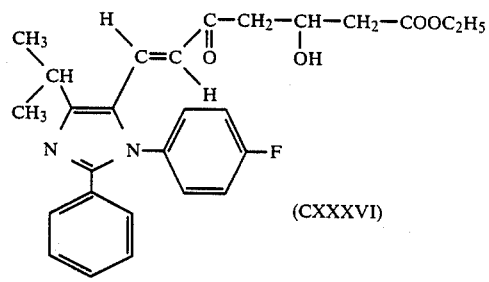

(CXXXVI)

A solution of 200 mg. (0.43 mmole) of Compound CXIV in 10 ml. of tetrahydrofuran is stirred with 200 mg. (2.3 mmoles) of activated manganese dioxide for 40 minutes at 20°-25° C., the reaction mixture is filtered, and the filtrate is evaporated at reduced pressure. The residue is dissolved in a mixture of diethyl ether and methylene chloride, and hexane is added to crystallize the product, m.p. 120°-121° C.

TABLE I

Examples 7-48
The following compounds of Groups IAa, ICa and IDa may be synthesized by the processes set forth above:

| | $R_1$ | $R_2$ | $R_3$ | X | $R_{13}$ | $R_{14}$ | Isomers | M.p. |
|---|---|---|---|---|---|---|---|---|
| Ex. 7 | i-$C_3H_7$ | 3,5-dimethylphenyl | phenyl | (E)—CH=CH— | H | $C_2H_5$ | E | 73°–75° C. |
| Ex. 8 | i-$C_3H_7$ | 3,5-dimethylphenyl | phenyl | (E)—CH=CH— | H | Na⊕ | E | 230°–235° C. (dec.) |
| Ex. 9 | i-$C_3H_7$ | phenyl | phenyl | (E)—CH=CH— | H | $C_2H_5$ | E:T = ~12:1 | 104°–110° C. |
| Ex. 10 | i-$C_3H_7$ | phenyl | phenyl | (E)—CH=CH— | H | Na⊕ | E | 215° C. (dec.) |
| Ex. 11 | i-$C_3H_7$ | 4-fluorophenyl | phenyl | —$CH_2CH_2$— | H | Na⊕ | E | 75°–85° C. |
| Ex. 12 | i-$C_3H_7$ | 4-fluorophenyl | phenyl | —$CH_2CH_2$— | H | $C_2H_5$ | E | Foam |
| Ex. 13 | i-$C_3H_7$ | 4-bromophenyl | phenyl | (E)—CH=CH— | H | $C_2H_5$ | E | 132°–134° C. |
| Ex. 14 | i-$C_3H_7$ | 4-chlorophenyl | phenyl | (E)—CH=CH— | H | $CH_3$ | E | 132°–134° C. |
| Ex. 15 | i-$C_3H_7$ | 4-chlorophenyl | phenyl | (E)—CH=CH— | H | Na⊕ | E | 183°–205° C. |
| Ex. 16 | i-$C_3H_7$ | 4-bromophenyl | phenyl | (E)—CH=CH— | H | Na⊕ | E | 219°–226° C. |
| Ex. 17 | i-$C_3H_7$ | cyclohexyl | phenyl | (E)—CH=CH— | H | $C_2H_5$ | E | 102°–106° C. |
| Ex. 18 | i-$C_3H_7$ | 4-fluorophenyl | t-$C_4H_9$ | (E)—CH=CH— | H | $C_2H_5$ | E | Oil |
| Ex. 19 | i-$C_3H_7$ | 4-fluorophenyl | t-$C_4H_9$ | (E)—CH=CH— | H | Na⊕ | E | 215°–220° C. |
| Ex. 20 | i-$C_3H_7$ | 4-fluorophenyl | cyclohexyl | (E)—CH=CH— | H | $C_2H_5$ | E | 86°–88° C. |
| Ex. 21 | i-$C_3H_7$ | cyclohexyl | phenyl | (E)—CH=CH— | H | Na⊕ | E | 145°–155° C. |
| Ex. 22 | i-$C_3H_7$ | 4-fluorophenyl | cyclohexyl | (E)—CH=CH— | H | Na⊕ | E | 224°–227° C. |
| Ex. 23 | i-$C_3H_7$ | 3,5-dichlorophenyl | phenyl | (E)—CH=CH— | H | $CH_3$ | E:T = ~3:2 | 143°–145° C. |
| Ex. 24 | i-$C_3H_7$ | 3,5-dichlorophenyl | phenyl | (E)—CH=CH— | H | Na⊕ | E:T = ~3:2 | 219°–225° C. |
| Ex. 25 | i-$C_3H_7$ | 4-fluorophenyl | 4-phenylphenyl | (E)—CH=CH— | H | $C_2H_5$ | E | 177°–178° C. |
| Ex. 26 | i-$C_3H_7$ | 4-fluorophenyl | 4-phenylphenyl | (E)—CH=CH— | H | Na⊕ | E | 230°–235° C. |
| Ex. 27 | i-$C_3H_7$ | 4-fluorophenyl | adamantyl-1 | (E)—CH=CH— | H | $C_2H_5$ | E:T = 83:17 | Gum |
| Ex. 28 | i-$C_3H_7$ | 4-fluorophenyl | styryl | (E)—CH=CH— | H | $C_2H_5$ | E | 95°–97° C. |
| Ex. 29 | i-$C_3H_7$ | 4-fluorophenyl | i-$C_3H_7$ | (E)—CH=CH— | H | $C_2H_5$ | E:T = ~4:1 | Gum |
| Ex. 30 | i-$C_3H_7$ | 4-fluorophenyl | i-$C_3H_7$ | (E)—CH=CH— | H | Na⊕ | E:T = ~4:1 | 204°–205° C. (dec.) |
| Ex. 31 | 4-fluorophenyl | 4-fluorophenyl | phenyl | (E)—CH=CH— | H | $C_2H_5$ | E | 138°–139° C. |
| Ex. 32 | 4-fluorophenyl | 4-fluorophenyl | phenyl | (E)—CH=CH— | H | Na⊕ | E | 215°–220° C. (dec.) |
| Ex. 33 | i-$C_3H_7$ | 4-fluorophenyl | phenyl | (E)—CH=CH— | H | $CH_3$ | E | 156°–157.5° C. |
| Ex. 34 | i-$C_3H_7$ | 4-fluorophenyl | 4-trifluoromethylphenyl | (E)—CH=CH— | H | $C_2H_5$ | E | 109°–111° C. |
| Ex. 35 | i-$C_3H_7$ | 4-fluorophenyl | 4-methoxyphenyl | (E)—CH=CH— | H | $C_2H_5$ | E | 143°–145° C. |
| Ex. 36 | i-$C_3H_7$ | 4-fluorophenyl | 4-methoxyphenyl | (E)—CH=CH— | H | Na⊕ | E | 131° C. (dec.) |
| Ex. 37 | i-$C_3H_7$ | 4-fluorophenyl | 4-dimethylaminophenyl | (E)—CH=CH— | H | $C_2H_5$ | E | 155°–157° C. |
| Ex. 38 | i-$C_3H_7$ | 4-fluorophenyl | 4-dimethylaminophenyl | (E)—CH=CH— | H | Na⊕ | E | 217° C. (dec.) |
| Ex. 39 | i-$C_3H_7$ | 4-fluorophenyl | phenyl | (E)—CH=CH— | H | $CH_3$ | 3R,5S* | 139°–141° C. |
| Ex. 40 | i-$C_3H_7$ | 4-fluorophenyl | phenyl | (E)—CH=CH— | H | $CH_3$ | 3S,5S* | 149°–151° C. |
| Ex. 41 | i-$C_3H_7$ | 4-fluorophenyl | phenyl | (E)—CH=CH— | H | Na⊕ | 3S,5R* | >190° C. |
| Ex. 42 | i-$C_3H_7$ | 4-fluorophenyl | phenyl | (E)—CH=CH— | H | $CH_3$ | 3S,5R* | 137°–139° C. |
| Ex. 43 | i-$C_3H_7$ | 4-fluorophenyl | phenyl | (E)—CH=CH— | H | Na⊕ | 3S,5S* | >195° C. |
| Ex. 44 | i-$C_3H_7$ | 4-fluorophenyl | phenyl | (E)—CH=CH— | H | $CH_3$ | 3R,5R* | 151°–152° C. |
| Ex. 45 | i-$C_3H_7$ | 4-fluorophenyl | phenyl | (E)—CH=CH— | H | Na⊕ | 3R,5R* | >188° C. |
| Ex. 46 | i-$C_3H_7$ | 4-fluorophenyl | phenyl | (Z)—CH=CH— | H | Na⊕ | 3R,5S* | 188°–191° C. |
| Ex. 47 | i-$C_3H_7$ | 4-fluorophenyl | 4-methoxycarbonylphenyl | (E)—CH=CH— | H | $C_2H_5$ | E | 137°–138° C. |
| Ex. 48 | i-$C_3H_7$ | 4-fluorophenyl | 4-methoxycarbonylphenyl | (E)—CH=CH— | H | Na⊕ | E | 138° C. (dec.) |

E = erythro racemate (≧95% pure (except Ex. 12: ≧90% pure); balance, if any, threo racemate and/or impurities)
T = threo racemate
*≧98% enantiomerically pure

TABLE II

Examples 49-51
The following compounds of Group IAb may be synthesized by the processes set forth above:

| | $R_1$ | $R_2$ | $R_3$ | X | $R_{13}$ | Isomers | M.p. |
|---|---|---|---|---|---|---|---|
| Ex. 49 | i-$C_3H_7$ | 4-fluorophenyl | phenyl | (E)—CH=CH— | H | trans | 160°–164° C. |
| Ex. 50 | i-$C_3H_7$ | 4-fluorophenyl | phenyl | —$CH_2CH_2$— | H | trans | 209°–212° C. |
| Ex. 51 | i-$C_3H_7$ | 4-fluorophenyl | phenyl | (Z)—CH=CH— | H | 4R,6S* | 153°–155° C. | trans = trans racemate (≧95% pure)
*≧98% enantiomerically pure

TABLE III

Example 52
The following compound of Group IAc may be synthesized by the processes set forth above:

| | $R_1$ | $R_2$ | $R_3$ | X | Q | $R_{13}$ | $R_{14}$ | Isomers | M.p. |
|---|---|---|---|---|---|---|---|---|---|
| Ex. 52 | i-$C_3H_7$ | 4-fluorophenyl | phenyl | (E)—CH=CH— | CO | H | Na⊕ | Racemate | 135°–150° C. |

| N.M.R. DATA | |
|---|---|
| Ex. 8 (CDCl$_3$ + CD$_3$OD): | 1.35 (d (J = 7 Hz.), 6H), 1.35–1.70 (m, 2H), 2.26 (s, 6H), 2.10–2.40 (m, 2H), 3.15 (sp (J = 7 Hz.), 1H), 3.50 (water), 4.08 (m, 1H), 4.28 (m, 1H), 5.50 (dd (J$_1$ = 16 Hz., J$_2$ = 6 Hz.), 1H), 6.18 (d (J = 16 Hz.), 1H), 6.77 |

N.M.R. DATA

| | |
|---|---|
| Ex. 9 (CDCl$_3$): | (s, 2H), 7.00 (s, 1H), 7.15–7.35 (m, 5H)<br>1.25 (t (J = 1.5 Hz.), 3H), 1.36 (d, 6H), 1.6 (m, 2H), 2.45 (d, 2H), 3.15 (m, 1H), 3.17 (m, 1H), 3.7 (m, 1H), 4.15 (q (J = 1.5 Hz.), 2H), 4.20 (m, 1H), 4.33 (m, 1H), 5.47 (dd (J$_1$ = 1.5 Hz., J$_2$ = 2 Hz.), 1H), 6.20 (d (J = 3 Hz.), 1H), 7.10–7.45 (m, 10H) |
| Ex. 11 (CDCl$_3$): | 1.11 (d (J = 6 Hz.), 6H), 1.61 (m, 2H), 2.40 (bm, 6H), 2.88 (m, 1H), 3.46 (m, 1H), 3.95 (m, 1H), 7.1 (m, 9H) |
| Ex. 12 (CDCl$_3$): | 1.28 (t (J = 7 Hz.), 3H), 1.38 (d (J = 7 Hz.), 6H), 1.64 (bs, 6H), 2.42 (d (J = 7 Hz.), 2H), 2.58 (m, 1H), 3.7 (bs, 2H), 4.15 (q (J = 7 Hz.), 2H), 7.0–7.3 (m, 9H) |
| Ex. 15 (CD$_3$OD): | 1.32 (d (J = 7 Hz.), 6H), 1.4–1.8 (m, 2H), 2.2–2.4 (m, 2H), 3.22 (m, 1H), 3.93 (m, 1H), 4.25 (m, 1H), 5.58 (dd (J$_1$ = 6 Hz., J$_2$ = 16 Hz.), 1H), 6.22 (d (J = 16 Hz.), 1H), 7.1–7.5 (m, 9H) |
| Ex. 16 (CD$_3$OD): | 1.35 (d (J = 7 Hz.), 6H), 1.4–1.8 (m, 2H), 2.2–2.4 (m, 2H), 3.2 (m, 1H), 3.9 (m, 1H) 4.25 (m, 1H), 5.60 (dd (J$_1$ = 6 Hz., J$_2$ = 16 Hz.), 1H), 6.21 (d (J = 16 Hz.), 1H), 7.1–7.7 (m, 9H) |
| Ex. 18 (CDCl$_3$): | 1.19 (s, 9H), 1.25 (t (J = 7 Hz.), 3H), 1.30 (d (J = 7 Hz.), 6H), 1.4–1.9 (m, 2H), 2.43 (d (J = 6 Hz.), 2H), 2.8–3.2 (m, 2H), 3.6 (m, 1H), 4.1–4.3 (m, 2H), 4.11 (q (J = 7 Hz.), 2H), 5.20 (dd (J$_1$ = 7 Hz., J$_2$ = 16 Hz.), 1H), 5.88 (dd (J$_1$ = 1 Hz., J$_2$ = 16 Hz.), 1H), 7.0–7.3 (m, 4H) |
| Ex. 19 (CD$_3$OD): | 1.20 (s, 9H), 1.28 (d (J = 7 Hz.), 6H), 1.3–1.7 (m, 2H), 2.2–2.3 (m, 2H), 3.11 (m, 1H), 3.8 (m, 1H), 4.12 (m, 1H), 5.26 (dd (J$_1$ = 6 Hz., J$_2$ = 16 Hz.), 1H), 5.96 (d (J = 16 Hz.), 1H), 7.2–7.4 (m, 4H) |
| Ex. 21 (CD$_3$OD): | 1.1–2.1 (m, 12H), 1.22 (d (J = 7 Hz.), 6H), 2.3–2.5 (m, 2H), 3.12 (m, 1H), 3.9–4.2 (m, 2H), 4.50 (m, 1H), 5.82 (dd (J$_1$ = 6 Hz., J$_2$ = 16 Hz.), 1H), 6.65 (d (J = 16 Hz.), 1H), 7.4–7.5 (m, 5H) |
| Ex. 24 (CD$_3$OD): | 1.35 (d (J = 7 Hz.), 6H), 1.5–1.8 (m, 2H), 2.2–2.4 (m, 2H), 3.2 (m, 1H), 3.9–4.1 (m, 1H), 4.3 (m, 1H), 5.5–5.7 (m, 1H), 6.2–6.4 (m, 1H), 7.3 (m, 7H), 7.6 (m, 1H) |
| Ex. 26 (CD$_3$OD): | 1.38 (d (J = 7 Hz.), 6H), 1.5–1.8 (m, 2H), 2.3 (m, 2H), 3.33 (m, 1H), 3.95 (m, 1H), 4.27 (m, 1H), 5.56 (dd (J$_1$ = 6 Hz., J$_2$ = 16 Hz.), 1H), 6.23 (d (J = 16 Hz.), 1H), 7.2–7.6 (m, 13H) |
| Ex. 27 (CDCl$_3$): | 1.23 (t (J = 7 Hz.), 3H), 1.28 (d (J = 7 Hz.), 6H), 1.4–1.7 (m, 8H), 1.9 (m, 8H), 2.4 (m, 2H), 2.94 (m, 1H), 3.04 (m, 1H), 3.60 (m, 1H), 4.17 (q (J = 7 Hz.), 2H), 4.1–4.4 (m, 3H), 5.23 (dd (J$_1$ = 6 Hz., J$_2$ = 16 Hz.), 1H), 5.92 (d (J = 16 Hz.), 1H), 7.1–7.3 (m, 4H) |
| Ex. 29 (CDCl$_3$): | 1.1–1.3 (m, 15H), 1.4–1.7 (m, 2H), 2.4 (m, 2H), 2.70 (m, 1H), 3.08 (m, 1H), 3.7 (m, 2H), 4.17 (q (J = 7 Hz.), 2H), 4.2–4.4 (m, 2H), 5.20 (dd (J$_1$ = 7 Hz., J$_2$ = 16 Hz.), 1H), 6.14 (dd (J$_1$ = 1Hz., J$_2$ = 16 Hz.), 1H), 7.1–7.3 (m, 4H) |
| Ex. 32 (CD$_3$OD): | 1.2–1.7 (m, 2H), 2.2 (m, 2H), 3.8 (m, 1H), 4.2 (m, 1H), 5.41 (dd (J$_1$ = 7 Hz., J$_2$ = 16 Hz.), 1H), 6.43 (dd (J$_1$ = 1 Hz., J$_2$ = 16 Hz.), 1H), 7.1–7.4 (m, 11H), 7.6–7.8 (m, 2H) |
| Ex. 49 (CDCl$_3$ + CD$_3$SOCD$_3$): | 1.4 (d (J = 7 Hz.), 6H), 1.6–2.0 (m, 2H), 2.62 (d (J = 4 Hz.), 2H), 3.15 (m, 1H), 4.21 (m, 1H), 4.9 (bm, 1H), 5.2 (m, 1H), 5.5 (dd (J$_1$ = 16 Hz., J$_2$ = 7 Hz.), 1H), 6.28 (d, 1H), 7.1–7.4 (m, 9H) |
| Ex. 52 (CD$_3$OD): | 1.4 (d (J = 7.5 Hz.), 6H), 2.28 (m, 4H), 3.2 (m, 1H), 4.28 (m, 1H), 5.95 (d (J = 15 Hz.), 1H), 7.25 (m, 10H) |

OPTICAL ROTATION DATA
$[\alpha]_D^{25}$

| | | |
|---|---|---|
| Ex. 39 | +41.51° | (c = 2.2885, CH$_3$OH) |
| Ex. 40 | −2.42° | (c = 0.62, CH$_3$OH) |
| Ex. 41 | −17.14° | (c = 0.42, CH$_3$OH) |
| Ex. 42 | −37.03° | (c = 0.64, CH$_3$OH) |
| Ex. 43 | +9.07° | (c = 0.54, CH$_3$OH) |
| Ex. 44 | +3.70° | (c = 0.46, CH$_3$OH) |
| Ex. 45 | −7.04° | (c = 0.27, CH$_3$OH) |
| Ex. 46 | +113.89° | (c = 0.36, CH$_3$OH) |
| Ex. 51 | +231.25° | (c = 0.48, CH$_3$OH) |

Each of the compounds identified by an E in the Isomers column is at least 95% pure (at least 90% in the case of Example 12) erythro racemate, the balance being the corresponding threo racemate and/or other impurities. Any threo racemate present may be separated therefrom. Each erythro racemate except those of Examples 11 and 12 may be resolved to obtain the 3R,5S and 3S,5R enantiomers, of which in each case the former is preferred. The erythro racemates of Examples 11 and 12 may be resolved to obtain the 3R,5R and 3S,5S enantiomers of which the former is preferred. The mixtures of Examples 9, 23, 24, 27, 29 and 30 may be separated to obtain the erythto and threo racemates, each of which may be resolved to obtain the 3R,5S and 3S,5R enantiomers from the former and the 3R,5R and 3S,5S enantiomers from the latter, the former being preferred in each case.

The compound of Example 49 may be resolved to obtain the 4R,6S and 4S,6R enantiomers, that of Example 50 may be resolved to obtain the 4R,6R and 4S,6S enantiomers, and that of Example 52 may be resolved to obtain the 3R and 3S enantiomers, the former being preferred in each case.

Each of the compounds of the examples wherein Z is a group of Formula a or c wherein R$_{14}$ is a cation may be converted into the corresponding compounds wherein R$_{14}$ is hydrogen or a different cation M, particularly the latter, especially M', by the processes set forth in Reaction Schemes IV and V. Each of the compounds of the examples except those wherein Z is a group of Formula a or c wherein R$_{14}$ is a cation and the one already in pharmaceutically acceptable acid addition salt form may be converted into pharmaceutically acceptable acid addition salt form as also set forth in Reaction Schemes IV and V.

Each of Examples 1–52 (including each of the possible optical isomers of each example) may be administered to an animal, e.g., a larger primate, to inhibit cholesterol biosynthesis and thereby lower the blood cholesterol level for, for example, the treatment of atherosclerosis and hyperlipoproteinemia. The dosages are those set forth supra.

Throughout the specification, the term "reduced pressure" denotes aspirator pressure. Where no solvent is specified in connection with a solution, the solvent is water, and all solvent mixtures are by volume. When a reaction is carried out under nitrogen or argon, dry nitrogen or argon, as the case may be, is used to maintain anhydrous conditions (except where the reaction medium contains water).

All nuclear magnetic resonance spectra were taken at ambient temperature on a 200 MHz. spectrometer. All chemical shifts are given in p.p.m. (δ) relative to tetramethylsilane, and where a single δ value is given for anything other than a sharp singlet, it is its center point. In the N.M.R. data:

bm=broad multiplet
bs=broad singlet
d=doublet
dd=doublet of a doublet
m=multiplet
q=quartet
s=singlet
sp=septet
t=triplet

What is claimed is:

1. A compound of the formula

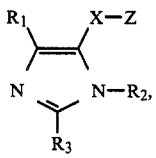

or a pharmaceutically acceptable acid addition salt thereof, wherein $R_1$ is $C_{1-6}$alkyl not containing an asymmetric carbon atom, $C_{3-7}$cycloalkyl, adamantyl-1 or

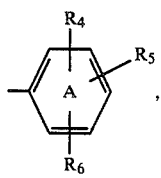

wherein $R_4$, $R_5$ and $R_6$ are as defined below, $R_2$ is $C_{1-6}$alkyl not containing an asymmetric carbon atom, $C_{3-7}$cycloalkyl, adamantyl-1 or

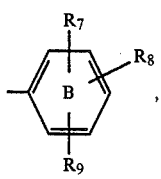

wherein $R_7$, $R_8$ and $R_9$ are as defined below, $R_3$ is hydrogen, $C_{1-6}$alkyl not containing an asymmetric carbon atom, $C_{3-7}$cycloalkyl, adamantyl-1, styryl or

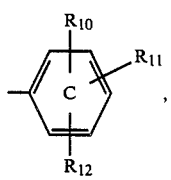

wherein $R_{10}$, $R_{11}$ and $R_{12}$ are as defined below, —$(CH_2)_m$—, —CH=CH—, —CH=CH-$CH_2$— or —$CH_2$—CH=CH—, wherein m is 0, 1, 2 or 3, and

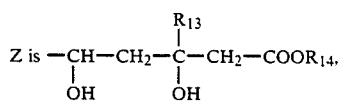

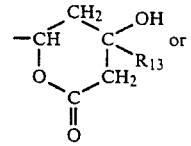

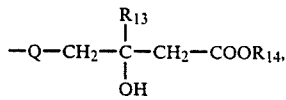

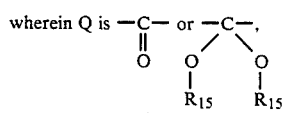

wherein each $R_{15}$ is primary or secondary $C_{1-6}$alkyl not containing an asymmetric carbon atom, the two $R_{15}$'s being the same, or the two $R_{15}$'s taken together are —$(CH_2)_q$—, wherein q is 2 or 3, $R_{13}$ is hydrogen or $C_{1-3}$alkyl, and $R_{14}$ is hydrogen, $R_{16}$ or M, wherein $R_{16}$ is a physiologically acceptable ester group, and M is a cation, with the proviso that Z may be

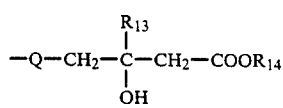

only when (i) X is —CH=CH— or —$CH_2$—CH=CH—, (ii) $R_{13}$ is $C_{1-3}$alkyl or (iii) both (i) and (ii), wherein each of $R_4$, $R_7$ and $R_{10}$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, bromo, phenyl, phenoxy or benzyloxy, each of $R_5$, $R_8$ and $R_{11}$ is independently hydrogen, $C_{1-3}$alkyl, $C_{1-3}$alkoxy, trifluoromethyl, fluoro, chloro, bromo, —COOR$_{17}$, —N(R$_{19}$)$_2$, phenoxy or benzyloxy, wherein $R_{17}$ is hydrogen, $R_{18}$ or M, wherein $R_{18}$ is $C_{1-3}$alkyl, n-butyl, i-butyl, t-butyl or benzyl, and M is as defined above, and each $R_{19}$ is independently $C_{1-6}$alkyl not containing an asymmetric carbon atom, and each of $R_6$, $R_9$ and $R_{12}$ is independently hydrogen, $C_{1-2}$alkyl, $C_{1-2}$alkoxy, fluoro or chloro, with the provisos that not more than one substituent on each of Rings A, B and C. independently is trifluoromethyl, not more than one substituent on each of Rings A, B and C. independently is phenoxy, and not more than one substituent on each of Rings A, B and C. independently is benzyloxy, with the provisos that (1) when Z is

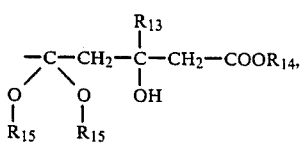

the compound is in free base form and either (i) $R_{14}$ is $R_{16}$ and each $R_{17}$ is independently $R_{18}$ or (ii) $R_{14}$ is M and each $R_{17}$ is independently $R_{18}$ or M and (2) when (i) $R_{14}$ or at least one $R_{17}$ is M or (ii) $R_{14}$ and at least one $R_{17}$ are M, the compound is in free base form.

2. A compound according to claim 1, or a pharmaceutically acceptable acid addition salt thereof, wherein each M is independently a pharmaceutically acceptable cation.

3. A compound according to claim 2, or a pharmaceutically acceptable acid addition salt thereof, wherein $R_1$ is $C_{1-6}$alkyl not containing an asymmetric carbon atom, $C_{3-7}$cycloalkyl or adamantyl-1, and $R_2$ is

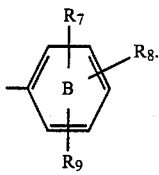

4. A compound according to claim 3, or a pharmaceutically acceptable acid addition salt thereof, wherein Z is

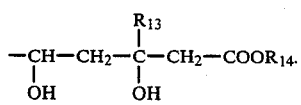

5. A compound according to claim 4, or a pharmaceutically acceptable acid addition salt thereof, wherein $R_1$ is $C_{1-6}$alkyl not containing an asymmetric carbon atom, $R_3$ is $C_{1-6}$alkyl not containing an asymmetric carbon atom, cyclohexyl or

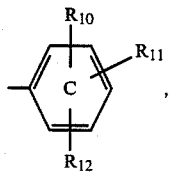

$R_7$ is hydrogen, $C_{1-3}$alkyl, fluoro, chloro or bromo, $R_8$ is hydrogen, $C_{1-2}$alkyl, fluoro or chloro, $R_9$ is hydrogen or methyl, $R_{13}$ is hydrogen or methyl, $R_{14}$ is hydrogen, $C_{1-3}$alkyl, n-butyl, i-butyl, t-butyl, benzyl or M, and X is —$CH_2CH_2$— or —CH=CH—.

6. A compound according to claim 4, or a pharmaceutically acceptable acid addition salt thereof, wherein $R_1$ is $C_{1-3}$alkyl, n-butyl, i-butyl, $R_3$ is

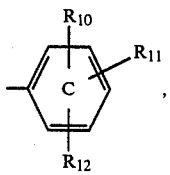

$R_{13}$ is hydrogen, $R_{14}$ is hydrogen, $C_{1-3}$alkyl, or M, and X is (E)—CH=CH—.

7. A compound according to claim 6, or a pharmaceutically acceptable acid addition salt thereof, wherein $R_{10}$ is hydrogen $C_{1-3}$alkyl, $C_{1-2}$alkoxy, trifluoromethyl, fluoro, chloro, bromo or phenyl, $R_{11}$ is hydrogen, $C_{1-2}$alkyl, fluoro, chloro, bromo, —COOR$_{17}'$ is hydrogen, $C_{1-3}$alkyl or M, and wherein $R_{17}'$ or —N($R_{19}'$)$_2$, each $R_{19}'$ is independently $C_{1-2}$alkyl, $R_{12}$ is hydrogen or methyl, and $R_{14}$ is hydrogen, $C_{1-2}$alkyl or M.

8. A compound according to claim 7, or a pharmaceutically acceptable acid addition salt thereof, wherein $R_1$ is $C_{1-3}$alkyl, $R_7$ is hydrogen, methyl or fluoro, $R_8$ is hydrogen or methyl, $R_{10}$ is hydrogen, methyl or fluoro, and $R_{11}$ is hydrogen or methyl.

9. A compound according to claim 8, or a pharmaceutically acceptable acid addition salt thereof, wherein $R_9$ is hydrogen, and $R_{12}$ is hydrogen.

10. A compound according to claim 8 wherein $R_{14}$ is a pharmaceutically acceptable cation.

11. A compound according to claim 10 wherein the hydroxy groups in the 3- and 5-positions of the group of the formula

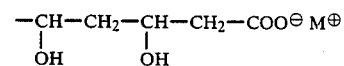

have the erythro configuration.

12. A compound according to claim 11 having the formula

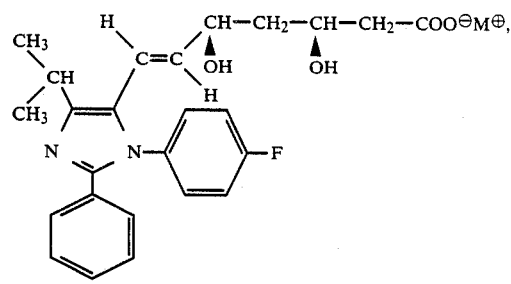

wherein M⊕ is a pharmaceutically acceptable cation.

13. A compound according to claim 12 having the formula

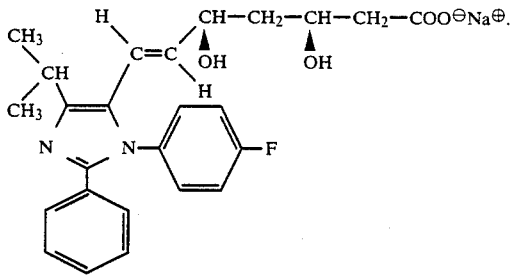

14. The 3R,5S enantiomer of the compound according to claim 13.

15. A compound according to claim 11 having the formula

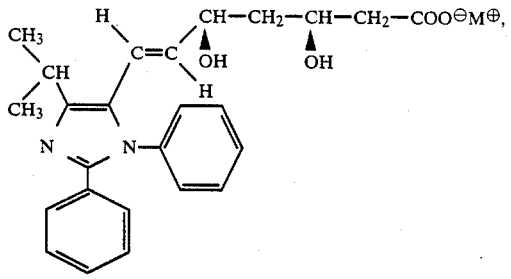

wherein M⊕ is a pharmaceutically acceptable cation.

16. A compound according to claim 15 having the formula

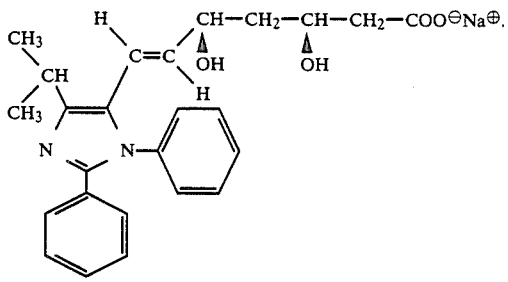

17. A compound according to claim 3, or a pharmaceutically acceptable acid addition salt thereof, Wherein Z is

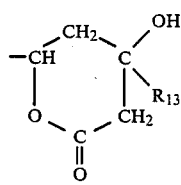

18. A compound according to claim 3, or a pharmaceutically acceptable acid addition salt thereof, wherein Z is

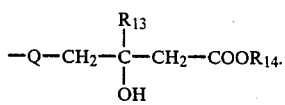

19. A compound according to claim 2, or a pharmaceutically acceptable acid addition salt thereof, wherein $R_1$ is

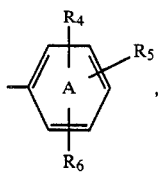

$R_2$ is $C_{1-6}$alkyl not containing an asymmetric carbon atom, $C_{3-7}$cycloalkyl or adamantyl-1.

20. A compound according to claim 19, or a pharmaceutically acceptable acid addition salt thereof, wherein Z is

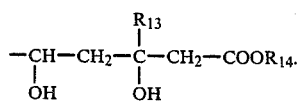

21. A compound according to claim 2, or a pharmaceutically acceptable acid addition salt thereof, wherein $R_1$ is

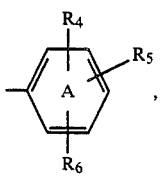

and $R_2$ is

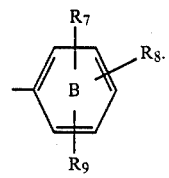

22. A compound according to claim 2, or a pharmaceutically acceptable acid addition salt thereof, wherein $R_1$ is $C_{1-6}$alkyl not containing an asymmetric carbon atom, $C_{3-7}$cycloalkyl or adamantyl-1, and $R_2$ is $C_{1-6}$alkyl not containing an asymmetric carbon atom, $C_{3-7}$cycloalkyl or adamantyl-1.

23. A pharmaceutical composition comprising an effective amount of a compound according to claim 2, or a pharmaceutically acceptable acid additon salt thereof, and a pharmaceutically acceptable carrier, said effective amount being an amount effective for inhibiting cholesterol biosynthesis in a mammal.

24. A method of inhibiting cholesterol biosynthesis comprising adminstering to a mammal in need of such treatment an effective amount of a compound according to claim 2, or a pharmaceutically acceptable acid addition salt thereof, said effective amount being an amount effective for inhibiting cholesterol biosynthesis.

25. A method of treating atherosclerosis comprising adminstering to a mammal in need of such treatment an effective amount of a compound according to claim 2, or a pharmaceutically acceptable acid addition salt thereof, said effective amount being an amount effective for the treatment of atherosclerosis.

26. A method of treating atherosclerosis according to claim 25 comprising administering to a mammal in need of such treatment an effective amount of a compound of the formula

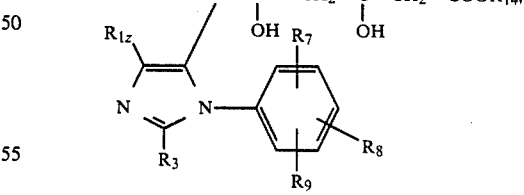

or a pharmaceutically acceptable acid addition salt thereof, wherein $R_{1z}$ is $C_{1-6}$alkyl not containing an asymmetric carbon atom, $C_{3-7}$cycloalkyl or adamantyl-1, said effective amount being an amount effective for the treatment of atherosclerosis.

27. A method of treating atherosclerosis according to claim 26 comprising adminstering to a mammal in need of such treatment an effective amount of a compound of the formula 97
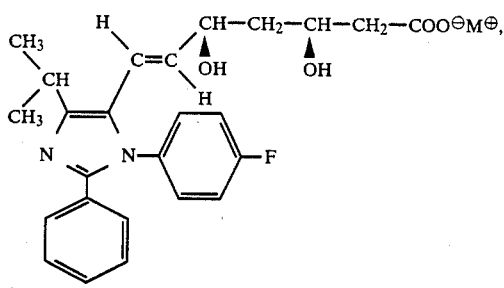
wherein M⊕ is a pharmaceutically acceptable cation, said effective amount being an amount effective for the treatment of atherosclerosis.
* * * * *
98
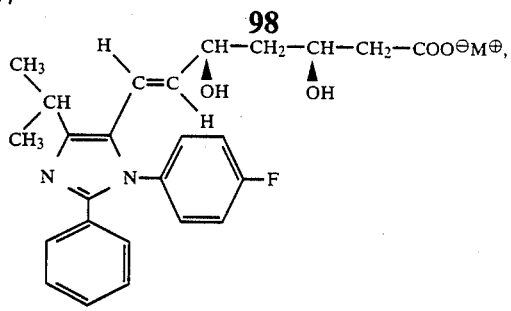
wherein M⊕ is a pharmaceutically acceptable cation, said effective amount being an amount effective for the treatment of atherosclerosis.
* * * * *